US008431335B2

(12) United States Patent
Zhang et al.

(10) Patent No.: US 8,431,335 B2
(45) Date of Patent: Apr. 30, 2013

(54) COMPOSITIONS AND METHODS FOR DETECTION OF LYSOSOMAL STORAGE DISEASE

(75) Inventors: Xiaokui K. Zhang, Northborough, MA (US); Wei-Lien Chuang, Framingham, MA (US); Joan Keutzer, Littleton, MA (US)

(73) Assignee: Genzyme Corporation, Cambridge, MA (US)

( * ) Notice: Subject to any disclaimer, the term of this patent is extended or adjusted under 35 U.S.C. 154(b) by 776 days.

(21) Appl. No.: 11/900,528

(22) Filed: Sep. 12, 2007

(65) Prior Publication Data

US 2008/0145836 A1 Jun. 19, 2008

Related U.S. Application Data

(60) Provisional application No. 60/844,242, filed on Sep. 12, 2006, provisional application No. 60/923,505, filed on Apr. 13, 2007.

(51) Int. Cl.
*C12Q 1/00* (2006.01)
*A01N 43/04* (2006.01)
*A01K 31/70* (2006.01)

(52) U.S. Cl.
USPC .................................. 435/4; 514/23

(58) Field of Classification Search ............ 514/23; 435/4
See application file for complete search history.

(56) References Cited

U.S. PATENT DOCUMENTS

| 4,372,888 A * | 2/1983 | Hjelmeland ................. 552/550 |
| 5,366,963 A | 11/1994 | Ladisch |
| 2005/0125859 A1 | 6/2005 | Garger et al. |
| 2008/0248512 A1 | 10/2008 | Zhang et al. |
| 2008/0248513 A1 | 10/2008 | Zhang et al. |

FOREIGN PATENT DOCUMENTS

WO WO 2008/033427 3/2008

OTHER PUBLICATIONS

Li et al, Clinical Chemistry, 2004, 50(10, 1785-1796.*
Sun, et al., Journal of the Institute of Brewing, 1992, 98, 289-92.*
Tibbot et al., Plant Molecular Biology, 1996, 30: 229-241.*
Chataway et al., Placenta, 1998, 19, 643-654.*
Bodamer, et al., Screening of Newborns for Pompe Disease and/or Other Lysosomal Storage Disorders, Clinical Therapeutics, 2008, vol. 30(Suppl A).
Chamoles, N. et al., Glycogen Storage Disease Type II: Enzymatic Screening in Dried Blood Spots on Filter Paper, Clinica Chimica Acta 347, 2004, 97-102.
Chien, Y et al., Early Detection of Pompe Disease by Newborn Screening Is Feasible: Results from the Taiwan Screening Program, Pediatrics, Jul. 1, 2008, vol. 122.
Gelb et al. Direct Multiplex Assay of Enzymes in Dried Blood Spots by Tandem Mass Spectrometry for the Newborn Screening of Lysosomal Storage Disorders, J. Inherit Metab Dis., 2006, 29; 397-404.
Jack R. et al., The Use of Acarbose Inhibition in the Measurement of Acid Alpha-Glucosidase Activity in Blood Lympocytes for the Diagnosis of Pompe Disease, Genetics in Medicine (2006), vol. 8; p. 307-312.
Kallwass H, et al. Rapid Diagnosis of Late Onset Pompe Disease by Fluorometric Assay of a α-Glucosidase Activities in Dried Blood Spots, Molecular Genetics and Metabolism, 90 (2007) p. 449-452.
Niizawa G. et al., Restrospective Diagnosis of Glycogen Storage Disease Type II by Use of a Newborn-Screening Card, Clinica Chimica Acta 359, Letter to the Editor, 2005, p. 205-206.
Palmer R., et al., Pompe Disease (Glycogen Storage Disease Type II) in Argentineans; Clinical Manifestations and Identification of 9 novel mutations, Neuromolecular Disorders 17 (2007), p. 16-22.
Winchester B., et al., Methods for A Prompt and Reliable Laboratory Diagnosis of Pompe Disease: Report from an International Consensus Meeting, Molecular Genetics and Metabolism 93 (2008), p. 275-281.
Zhang H, et al., Comparison of Maltose and Acarbose As Inhibitors of Maltase-glucoamylase activity in assaying acid α-Glucosidase Activity in Dried Blood Spots for the Diagnosis of Infantile Pompe Disease, Genetics in Medicine, 8(2006) p. 302-306.
Zhang X, et al., Multiplex Enzymes Assay Screening of Dried Blood Spots for Lysosomal Storage Disorders by Using Tandem Mass Spectrometry, Clinical Chemistry 54:10 (2008) p. 1725-1728.
International Preliminary Report on Patentability for PCT/US07/19861, dated Mar. 17, 2009.
International Search Report for PCT/US07/19861, dated Jun. 9, 2008.
Peters et al., 1975, A Microassay for Gaucher's Disease, Clinica Chimica Acta, vol. 60, p. 391-396.
Supplemental European Search Report dated Feb. 2, 2010, corresponding to EP 07 83 8121.
Zhang X K et al: "Multiplex LSD enzyme assay: From research to newborn screening" Journal of Inherited Metabolic Disease, vol. 29, No. Suppl. 1, Aug. 2006, p. 41, XP002566439.
Zhang X Kate et al: "Multiplex enzyme assay screening of dried blood spots for lysosomal storage disorders by using tandem mass spectrometry" Clinical Chemistry, vol. 54, No. 10, Oct. 2008, pp. 1725-1728, XP002566440 ISSN: 0009-9147.
Dean et al. Journal of Biological Chemistry vol. 254, No. 20, 1979, pp. 10001-10005, XP008104928.
Database Medline [Online] Vaccaro et al.: Factors affecting of glucosylceramide to its natural substrate dispersion Retrieved from STN Database accession No. (2591351), Enzyme, 1989, 42, 87-97, Jan. 14, 2013.
Li et al: Direct Multiplex Assay of Lysosomal Enzymes in Dried Blood Spots for Newborn screening, Clinical Chemistry vol. 50, No. 10, 2004, pp. 1785-1796, XP002514511.

* cited by examiner

*Primary Examiner* — Eric S Olson
*Assistant Examiner* — Zhengfu Wang
(74) *Attorney, Agent, or Firm* — Hamilton, Brook, Smith & Reynolds, P.C.

(57) ABSTRACT

The present invention provides compositions for performing assays of enzyme activity associated with lysosomal storage diseases. The invention further provides methods for determining enzyme activity, and methods for the screening for lysosomal storage disease in an individual.

3 Claims, 13 Drawing Sheets

ASM Assay

ABG Assay

GAA Assay

GLA Assay

Substrate – GLA-S
$C_{33}H_{47}N_3O_{10}$
Monoisotopic MW = 645.3261

GLA activity Normal vs. Fabry

GAA activity Normal vs. Pompe

GALC activity Normal vs. Krabbe

ABG activity Normal vs. Gaucher

ASM activity Normal vs. Niemann-Pick A/B

COMPOSITIONS AND METHODS FOR DETECTION OF LYSOSOMAL STORAGE DISEASE

This application claims priority to U.S. Provisional Application Ser. Nos. 60/844,242, filed Sep. 12, 2006 and 60/923,505, filed Apr. 13, 2007, the contents of which are incorporated herein in their entirety.

BACKGROUND

The lysosomal storage diseases are a group of disorders that manifest from birth to adulthood and result in damage to both somatic organs and the central nervous system. Currently, there are enzyme replacement therapies that have been shown effective in treating Gaucher disease (acid β-glucocerebrosidase (ABG) deficiency), Fabry disease (acid α-galactosidase (GLA) deficiency), and Pompe disease (lysosomal acid α-glucosidase (GAA) deficiency). It is expected that similar therapy will be developed for Niemann-Pick A/B disease type A and B (acid sphingomyelinase (ASM) deficiency). In addition, it has been suggested that presymptomatic initiation of bone marrow transplantation may prevent the neural degeneration observed in Krabbe disease (galactocerebroside β-galactosidase (GALC) deficiency).

For each of these diseases, early therapeutic intervention and thus, early, presymptomatic detection of the disease will be important to maximize treatment benefit. In particular, newborn screening for the enzyme deficiencies associated with the lysosomal storage diseases will provide a greater probability of effective treatment compared to diagnosis of the disease once symptoms have manifested.

A recent paper by Li et al. (Clinical Chemistry (2004) 50: 1785-1796) teaches assays for determining ABG, GLA, GAA, ASM, and GALC enzyme activity from dried blood spots obtained from newborn infants using mass spectrometry. The instant invention is based, in part, on the independent optimization of assays for detection of these enzymes to provide more robust, more reliable methods for determining enzyme activity and disease diagnosis and screening.

SUMMARY OF THE INVENTION

The present invention provides a series of assay mixtures that can be used to determine enzyme activity in an individual. The assay mixtures of the invention include a substrate for the enzyme activity to be tested, an internal standard, detergent, and a buffer. In preferred embodiment, the assay mixture can also include one or more inhibitors of non-specific enzyme activity.

In one aspect, the invention provides a composition comprising at least 0.6 mM C12-glucosyl ceramide, 13.33 µM C14 ceramide, 16 g/L sodium taurocholate, and a buffer adjusted to a pH of 5.1. Preferably the composition includes 0.67 mM C12-glucosyl ceramide. Preferably, the buffer is 0.62 M phosphate/citrate.

In one aspect, the invention provides a composition comprising 0.33 mM C6-sphingomyelin, 6.67 µM C4 ceramide, 1 g/L sodium taurocholate, 0.6 mM zinc chloride, and a buffer adjusted to a pH of 5.7. Preferably the buffer is 0.92 M sodium acetate.

In one aspect, the invention provides a composition comprising 1 mM C8-galactosyl ceramide, 6.67 µM C10-ceramide, 9.6 g/L sodium taurocholate, 1.2 g/L oleic acid, and a buffer Adjusted to a pH of 4.4. Preferably, the buffer is 0.18 M phosphate/citrate.

In another aspect, the invention provides a composition comprising 0.667 mM (7-benzoylamino-heptyl)-{2-[4-(3,4,5-trihydroxy-6-hydroxymethyl-tetrahydro-pyran-2-yloxy)-phenylcarbamoyl]-ethyl}-carbamic acid tert-butyl ester, 6.67 µM 7-d5-benzoylamino-heptyl)[2-(4-hydroxy-phenylcarbamoyl)-ethyl]-carbamic acid tert-butyl ester, 10 g/L 3-[(3-cholamidopropyl)dimethylammonio]-1- propanesulfonate (CAS No. 75621-03-3; hereinafter "CHAPS"), 13.3 µM acarbose and a buffer adjusted to a pH of 4.0. Preferably, the buffer is 0.3 M phosphate/citrate.

In a further aspect, the invention provides a composition comprising 3.33 mM (6-Benzoylamino-hexyl)-{2-[4-(3,4,5-trihydroxy-6-hydroxymethyl-tetrahydro-pyran-2-yloxy)-phenylcarbamoyl]-ethyl}-carbamic acid tert-butyl ester, 6.67 µM 6-d5-Benzoylamino-hexyl)-[2-(4-hydroxy-phenylcarbamoyl)-ethyl]-carbamic acid tert-butyl ester, 3 g/L sodium taurocholate, 160 mM N-acetylgalactosamine, and a buffer adjusted to a pH of 4.6. Preferably, the buffer is 0.142 M sodium acetate.

In a further aspect, the above compositions can be included, either singularly, or in combination of individual compositions in a kit, including appropriate packaging materials. The above compositions can also be in lyophilized form, or in a concentrated form, such as a 0.5× to 50× formulation, including a 2×, 10×, 20×, 30×, or 40× concentrated formulation.

In a further aspect any or all of the foregoing compositions can be mixed in bulk for multiple reactions. For example, a sufficient amount of the various components of each assay mix can be mixed to provide a sufficient volume of assay mix to carry out 2 to 1200 or more individual enzyme reactions. Preferably a sufficient amount of the each reaction mix will be prepared to perform 100, 200, 300, 400, 500, 600, and up to 1200 or more enzyme reactions.

In one aspect, the invention provides a composition comprising C12-glucosyl ceramide, C14 ceramide, sodium taurocholate, and a buffer adjusted to a pH of 5.1, wherein the ratio of C12-glucosyl ceramide to C14 ceramide is 50:1, the ratio of sodium taurocholate to C12-glucosyl ceramide is 45:1, and where the ratio of buffer to C12-glucosyl ceramide is 925:1.

In a further aspect, the invention provides a composition comprising C6-sphingomyelin, C4 ceramide, sodium taurocholate, zinc chloride, and a buffer adjusted to a pH of 5.7, wherein the ratio of C6-sphingomyelin to C4 ceramide is 50:1, the ratio of sodium taurocholate to C6-sphingomyelin is 5.6:1, the ratio of zinc chloride to C6-sphingomyelin is 1.82:1, and the ratio of buffer to C-6 sphingomyelin is 2788:1.

In one aspect, the invention provides a composition comprising C8-galactosyl ceramide, C10-ceramide, sodium taurocholate, oleic acid, and a buffer adjusted to a pH of 4.4, wherein the ratio of C8-galactosyl ceramide to CO-ceramide is 150:1, the ratio of sodium taurocholate to C8-galactosyl ceramide is 17.8:1, the ratio of oleic acid to C8-galactosyl ceramide is 4.25:1, and the ratio of buffer to C8-galactosyl ceramide is 180:1

In a further aspect, the invention provides a composition comprising (7-benzoylamino-heptyl)-{2-[4-(3,4,5-trihydroxy-6-hydroxymethyl-tetrahydro-pyran-2-yloxy)-phenylcarbamoyl]-ethyl}-carbamic acid tert-butyl ester, 7-d5-benzoylamino-heptyl)-[2-(4-hydroxy-phenylcarbamoyl)-ethyl]-carbamic acid tert-butyl ester, CHAPS, acarbose and a buffer adjusted to a pH of 4.0, wherein the ratio of (7-benzoylamino-heptyl)-{2-[4-(3,4,5-trihydroxy-6-hydroxymethyl-tetrahydro-pyran-2-yloxy)-phenylcarbamoyl]-ethyl}-carbamic acid tert-butyl ester to 7-d5-benzoylamino-heptyl)-[2-(4-hydroxy-phenylcarbamoyl)-ethyl]-carbamic acid tert-butyl ester is 100:1, the ratio of CHAPS to (7-benzoylamino-heptyl)-{2-[4-(3,4,5-trihydroxy-6-hydroxymethyl-tetrahydro-pyran-2-yloxy)-phenylcarbamoyl]-ethyl}-carbamic acid tert-butyl ester is 24.3:1, the ratio of acarbose to (7-benzoylamino-heptyl)-{2-[4-(3,4,5-trihydroxy-6-hydroxymethyl-tetrahydro-pyran-2-yloxy)-phenylcarbamoyl]-ethyl}-carbamic acid tert-butyl ester is 0.02:1, and the ratio of buffer to (7-benzoylamino-heptyl)-{2-[4-(3,4,5-trihydroxy-6-hydroxymethyl-tetrahydro-pyran-2-yloxy)-phenylcarbamoyl]-ethyl}-carbamic acid tert-butyl ester is 450:1.

In a still further aspect, the invention provides a composition comprising (6-Benzoylamino-hexyl)-{2-[4-(3,4,5-trihydroxy-6-hydroxymethyl-tetrahydro-pyran-2-yloxy)-phenylcarbamoyl]-ethyl}-carbamic acid tert-butyl ester, 6-d5-Benzoylamino-hexyl)-[2-(4-hydroxy-phenylcarbamoyl)-ethyl]-carbamic acid tert-butyl ester, sodium taurocholate, N-acetylgalactosamine, and a buffer adjusted to a pH of 4.6, wherein the ratio of (6-Benzoylamino-hexyl)-{2-[4-(3,4,5-trihydroxy-6-hydroxymethyl-tetrahydro-pyran-2-yloxy)-phenylcarbamoyl]-ethyl}-carbamic acid tert-butyl ester to 6-d5-Benzoylamino-hexyl)-[2-(4-hydroxy-phenylcarbamoyl)-ethyl]-carbamic acid tert-butyl ester is 499:1, the ratio of sodium taurocholate to (6-Benzoylamino-hexyl)-{2-[4-(3,4,5-trihydroxy-6-hydroxymethyl-tetrahydro-pyran-2-yloxy)-phenylcarbamoyl]-ethyl}-carbamic acid tert-butyl ester is 1.68:1, the ratio of N-acetylgalactosamine to (6-Benzoylamino-hexyl)-{2-[4-(3,4,5-trihydroxy-6-hydroxymethyl-tetrahydro-pyran-2-yloxy)-phenylcarbamoyl]-ethyl}-carbamic acid tert-butyl ester is 48:1, and the ratio of buffer to (6-Benzoylamino-hexyl)-{2-[4-(3,4,5-trihydroxy-6-hydroxymethyl-tetrahydro-pyran-2-yloxy)-phenylcarbamoyl]-ethyl}-carbamic acid tert-butyl ester is 43:1.

In the foregoing compositions, it will be understood by one of skill in the art that the components may be present in the composition at about the concentrations shown above, wherein "about" refers to a variance of +/−2%, 5%, 7%, and up to 10% of the stated value, wherein the concentration or amount of a given component is determined using measurements and calculations well known in the art.

In one aspect, the invention provides a method of determining acid glucocerebrosidase activity in a subject, the method comprising the steps of: extracting acid glucocerebrosidase from a dried blood spot obtained from the subject using an aqueous buffer solution; adding substrate and an internal standard to the extracted acid glucocerebrosidase; reacting the substrate with the extracted acid glucocerebrosidase; quenching the reaction by addition of four volumes of a solution consisting essentially of ethyl acetate/methanol (1/1); extracting the reaction product and internal standard by adding at least 2 volumes of ethyl acetate and at least 2 volumes of water to the quenched reaction to form a two-phase system. In one embodiment, the assays described herein are performed in a multiplex format (that is, where the reaction mixes from more than one assay reaction, preferably all five assays, are pooled following the quenching step), in which case the pooled reaction products are extracted by adding at least a ⅗ volume of ethyl acetate and at least a ⅗ volume of water to the quenched reaction. After extraction, the extracted product and internal standard are harvested from the upper phase and then purified, preferably by passage through silica gel which is then washed with a 19:1 mixture of ethyl acetate/MeOH. The product and the internal standard are then quantified to determine the acid glucocerebrosidase activity.

Preferably, the substrate in the foregoing method is C12 glucosyl ceramide and the internal standard is C14 ceramide. It is preferred that the C12 glucosyl ceramide is present at a concentration of 0.6 mM, preferably a concentration of 0.67 mM. In addition, it is preferred that during the step of reacting the substrate with the extracted acid glucocerebrosidase, the concentration of substrate is at least 0.4 mM.

The step of quantifying is preferably performed by tandem mass spectrometry.

The invention also provides a method of identifying an individual having decreased acid glucocrebrosidase activity by first determining acid glucocerebrosidase activity in said individual according to the foregoing method and also determining acid glucocerebrosidase activity in a population of at least three presumptive normal subjects according to the same method. A subject is a "presumptive normal" subject when it is not known whether the subject has a decrease level of activity for the enzyme being assayed. The mean acid glucocerebrosidase activity is then calculated for the population of subjects and compared to the acid glucocerebrosidase activity of the individual. If the acid glucocerebrosidase activity of the individual is less than 20-30% of the mean acid glucocerebrosidase activity, preferably less than 30%, and more preferably less than 20%, then the individual is identified as having decreased acid glucocrebrosidase activity.

In one aspect, the invention provides a method of determining acid sphingomyelinase activity in a subject, the method comprising the steps of: extracting acid sphingomyelinase from a dried blood spot obtained from the subject using an aqueous buffer solution; adding substrate and an internal standard to the extracted acid sphingomyelinase; reacting the substrate with the extracted acid sphingomyelinase; quenching the reaction by addition of four volumes of a solution consisting essentially of ethyl acetate/methanol (1/1); extracting the reaction product and internal standard by adding at least 2 volumes of ethyl acetate and at least 2 volumes of water to the quenched reaction to form a two-phase system. In one embodiment, the assays described herein are performed in a multiplex format (that is, where the reaction mixes from more than one assay reaction, preferably all five assays, are pooled following the quenching step), in which case the pooled reaction products are extracted by adding at least a ⅗ volume of ethyl acetate and at least a ⅗ volume of water to the quenched reaction. After extraction, the extracted product and internal standard are harvested from the upper phase and then purified, preferably by passage through silica gel which is then washed the silica gel with a 19:1 mixture of ethyl acetate/MeOH. The product and the internal standard are then quantified to determine the acid sphingomyelinase activity. Preferably, the substrate is C6 sphingomyelin and the internal standard is C4 ceramide.

The step of quantifying is performed preferably by tandem mass spectrometry.

In one embodiment of the foregoing method, zinc chloride is also added to the reaction mix, preferably at a concentration of 0.6 mM. In addition, it is preferred that during the step of reacting the substrate with the extracted acid sphingomyelinase the substrate concentration is at least 0.2 mM, and the pH is 5.7.

In one aspect, the invention provides a method of identifying an individual having decreased acid sphingomyelinase activity comprising, determining acid sphingomyelinase activity in the individual according to the foregoing method and also determining acid sphingomyelinase activity in a population of at least three presumptive normal subjects according to the same method. The mean acid sphingomyelinase activity is then calculated for the population of subjects and compared to the acid sphingomyelinase activity of the individual. If the acid sphingomyelinase activity of the individual is less than 20% of the mean acid sphingomyelinase activity, the individual is identified as having decreased acid sphingomyelinase activity.

In a further aspect, the invention provides a method of determining galactocerebroside β-galactosidase activity in a subject, the method comprising the steps of: contacting a dried blood spot from said subject having a diameter of 3.2 mm and comprising galactocerebroside β-galactosidase with a substrate and an internal standard; reacting the substrate with the galactocerebroside β-galactosidase; quenching the reaction by addition of at least 2 volumes of a solution consisting essentially of ethyl acetate/methanol (1/1); extracting the reaction product and internal standard by adding at least 2 volumes of ethyl acetate and at least 2 volumes of water to the quenched reaction to form a two-phase system, and harvesting the extracted product and internal standard from the upper phase; purifying the reaction product and internal standard, preferably by passage of the extract through silica gel which is then washed with a 19:1 mixture of ethyl acetate/MeOH; and quantifying the product and the internal standard to determine the galactocerebroside β-galactosidase activity. Preferably, the substrate is C8-galactosyl ceramide and the internal standard is C10-ceramide. More preferably, the C8-galactosyl ceramide is present at a concentration of 1 mM.

While preferred that the method for determining galactocerebroside β-galactosidase activity is performed using a 3.2 mm dried blood spot, the method can also be performed by substituting an extract of a 3.2 mm dried blood spot as described in further detail herein below. It is also envisioned that the method for determining galactocerebroside β-galactosidase activity can be performed using a combination of a 3.2 mm dried blood spot and a dried blood spot extract.

In one embodiment of the foregoing method, the reaction mix (i.e., the contacting step) includes oleic acid and sodium taurocholate. Preferably, the oleic acid is at a concentration of 1.2 g/L. It is preferred that the substrate concentration is at least 1 mM during the step of reacting the substrate with the galactocerebroside β-galactosidase said.

In a preferred embodiment, the enzyme activity is quantified by tandem mass spectrometry.

The invention also provides a method of identifying an individual having decreased galactocerebroside β-galactosidase activity comprising, determining galactocerebroside β-galactosidase activity in the individual according to the foregoing method, and also determining galactocerebroside β-galactosidase activity in a population of at least three presumptive normal subjects according to the same method. The mean galactocerebroside β-galactosidase activity is then calculated for the population of subjects and compared with the galactocerebroside β-galactosidase activity of the individual. If the galactocerebroside β-galactosidase activity of the individual is less than 10% of the mean galactocerebroside β-galactosidase activity, the individual is identified as having decreased galactocerebroside β-galactosidase activity.

In a further aspect, the invention provides a method of determining acid glucosidase activity in a subject, the method comprising the steps of: extracting acid glucosidase from a dried blood spot obtained from the subject using an aqueous buffer solution; adding substrate and an internal standard to the extracted acid glucosidase; reacting the substrate with the extracted acid glucosidase; quenching the reaction by addition of four volumes of a solution consisting essentially of ethyl acetate/methanol (1/1); extracting the reaction product and internal standard by adding at least 2 volumes of ethyl acetate and at least 2 volumes of water to the quenched reaction to form a two-phase system. In one embodiment, the assays described herein are performed in a multiplex format (that is, where the reaction mixes from more than one assay reaction, preferably all five assays, are pooled following the quenching step), in which case the pooled reaction products are extracted by adding at least a ⅗ volume of ethyl acetate and at least a ⅗ volume of water to the quenched reaction. After extraction, the extracted product and internal standard are harvested from the upper phase and then purified, preferably by passage through silica gel which is then washed with a 19:1 mixture of ethyl acetate/MeOH. The product and the internal standard are then quantified to determine the acid glucosidase activity. It is preferred that the substrate is (7-benzoylamino-heptyl)-{2-[4-(3,4,5-trihydroxy-6-hydroxymethyl-tetrahydro-pyran-2-yloxy)-phenylcarbamoyl]-ethyl}-carbamic acid tert-butyl ester and the internal standard is 7-d5-benzoylamino-heptyl)-[2-(4-hydroxy-phenylcarbamoyl)-ethyl]-carbamic acid tert-butyl ester.

In one embodiment, 10 g/L CHAPS is included in the reaction mixture (i.e., the adding step). In a further preferred embodiment, the step of adding also includes adding 13.3 μM acarbose.

It is preferred that the substrate concentration is at least 0.4 mM during the step of reacting the substrate with the acid glucosidase.

In a preferred embodiment, the enzyme activity is quantified by tandem mass spectrometry.

In one aspect, the invention provides a method of identifying an individual having decreased acid glucosidase activity comprising, determining acid glucosidase activity in said individual according to the foregoing method, and also determining acid glucosidase activity in a population of at least three presumed normal subjects according to the same method. The mean acid glucosidase activity of said population of subjects is calculated and compared to the acid glucosidase activity of the individual. If the acid glucosidase activity of the individual is less than 20-30% of the mean acid glucosidase activity, preferably less than 30%, and more preferably less than 20%, the individual is identified as having decreased acid glucosidase activity.

In another aspect, the invention provides a method of determining acid α-galactosidase A activity in a subject, the method comprising the steps of: extracting acid α-galactosidase A from a dried blood spot obtained from the subject using an aqueous buffer solution; adding substrate and an internal standard to the extracted acid α-galactosidase A; reacting the substrate with the extracted acid α-galactosidase A; quenching the reaction by addition of four volumes of a solution consisting essentially of ethyl acetate/methanol (1/1); extracting the reaction product and internal standard by adding at least 2 volumes of ethyl acetate and at least 2 volumes of water to the quenched reaction to form a two-phase system. In one embodiment, the assays described herein are performed in a multiplex format (that is, where the reaction mixes from more than one assay reaction, preferably all five assays, are pooled following the quenching step), in which case the pooled reaction products are extracted by adding at least a ⅗ volume of ethyl acetate and at least a ⅗ volume of water to the quenched reaction. After extraction, the extracted product and internal standard are harvested from the upper phase and then purified, preferably by passage through silica gel which is then washed with a 19:1 mixture of ethyl acetate/MeOH. The product and the internal standard are then quantified to determine the acid α-galactosidase A activity.

In a preferred embodiment, the substrate is (6-benzoylamino-hexyl)-{2-[4-(3,4,5-trihydroxy-6-hydroxymethyl-tetrahydro-pyran-2-yloxy)-phenylcarbamoyl]-ethyl}-carbamic acid tert-butyl ester and the internal standard is 6-d5- benzoylamino-hexyl)-[2-(4-hydroxy-phenylcarbamoyl)-ethyl]-carbamic acid tert-butyl ester. Preferably, the substrate is at a concentration of 3.33. mM and the internal standard is at a concentration of 6.67 µM.

In one embodiment, the step of adding also includes adding 3 g/L sodium taurocholate, and further includes adding 160 mM N-acetylgalactosamine. In a further preferred embodiment, the step of adding includes adding 0.142 M sodium acetate.

It is preferred that the substrate concentration is at least 2 mM. during the step of reacting the substrate with the α-galactosidase A.

In a preferred embodiment, the step of quantifying is by tandem mass spectrometry.

In a further aspect, the invention provides a method of identifying an individual having decreased α-galactosidase A activity comprising determining acid α-galactosidase A activity in said individual according to the foregoing method, and also determining acid α-galactosidase A activity in a population of at least three subjects according to the same method. The mean acid α-galactosidase A activity of the population of subjects is calculated and compared to the acid α-galactosidase A activity of the individual. If the acid α-galactosidase A activity of the individual is less than 10-20% of the mean acid α-galactosidase A activity, preferably less than 20%, and more preferably less than 10%, the individual is identified as having decreased α-galactosidase A activity.

In a further aspect, the invention provides a method of determining the activity of acid glucocerebrosidase, acid sphingomyelinase, galactocerebroside β-galactosidase, acid glucosidase, and acid α-galactosidase in a subject, the method comprising the steps of: extracting acid glucocerebrosidase from a first dried blood spot punch obtained from the subject using an aqueous buffer solution; extracting acid sphingomyelinase from a second dried blood spot punch obtained from the subject using an aqueous buffer solution; extracting acid glucosidase from a third dried blood spot punch obtained from the subject using an aqueous buffer solution; extracting acid α-galactosidase A from a fourth dried blood spot punch obtained from the subject using an aqueous buffer solution; adding a first substrate and first internal standard to the extracted acid glucocerebrosidase to form a first reaction mix; adding a second substrate and second internal standard to the extracted acid sphingomyelinase to form a second reaction mix; adding a third substrate and third internal standard to the extracted acid glucosidase to form a third reaction mix; adding a fourth substrate and fourth internal standard to the extracted acid α-galactosidase A to form a fourth reaction mix; contacting a fifth dried blood spot punch from said subject having a diameter of 3.2 mm and comprising galactocerebroside β-galactosidase with a fifth substrate and fifth internal standard to form a fifth reaction mix; reacting the first, second, third, and fourth substrate with the extracted acid glucocerebrosidase, acid sphingomyelinase, acid glucosidase, and acid α-galactosidase, respectively to form a first, second, third, and fourth reaction product; reacting the fifth substrate with the galactocerebroside β-galactosidase to form a fifth reaction product quenching each reaction by adding four volumes of a solution consisting essentially of ethyl acetate/methanol (1/1) to each reaction mix; combining each reaction mix in a single container; extracting the reaction products and internal standards by adding at least a ⅗ volume of ethyl acetate and at least a ⅗ volume of water to the quenched reactions to form a two-phase system, and harvesting the extracted product and internal standard from the upper phase; purifying the reaction products and internal standards, preferably by passage of the extract through silica gel which is then washed with a 19:1 mixture of ethyl acetate and water; and quantifying the products and the internal standards to determine the acid glucocerebrosidase, acid sphingomyelinase, galactocerebroside β-galactosidase, acid glucosidase, and acid α-galactosidase activities.

In a preferred embodiment, the concentration of substrate added to the extracted acid glucocerebrosidase is 0.67 mM. A concentration of 0.6 mM zinc chloride can be added to the extracted acid sphingomyelinase, and the second reaction mix is preferably at a pH of 5.7.

A concentration of 10 g/L CHAPS, and optionally a concentration of 13.3 µM acarbose can be added to the extracted acid glucosidase.

It is preferred that the concentration of substrate added to prepare the fourth reaction mix is 3.33 mM, and that the concentration of internal standard added to prepare the fourth reaction mix is 6.67 µM.

In a preferred embodiment, 3 g/L sodium taurocholate, 160 mM N-acetylgalactosamine, and 0.142 M sodium acetate are added to prepare the fourth reaction mix.

In a further embodiment, the concentration of substrate added to prepare the fifth reaction mix is 1 mM. In addition, 1.2 g/L oleic acid is preferably added to prepare the fifth reaction mix.

In each of the foregoing aspects, it is possible to omit the step of purifying the reaction products by passage through a silica gel. The silica gel purification step can be omitted or replaced by an alternate procedure to clean up the reaction products and internal standards. Such methods are well known in the art.

The invention also provides a method of determining acid glucocerebrosidase activity in a subject, including the steps of: (a) extracting acid glucocerebrosidase from a dried blood spot obtained from the subject in an aqueous buffer solution that includes a detergent, and dividing the extract into a first and second sample; (b) adding a fluorogenic substrate and conduritol B epoxide to the first sample to form a first reaction mix, and adding the fluorogenic substrate to the second sample to form a second reaction mix; (c) reacting the substrate with the extracted glucocerebrosidase in the first and second reaction mixes; (d) quenching the reactions; (e) centrifuging said first and second reaction mixes at 2000-3000 rpm for 30-90 minutes; (f) determining the fluorescence emitted from each of the first and second reaction mixes; and (g) subtracting the level of fluorescence of the first reaction mix from the level of fluorescence of the second reaction mix to obtain a differential fluorescence, thereby determining the acid glucocerebrosidase activity in the subject.

The fluorogenic substrate can be a substrate that is cleaved by a β-glucosidase enzyme. For example, fluorogenic substrates that can be used in the method include, but are not limited to 4-methylumbelliferyl-β-D-glucopyranoside (4-MU-β-Glu), 4-pentafluoroethylumbelliferyl-beta-D-glucoside, 4-trifluoromethylumbelliferyl-beta-D-glucoside, and 4-heptylumbelliferyl-beta-D-glucoside. Preferably, the substrate is 4-methylumbelliferyl-β-D-glucopyranoside (4-MU-β-Glu).

This method can further include the step of comparing the differential fluorescence to a standard curve to determine the acid glucocerebrosidase activity in the subject.

The detergent used in the foregoing method is preferably sodium taurodeoxycholate. It is further preferred that the sodium taurodeoxycholate by of high purity, such as for example, 90, 95, 97, 98, 99, or up to 100% pure. Preferably, the sodium taurodeoxycholate is at least 97% pure.

The foregoing method for determining acid glucocerebrosidase activity in a subject can be used to screen or diagnose Gaucher disease, or can be used to identify a subject for treatment.

In the foregoing methods, it will be understood by one of skill in the art that the components used in the method (i.e., the assay components, such as substrate, internal standard, and the like) may be used at about the concentrations shown above, wherein "about" refers to a variance of +/−2%, 5%, 7%, and up to 10% of the stated value, wherein the concentration or amount of a given component is determined using measurements and calculations well known in the art.

The invention still further provides a method of identifying an individual with decreased acid glucocerebrosidase activity including the steps of: determining acid glucocerebrosidase activity in the individual according to the foregoing method; determining acid glucocerebrosidase activity in a population of at least two presumptive normal subjects according to the foregoing method; calculating the mean acid glucocerebrosidase activity of the population of at least two presumptive normal subjects; and comparing the mean acid glucocerebrosidase activity to the acid glucocerebrosidase activity of the individual, wherein if the acid glucocerebrosidase activity of the individual is less than 30% of the mean acid glucocerebrosidase activity, the individual is identified as having decreased acid glucocerebrosidase activity.

In one aspect, the invention provides a method for selecting a treatment regimen for a patient based on the activity of the ABG, ASM, GAA, GALC, or GLA enzymes. For example, by determining the activity of one or more of these enzymes in an individual, a physician or other health care professional can use that information to make decisions as to the proper follow-up, or treatment (e.g., enzyme replacement therapy or bone marrow transplantation) for the individual.

The methods of the instant invention can also be used to monitor treatment in a patient. For example, after starting a patient on a treatment program for deficiency in one or more of the ABG, ASM, GAA, GALC, or GLA enzymes, enzyme activity can be assayed at relevant time points (as determined by the patient's physician) to determine whether enzyme activity levels are higher than prior to the commencement of treatment, and thus, monitor the efficacy of a particular treatment.

DETAILED DESCRIPTION

Figure 1A:
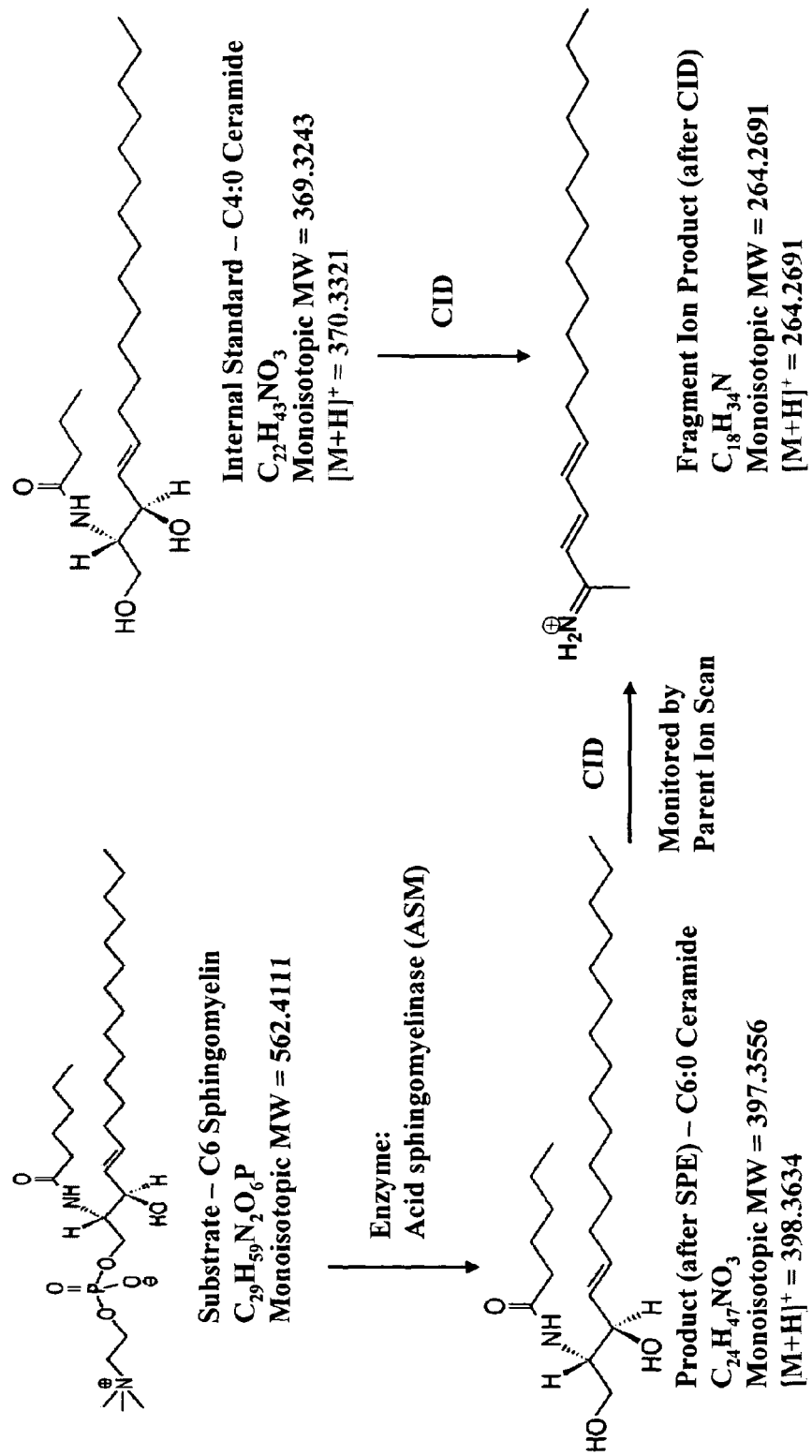
FIG. 1 (A-E) shows a schematic summary of the activity of the target enzyme on the substrate and internal standards used in the methods of the invention.
Figure 1B:
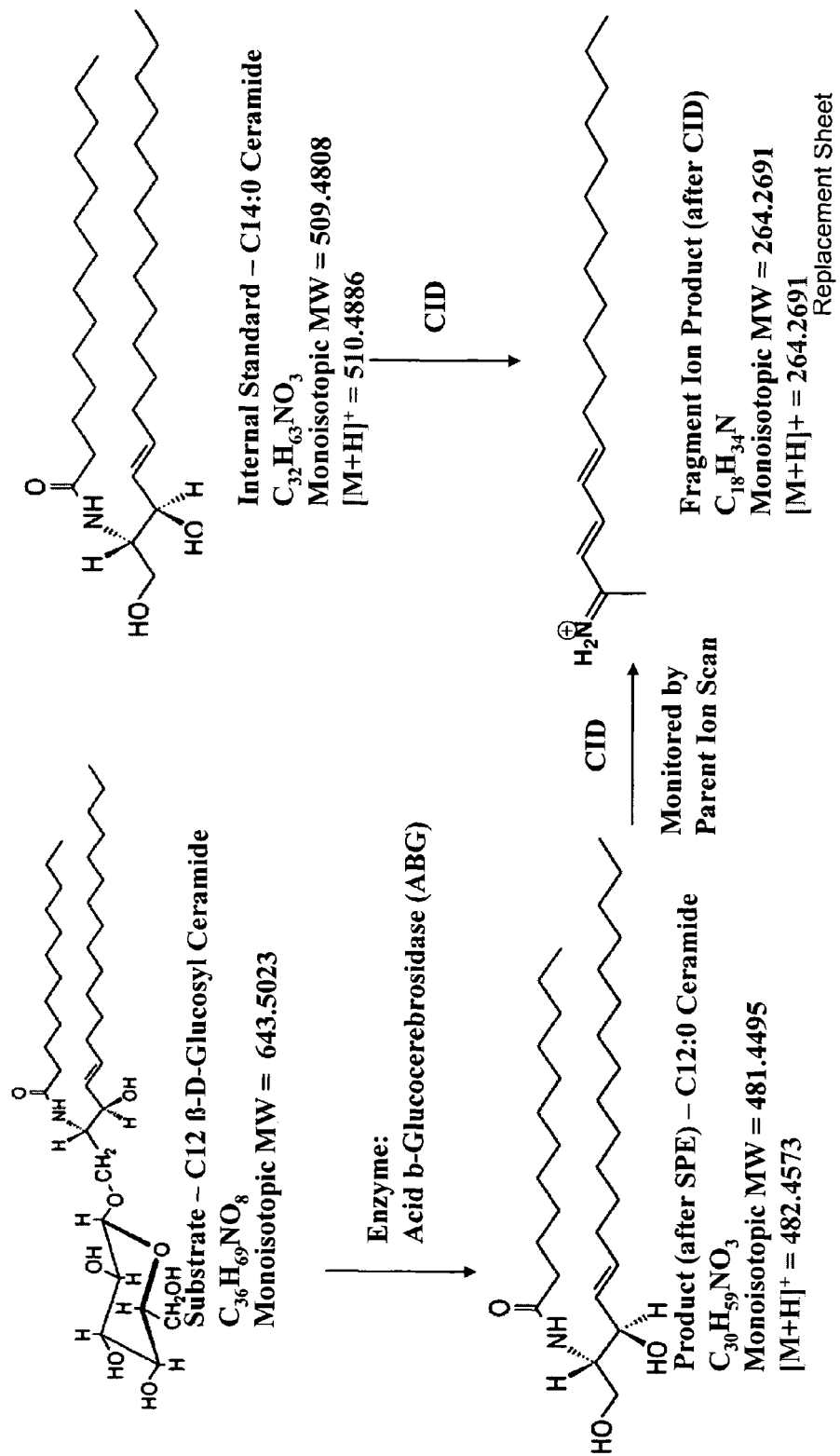
Figure 1C:
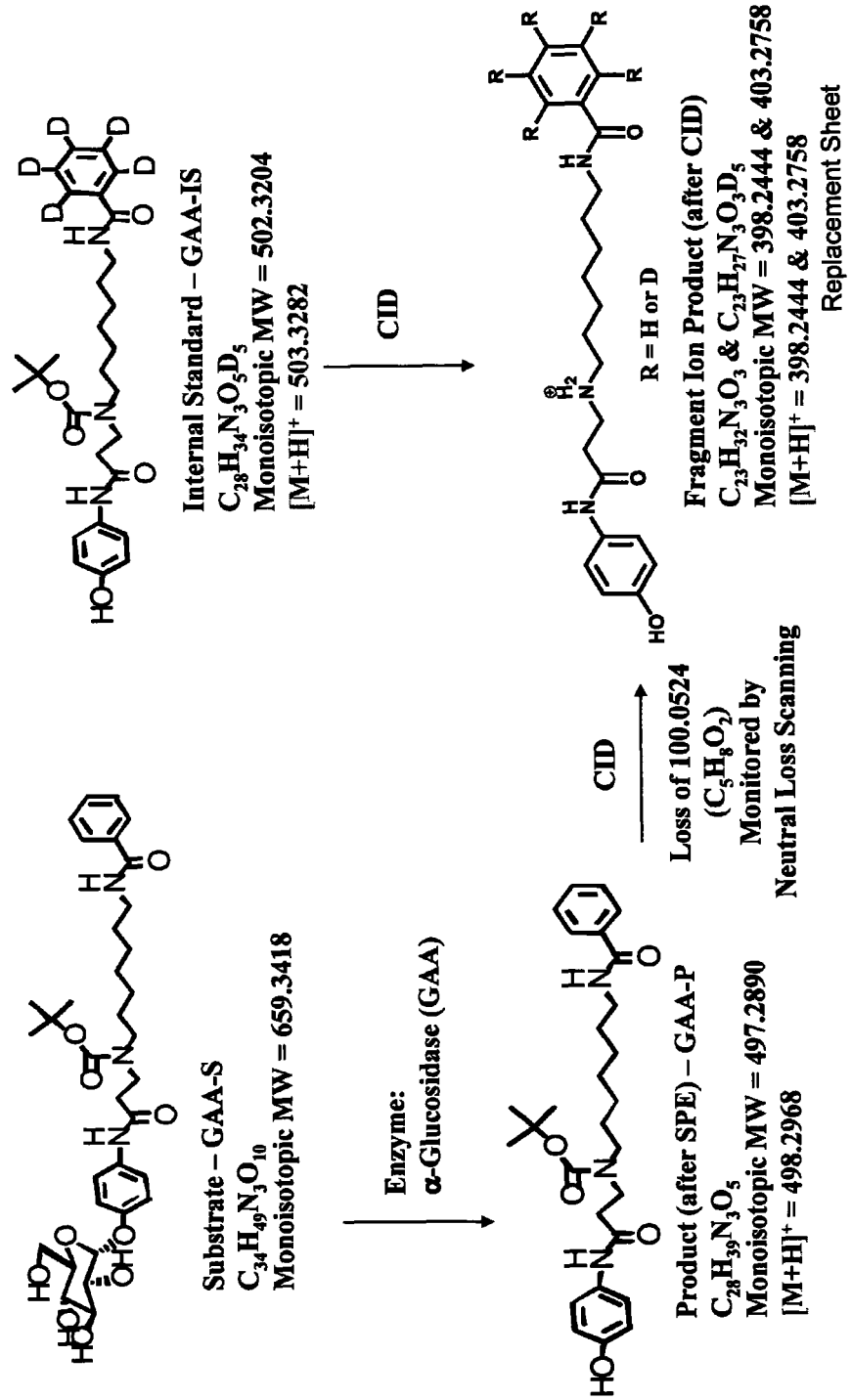

The present invention is based, in part, on the discovery that specific combinations of substrate, internal standard, buffer, and enzyme inhibitors, present in predetermined ratios, and at specific pH can be used to accurately assay for the activity of the lysosomal enzymes implicated in the etiology of Fabry, Gaucher, Krabbe, Niemann-Pick A/B, and Pompe diseases.

The invention is also based on the discovery that, using the specific components and ratios of components for determining enzyme activity, assays for activity can be multiplexed such that a single round of screening assays can determine the enzyme activity associated with all five lysosomal storage diseases. Alternatively, each assay and determination of enzyme activity can be performed separately. These assays can be performed on blood samples from newborn infants, and provide a robust method for making an early determination of decreased enzyme activity associated with one or more of Fabry, Gaucher, Krabbe, Niemann-Pick A/B, and Pompe diseases, thus permitting early therapeutic intervention.

Assay Components

The compositions and methods described herein useful for the determination of the activity of enzymes associated with the five lysosomal storage diseases: Gaucher disease (acid β-glucocerebrosidase (ABG) deficiency), Fabry disease (acid α-galactosidase (GLA) deficiency), Pompe disease (lysosomal acid α-glucosidase (GAA) deficiency), Niemann-Pick A/B disease (acid sphingomyelinase (ASM) deficiency), and Krabbe disease (galactocerebroside β-galactosidase (GALC) deficiency).

Described broadly, the components utilized to determine ABG, GLA, GAA, ASM, or GALC enzyme activity include a substrate, internal standard, and detergent. The substrates used in the activity assays can be the natural substrates for each of ABG, GLA, GAA, ASM, and GALC, or can be a modified version of the natural substrate, or a synthetic substrate. In a preferred embodiment, the substrate for ABG, ASM, and GALC assays are synthetic sphingolipids containing N-linked fatty acyl chains that are shorter than the typical natural substrates (the substrates, products, and internal standards for each enzyme assay are shown in FIG. 1). These synthetic substrates have the advantage that the corresponding products (i.e., the product produced by the action of ABG, ASM, and GALC on its corresponding substrate) are non-natural ceramides and are produced without interference from endogenous natural ceramides. In a further preferred embodiment, the substrate for GAA and GLA are water-soluble polysaccharide substrates, or synthetic lipid substrates. Preferably, the GAA and GLA substrates are the synthetic lipidated substrates shown in FIG. 1.

The internal standards used in the activity assays are generally similar in structure to the product generated by the action of the five enzymes on their respective substrates. The GAA and GLA assays utilize internal standards that are chemically identical but isotopically distinguishable from the enzymatically generated products. The ABG, ASM, and GALC assays utilize internal standards that are close in structure to the product but not chemically identical. The specific internal standards used for each of the five enzyme assays are shown in FIG. 1.

Substrates and internal standards can be obtained commercially from vendors known to those of skill in the art (e.g., Avanti Polar Lipids, Alabaster, Ala.). Alternatively, substrates and internal standards may be synthesized prior to use in the methods of the invention. A specific description of the synthesis of the internal standards and substrates for the GAA and GLA substrates and internal standards is provided in Example 1.

In one embodiment, the enzyme assay reaction mixtures can include components that inhibit the activity of other enzymes (e.g., non-ABG, GLA, GAA, ASM, or GALC enzymes) that may interfere with the assay. Inhibitors for interfering enzymes are known in the art and are collectively referred to as glucose-like competitive inhibitors. For example, in the GAA assay, blood cells contain a second acid α-glucosidase that can interfere with the assay for GAA. Maltose or acarbose can be used in the assay mixture to inhibit the activity of this contaminating enzyme. In the GLA assay, N-acetyl galactosamine can be used as an inhibitor of alpha-galactosidase B, an interfering enzyme that can confound the assay if not inhibited. In another embodiment, the enzyme assay reaction mixture can include components that boost the activity of the enzymes. For example in the ASM assay, zinc chloride provides the Zn++ cofactor needed for optimal enzyme activity.

Synthesis of Substrates and Internal Standards

The substrates and internal standards used in the instant invention may be obtained from commercial sources (e.g., Avanti Polar Lipids), or may be synthesized prior to use. The following section provides a description of the synthesis of substrates and internal standards for each of the five assays.

ABG Substrate/Internal Standard Synthesis

The currently synthesis strategy is based on condensation of the two key intermediates and a following deprotection step using sodium methylate. Alternative to the synthesis shown below would be a direct glycosylation of the C12-ceramide (the ABG assay product). If this later route is followed, however, the resulting β-glucocerebrosidase would show a 2:1 distribution of the two possible isomers. To avoid this, the functional group at C-3 of the C12-ceramide is protected with a benzoyl group. Accordingly, the following route of synthesis is preferred. The overall synthesis scheme for the ABG substrate is shown below:

SCHEME 1

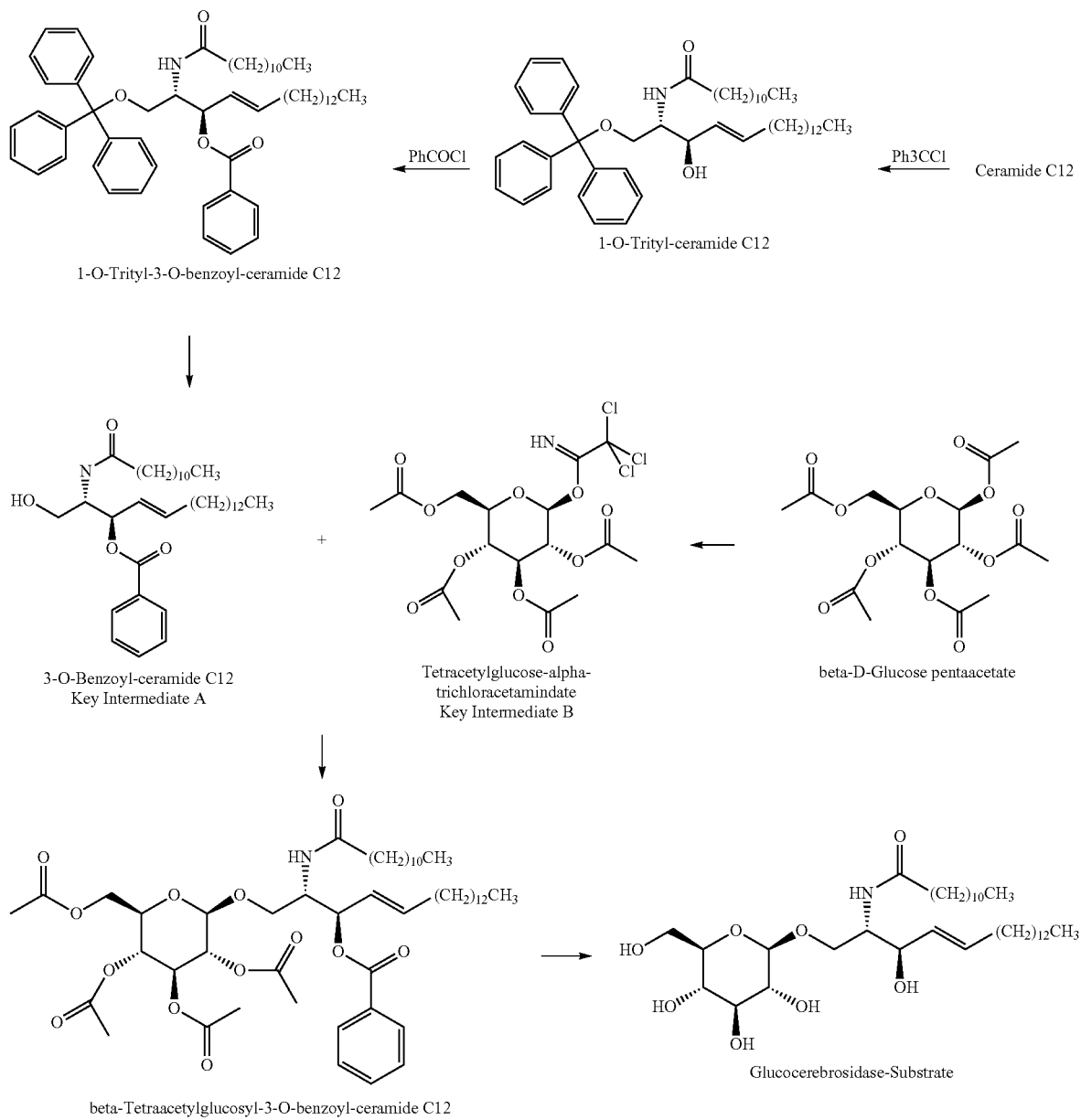

As outlined in the scheme, the two components 3-O-benzoyl-ceramide C12 (Key intermediate A) and 2,3,4,6-tetra-O-acetyl-α-D-glucopyranosyl-trichloracetamidate (Key intermediate B) are key to the synthesis of the ABG substrate. Key intermediate A is accessible from ceramide C12 by a 2-step protection reaction with tri-tylchloride and benzoylchloride, followed by cleavage of the trityl-protection group using P-toluenesulfonic acid. Key intermediate B is accessible from β-D-glucose penta-acetate by reaction with hydrazine acetate and trichloroacetonitrile.

The sugar configuration on the substrate is preferably beta-linked glucose. Substrates that have multiple sugar configurations will be converted to product by additional enzymes. Thus, the activity of a second enzyme would mask the deficiency of ABG and result in a false negative result. The beta-linked glucose is clearly discernible from the alpha-linked glucose using $^1$H-NMR analysis (H–α—5.5 ppm chemical shift, H–β=4.9 ppm chemical shift). The product must be essentially absent from the substrate, and can be clearly discerned from the substrate in HPLC. Separation of both substances is therefore efficiently possible during column chromatography applied in the process due to the significantly different polarity.

For the second ABG assay described herein, the substrate is preferably a fluorogenic substrate such as 4-MU-β-Glu. 4-MU-β-Glu can be obtained from commercial sources such as Sigma Chemical Company (Cat. no. M3633). Other substrates useful in the second ABG assay include 4-pentafluoroethylumbelliferyl-beta-D-glucoside, 4-trifluoromethylumbelliferyl-beta-D-glucoside, and 4-heptylumbelliferyl-beta-D-glucoside. Preferably, the substrate is 4-methylumbelliferyl-β-D-glucopyranoside (4-MU-β-Glu).

The internal standard for the ABG assay mix can be purchased from a commercial supplier. The commercially available ceramide is obtained fully synthetically, which assures a high degree of accuracy of the structure including the resulting fatty acid chain length. The synthesis principle for the C14 ceramide (ABG internal standard) is shown below:

assures a high degree of accuracy of the structure including the resulting fatty acid chain length. The synthesis principle for the C6 sphingomyelin is shown below.

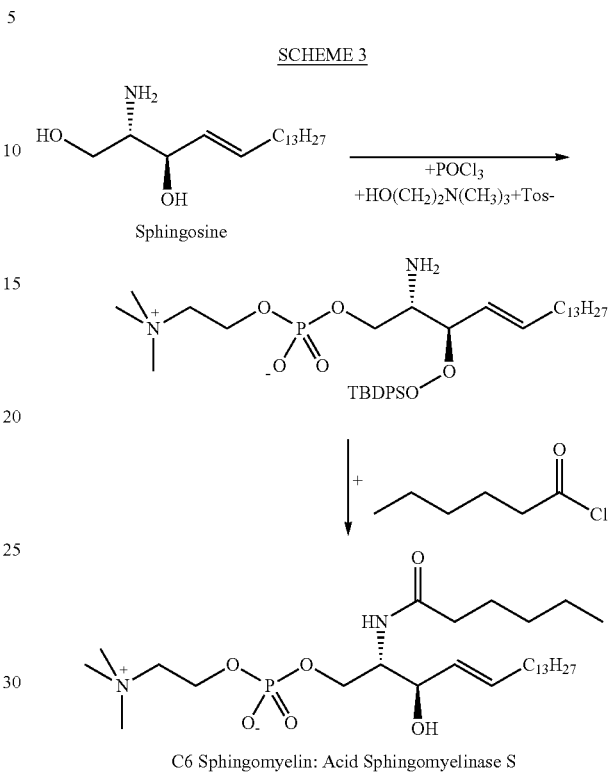

SCHEME 3

C6 Sphingomyelin: Acid Sphingomyelinase S

The product must be essentially absent from the substrate, and can be clearly discerned from the substrate in HPLC and a separation of both substances is efficiently possible during

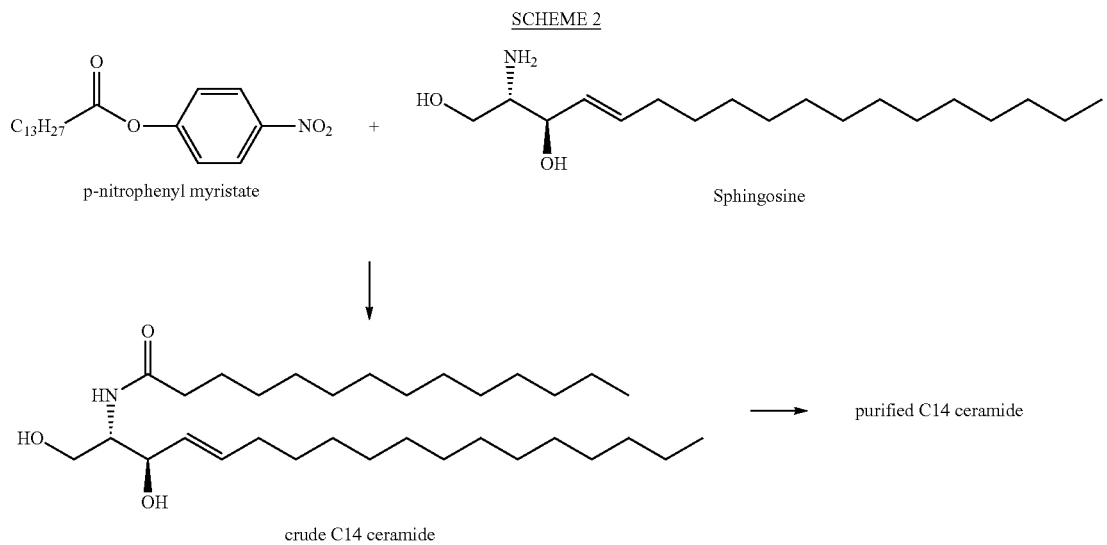

SCHEME 2 p-nitrophenyl myristate

Sphingosine crude C14 ceramide purified C14 ceramide

ASM Substrate/Internal Standard Synthesis

The substrate for the Niemann-Pick A/B assay (ASM-S) can be purchased from a supplier such as Avanti Polar Lipids. The sphingomyelin is obtained fully synthetically, which the column chromatography applied in the process due to the significantly different polarity.

The internal standard for the ASM assay can also be purchased from a commercial supplier. The ceramide is obtained fully synthetically, which assures a high degree of accuracy of the internal standard structure including the resulting fatty acid chain length. The synthesis principle for the C4 ceramide internal standard is shown below.

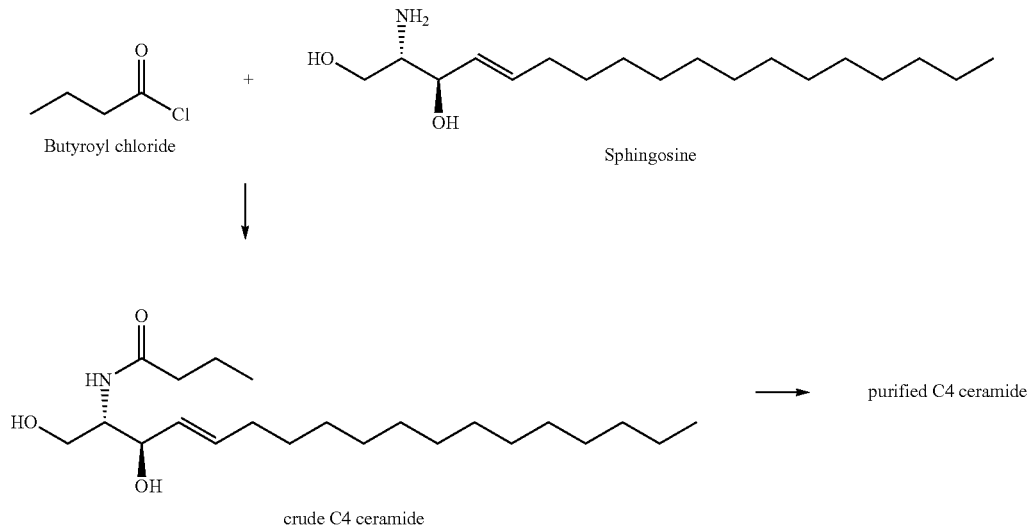

SCHEME 4

Butyroyl chloride + Sphingosine crude C4 ceramide → purified C4 ceramide

GAA Substrate/Internal Standard Synthesis

The current synthesis strategy is based on condensation of the two key intermediates as shown below. One alternate route would be the glycosylation of the corresponding intermediate without the sugar moiety (7-$d_5$-Benzoylamino-heptyl)-[2-(4-hydroxyphenyl-carbamoyl)-ethyl]-carbamic acid tertbutyl ester also defined as GAA-P. This alternate route is shown as follows:

If this route is used, the potential impurities in the substrate would include the product along with the sugar (glucose for GAA-S). Therefore the level of the impurity GAA-P could possibly adulterate the test since it would not be possible differentiate the level of product deriving from the synthesis compared to the level deriving from enzyme reaction. For this reason the route of synthesis described below is preferred route of synthesis is most appropriate for the production of these components.

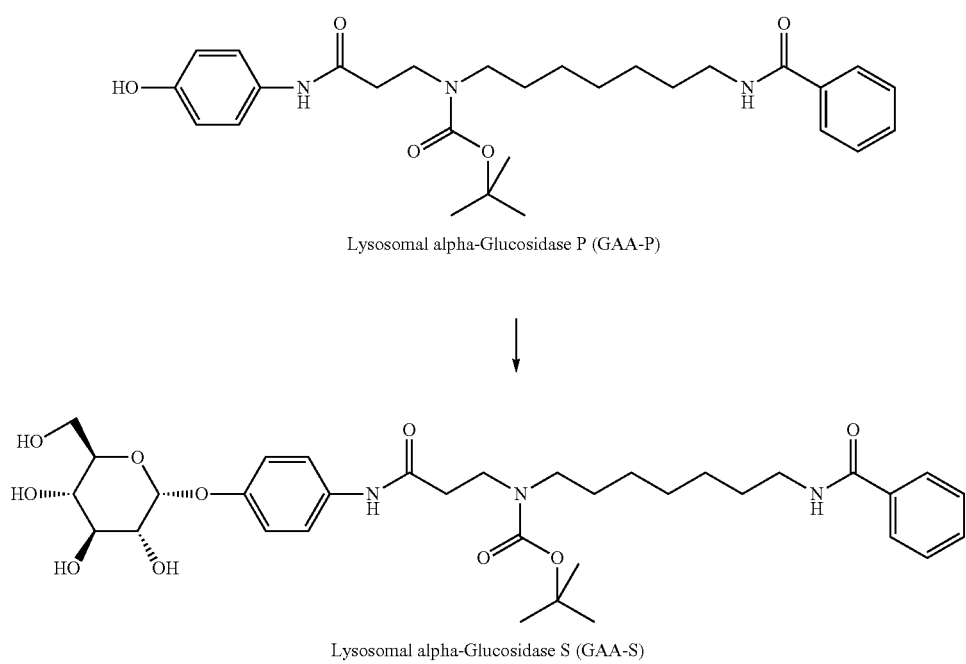

SCHEME 5

Lysosomal alpha-Glucosidase P (GAA-P)

Lysosomal alpha-Glucosidase S (GAA-S)

The overall synthesis of the GAA substrate is shown as follows:

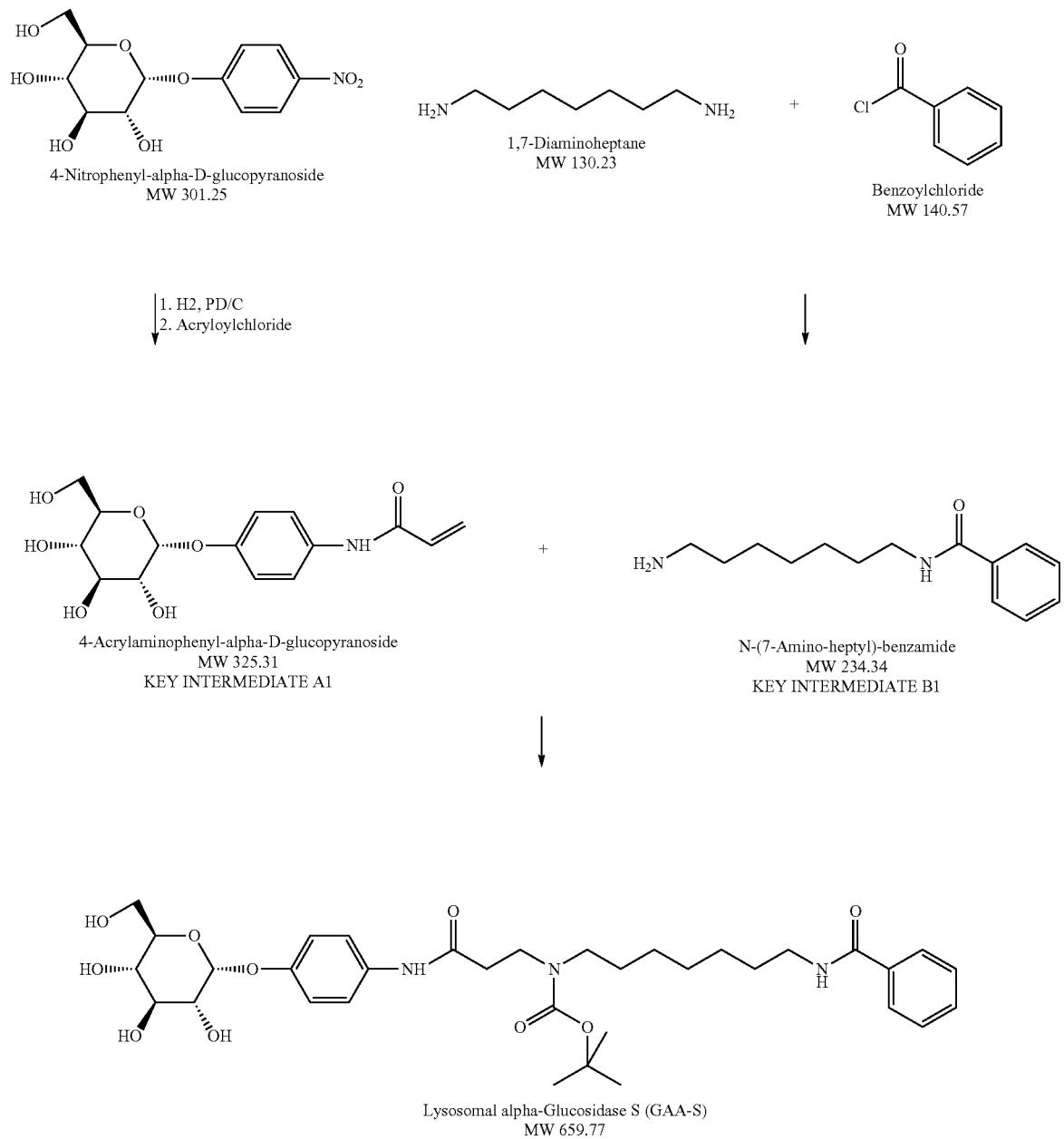

SCHEME 6

As outlined in the scheme, the two components 4-Acrylaminophenyl-α-D-glucopyranoside (Key intermediate A1) and N-(7-Amino-heptyl)-benzamide (Key intermediate B1) are defined to be key intermediates. Key intermediate A1 is easily accessible by reduction of the starting material 4-Nitrophenyl-α-D-glucopyranoside followed by reaction with acryloylchloride. Key intermediate B1 is synthesized by coupling 1,7-diaminoheptane with benzoyl chloride to obtain an amide bond.

The sugar configuration on the substrate must be alpha-linked glucose. Substrates that have multiple sugar configurations will be converted to product by additional lysosomal enzymes; the activity of a second lysosomal enzyme will mask the deficiency of GAA and result in a false negative result. The Alpha-linked glucose is clearly discernible from the beta linked glucose using $^1$H-NMR-analysis (H–α=5.63 ppm chemical shift, H–β=5.09 ppm chemical shift). The distinction between glucose and galactose can be done by HPLC analysis (1 minute difference in retention time) and 1D or 2D NMR.

The following reaction scheme shows the process principles of the GAA-internal standard synthesis

SCHEME 7

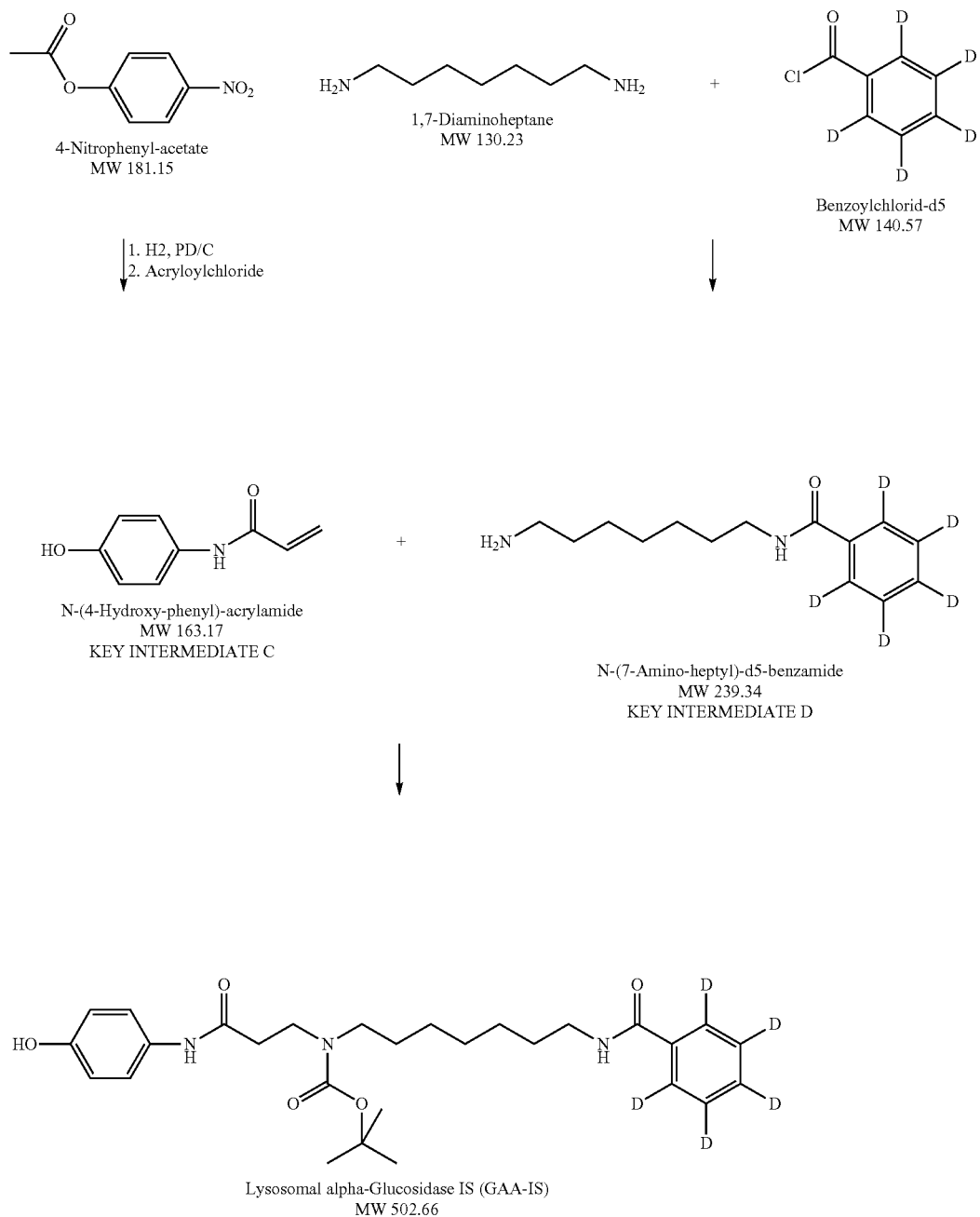

As outlined in the scheme, the two components N-(4-Hydroxy-phenyl)-acrylamide (Starting Material C) and N-(7-Amino-heptyl)-d5-benzymide (Starting Material D) are defined to be key intermediates from a process qualification perspective and represent the starting point of the process qualification. Key intermediate C is easily accessible by reduction of the starting material 4-Nitrophenylacetate followed by reaction with acryloylchloride. The acetyl is then saponified using sodium methylate in methanol. Key intermediate D is synthesized by coupling 1,7-diaminoheptane with benzoyl chloride-d5 leading to the corresponding amide, at similar reaction conditions as for key intermediate B1.

A more detailed description of an example of GAA substrate and internal standard synthesis is provided in Example 1.

GLA Substrate/Internal Standard Synthesis

The synthesis strategy is based on the condensation of two key intermediates as shown below. One other potential route for synthesis would be the glycosylation of the corresponding intermediate without the sugar moiety (6-$d_5$-benzoylamino-hexyl)-[2-(4-hydroxy-phenyl-carbamoyl)-ethyl]-carbamic acid tertbutyl ester (i.e., the GLA assay product). This alternate synthesis route is shown as follows:

SCHEME 8

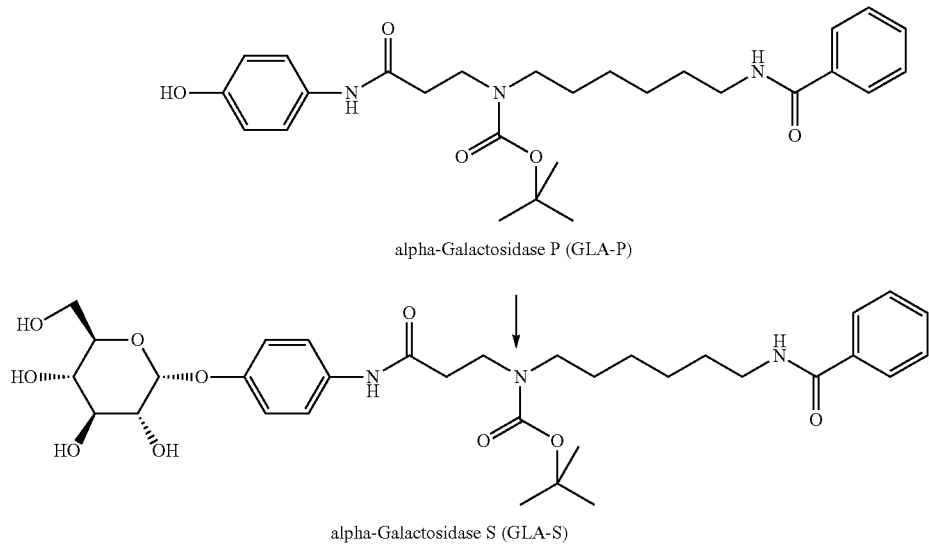

alpha-Galactosidase P (GLA-P)

alpha-Galactosidase S (GLA-S)

If this route would have been used, the potential impurities in the substrate would have been the product along with the sugar (galactose for GLA substrate). Therefore the level of the impurity (the GLA assay product) could possibly adulterate the test since it would not be possible to differentiate the level of product deriving from the synthesis compared to the level deriving from the enzyme reaction. For this reason, the following synthesis route is preferred as the most appropriate method for the production of GLA substrate and internal standard. The general synthesis scheme for the GLA substrate is as follows:

SCHEME 9

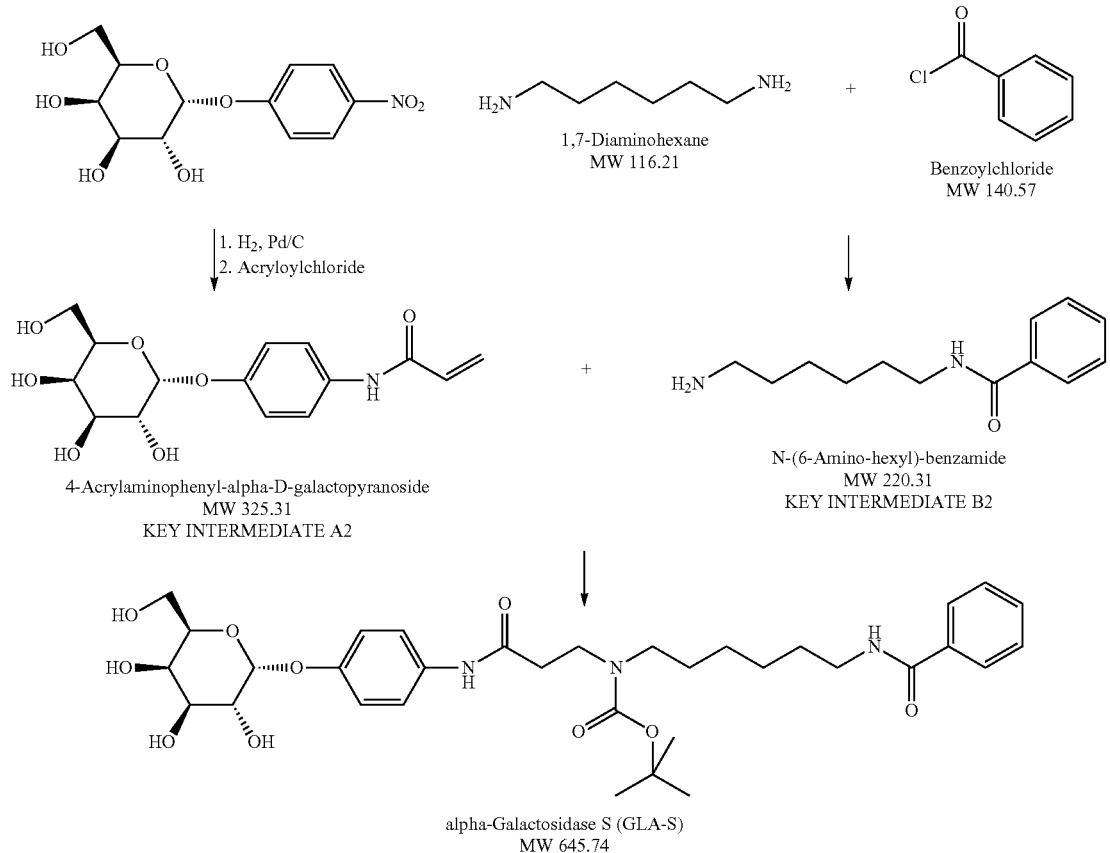

As outlined in the above scheme, the two components 4-acrylaminophenyl-α-D-galactopyranoside (key intermediate A2) and N-(6-amino-hexyl)-benzamide (key intermediate B2) are defined to be key intermediates. Key intermediate A2 is readily accessible by reduction of the starting material 4-Nitrophenyl-α-D-galactopyranoside followed by reaction with acryloylchloride. Intermediate B2 is synthesized by coupling 1,6-diaminohexane with benzoyl chloride to obtain an amide bond.

The sugar configuration on the substrate must be alpha-linked galactose. Substrates that have multiple sugar configurations will be converted to product by additional lysosomal enzymes, and the activity of a second lysosomal enzyme will mask the deficiency in GLA activity and result in false negative results. The alpha-linked galactose is clearly discernible from the beta linked galactose using $^1$H-NMR analysis (H–α=5.63 ppm chemical shift, H–β=5.09 ppm chemical shift). The distinction between glucose and galactose can be done by HPLC analysis (1 minute difference in retention time) and 1D or 2D NMR. In addition, if product is already present in the substrate, it may lead to false positive results. The product is clearly discernible from substrate in HPLC and a separation of both substances is efficiently possible during the column chromatography applied in the process due to the significantly different polarity.

The following reaction scheme shows the process of production of the GLA internal standard:

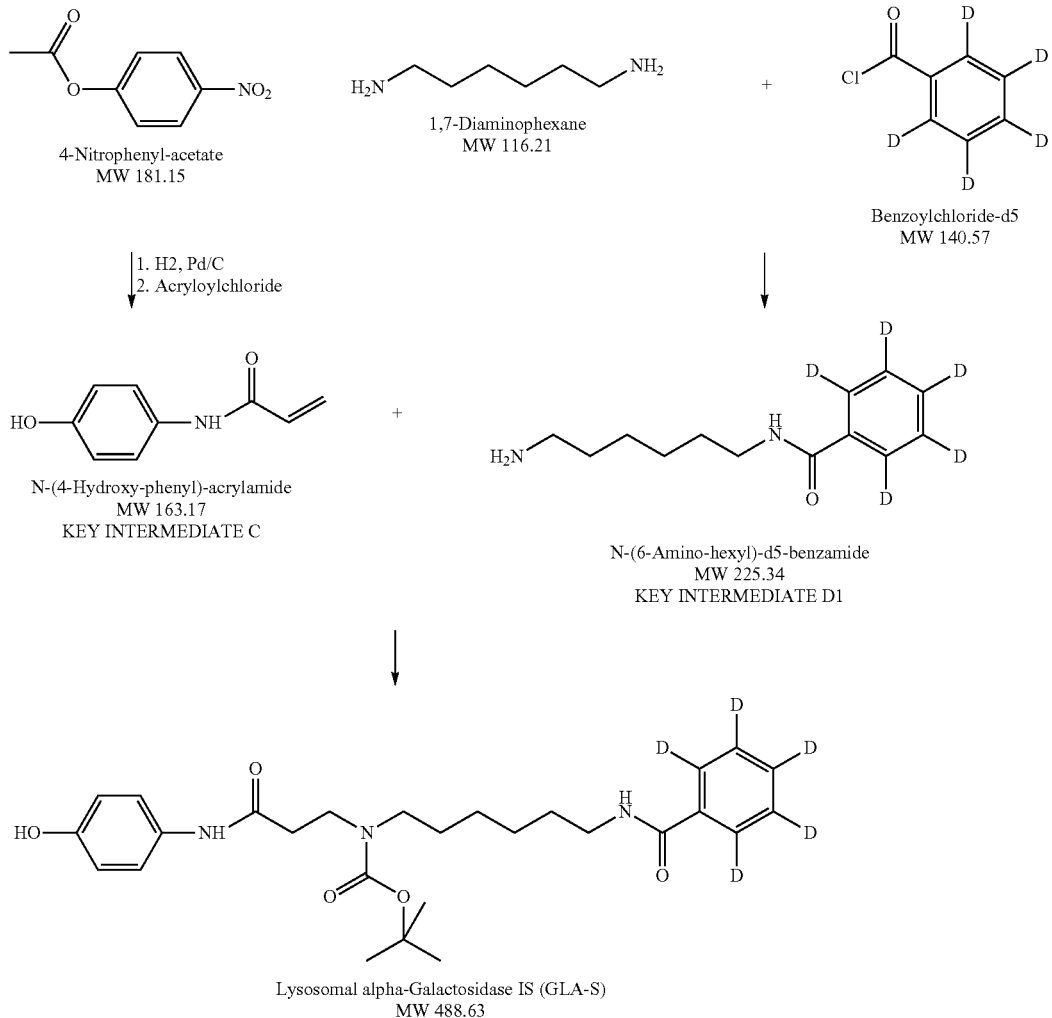

SCHEME 10

As outlined in the scheme, the two components N-(4-hydroxy-phenyl)-acrylamide (key intermediate C) and N-(6-amino-hexyl)-d5-benzamide (key intermediate D1) are defined to be key intermediates. Key intermediate C is easily accessible by reduction of the starting material 4-nitrophenyl-acetate followed by reaction with acryloylchloride. The acetyl group is then saponified using sodium methylate in methanol. Key intermediate D1 is synthesized by coupling 1,6-diaminohexane with benzoyl chloride-d5 leading to the corresponding amide, at similar reaction conditions as for key intermediate B1.

A more detailed description of an example of GLA substrate and internal standard synthesis is provided in Example 1.

GALC Substrate/Internal Standard Synthesis

The current synthesis strategy is based on condensation of the two key intermediates and a subsequent de-protection step using sodium-methylate. An alternate synthesis route would be the direct galactosylation of the C8-ceramide (the GALC reaction product) as shown below:

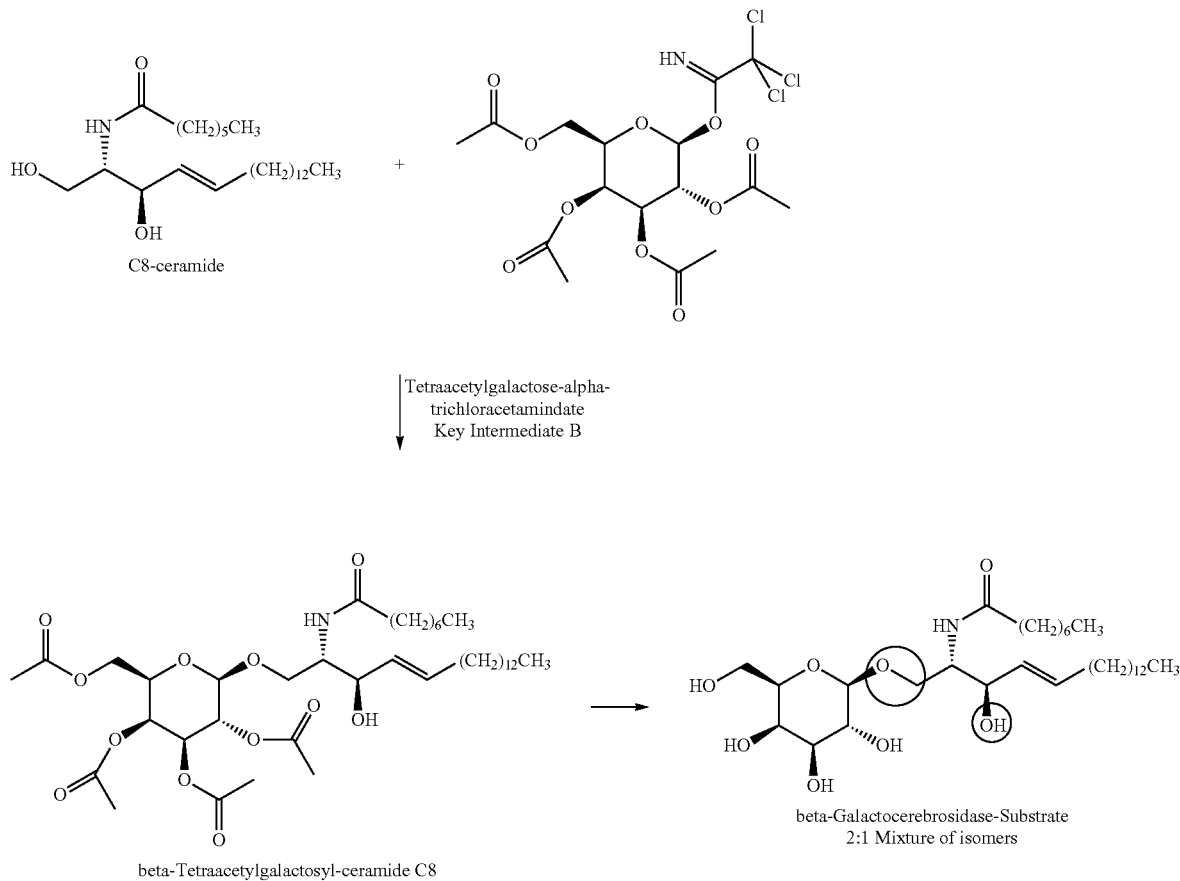

If this synthesis method is used, however, the resulting β-galactocerebrosidase (GALC substrate) would show a 2:1 distribution of the two possible isomers. To avoid this scenario, the functional group at C-3 of the C8-ceramide would have to be protected with a benzoyl-group. Accordingly, the preferred synthesis scheme is shown as follows:

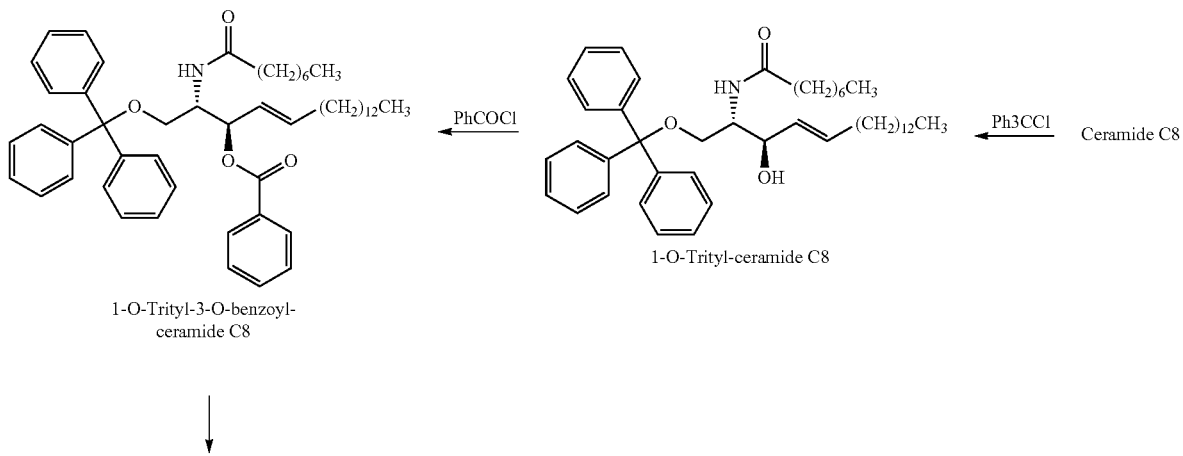

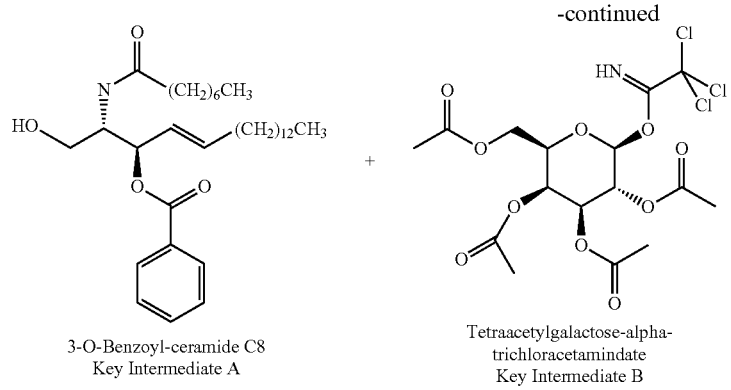

3-O-Benzoyl-ceramide C8
Key Intermediate A

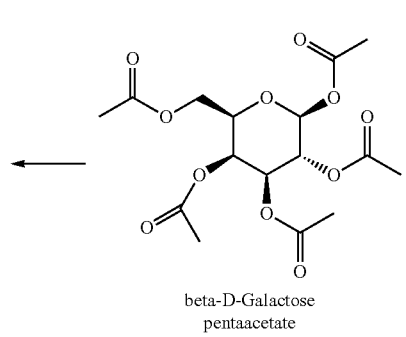

Tetraacetylgalactose-alpha-trichloracetamindate
Key Intermediate B beta-D-Galactose pentaacetate

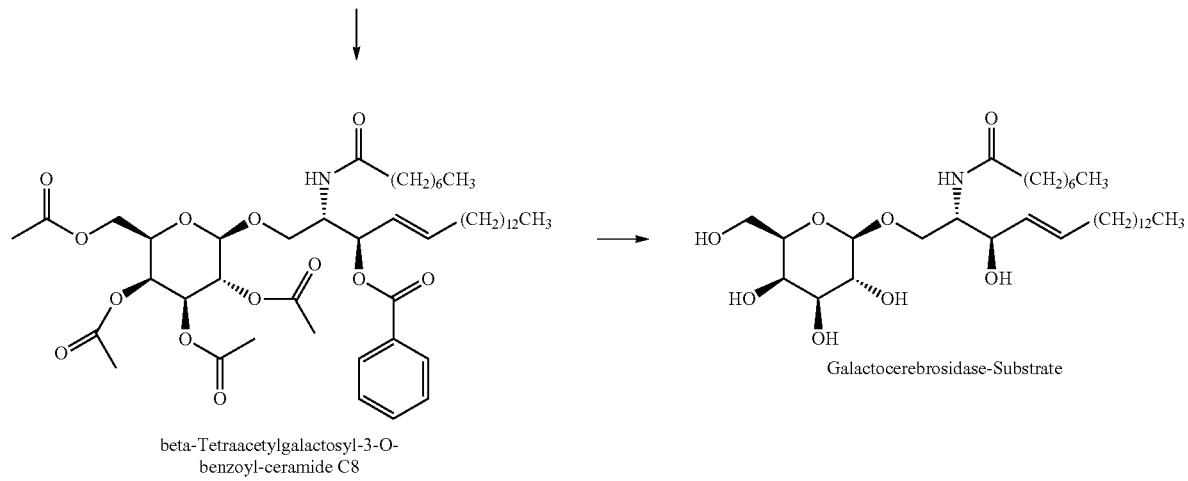

beta-Tetraacetylgalactosyl-3-O-benzoyl-ceramide C8

Galactocerebrosidase-Substrate

As outlined in the above scheme, the two components 3-O-benzoyl-ceramide C8 (key intermediate A) and 2,3,4,6-tetra-O-acetyl-α-D-galactopyranosyl-trichloracetamidate (key intermediate B) are defined to be key intermediates. Key intermediate A is accessible from ceramide C8 by a 2-step protection reaction with trityl-chloride and benzoylchloride, followed by cleavage of the trityl-protection group using p-toluenesulfonic acid. Key intermediate B is accessible from β-D-galactose penta-acetate by reaction with hydrazine acetate and trichloroacetonitrile.

The sugar configuration on the substrate is preferably beta-linked galactose. Substrates that have multiple sugar configurations will be converted to product by additional enzymes. Thus, the activity of a second enzyme would mask the deficiency of GALC and result in a false negative result. The beta-linked galactose is clearly discernible from the alpha-linked galactose using $^1$H-NMR analysis (H–α—5.5 ppm chemical shift, H–β=4.9 ppm chemical shift). The product must be essentially absent from the substrate, and can be clearly discerned from the substrate in HPLC. Separation of both substances is therefore efficiently possible during column chromatography applied in the process due to the significantly different polarity.

The internal standard for the GALC assay can be purchased from a commercial supplier such as Avanti Polar Lipids. The ceramide can be obtained fully synthetically, which assures a high degree of accuracy of the structure including the resulting fatty acid chain length. The synthesis principle for the GALC internal standard is as follows:

SCHEME 13

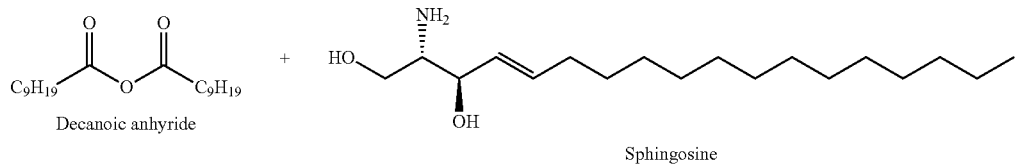

Decanoic anhyride    Sphingosine

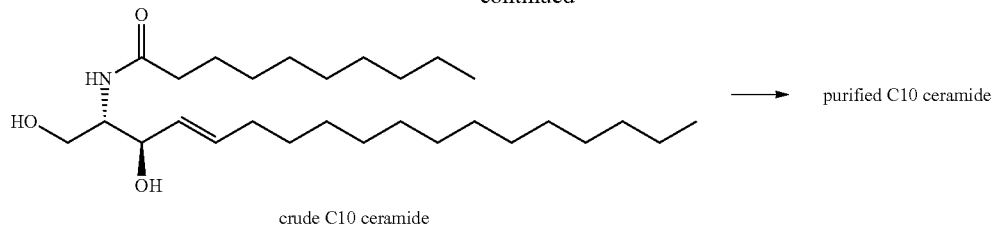

→ purified C10 ceramide crude C10 ceramide

The following section outlines the identity and concentrations of the various components of the five lysosomal enzyme activity assays of the invention.

ABG Assay Mix

In one embodiment, the invention provides a first assay to determine the activity of ABG, a deficiency of which is the cause of Gaucher disease. The assay is performed by combining either a 3.2 mm punch out from a dried blood spot (DBS; described in further detail below) or DBS punch extract with an assay mix comprising substrate, internal standard, detergent and buffer. Preferably the assay is performed using DBS punch extract.

The substrate used to assess ABG enzyme activity is D-Glucosyl-β1-1'-N-dodecanoyl-D-erythro-sphingosine (C12 glucosyl ceramide; $C_{36}H_{69}NO_8$) and is present in the assay mix at a concentration of between 0.3 and 0.9 mM, preferably at a concentration of 0.6 mM, and still more preferably at a concentration of 0.67 mM. The internal standard for the ABG assay is N-myristoyl-D-erythro-sphingosine (C14 ceramide; $C_{32}H_{63}NO_3$), and is present in the mix at a concentration of between 6.5 and 19.5 μM, preferably at a concentration of 13 μM, and still more preferably at a concentration of 13.33 μM. The detergent for the ABG assay is sodium taurocholate, present in the assay mix at a concentration of between 8 and 24 g/L, preferably at a concentration of 16 g/L. The buffer for the ABG assay is a phosphate/citrate buffer at a concentration of between about 0.3 and 0.9 M, preferably at a concentration of 0.6 M, and still more preferably at a concentration of 0.62 M. The ABG assay mix should be at a pH of between 5 and 5.2, preferably pH 5.1.

To perform the first ABG assay (described in further detail below) 10-20 μl, preferably 13-17 μl, and more preferably 15 μl of the ABG assay mix is combined with 10 μl of the DBS punch extract. Since, as noted above, the DBS punch contains 2-3.5 μl blood and is preferably extracted in 70 μl buffer, each ABG assay reaction will contain between 0.25 and 0.58 μl blood. Preferably, each assay will contain between 0.33 and 0.43 μl blood, and more preferably will contain 0.4 μl blood. The DBS punch or punch extract is reacted with the ABG assay mix according to the steps described herein below. During the reaction, however, the concentration of substrate in the assay is between 0.2 and 0.6 mM, preferably 0.3 and 0.5 mM, and more preferably 0.4 mM.

In addition to the absolute concentrations of assay mix components described above, the invention contemplates that the ratio of assay components to the amount of substrate in the mix is an important factor for optimizing the assay reaction. Accordingly, to assay for ABG activity the ratio of substrate to internal standard is about 50:1, and in a preferred embodiment is 50:1. The ratio of detergent to substrate in the ABG assay mix is about 45:1, and in a preferred embodiment, is 45:1. The ratio of buffer to substrate is about 925:1, and in a preferred embodiment, is 925:1.

In one embodiment, the invention provides a second assay to determine the activity of ABG, a deficiency of which is the cause of Gaucher disease. The assay is performed by combining either a 3.2 mm punch from a dried blood spot (DBS; described in further detail below) or, preferably, DBS punch extract with an assay mix comprising substrate, a β-glucosidase inhibitor, detergent and buffer.

The substrate used to assess ABG enzyme activity in the second assay is 4-Methylumbelliferyl-β-D-glucopyranoside (4-MU-β-Glu), and is present in the assay mix at a concentration in the range of 5 to 10 mM, preferably at a concentration of about 8 mM, and more preferably at a concentration of 8.333 mM. The detergent for the second ABG assay is preferably sodium taurodeoxycholate, present in the reaction at a concentration in the range of 1 to 12 mM, preferably at a concentration of 6 mM. Importantly, the impurities in the sodium taurodeoxycholate must be kept to a minimum, because impurities can precipitate and affect the precision of the assay. Thus, it is preferred that the sodium taurodeoxycholate be at least 90% pure, preferably 95, 97, 98, 99, or up to 100% pure. Most preferably, the sodium taurodeoxycholate used in the reaction mix is at least 97% pure.

In addition to the foregoing, the second ABG assay utilizes the specific ABG inhibitor, conduritol B epoxide (CBE; Calbiochem Product No. 234599). Use of an ABG-specific inhibitor permits an evaluation of the contribution of other β-glucosidase enzymes to the overall activity of the assay. The difference between activities in the absence and presence of CBE is used to quantitate ABG activity.

More specifically, the second ABG assay utilizes the following assay components:

Substrate Stock Solution, 1 M: 774.26 mg of 4-MU-β-Glu in 2.29 mL DMSO

Buffered Extractant: 0.30 M citrate phosphate with 1% sodium taurodeoxycholate and 1% triton X-100, pH 5.2

CBE Stock Solution: 8.30 mg conduritol B epoxide in 200 μL of DMSO.

4-MU Stock Solution, 25 mM. (Used for standard curve): 5 mg of 4-MU in 1.14 mL DMSO Stop Buffer: 0.5 M EDTA, pH 11.3 to 12.0.

Uninhibited Working Substrate Solution: 100 μl Substrate Stock Solution plus 7.9 ml pure water Inhibited Working Substrate Solution: 7.5 μL of 0.26 M CBE+4 ml of Uninhibited Working Substrate Solution To perform the second ABG assay, a 3 mm DBS is first extracted in an extraction buffer containing a detergent, preferably sodium taurodeoxycholate (described further below). The extracted DBS is then divided into at least two samples. The first sample is mixed with the inhibited working substrate solution, and the second sample is mixed with the uninhibited working substrate solution. The reaction mixtures are then incubated for 10-30 hours, preferably 15-25, still more preferably 20 hours at 35-39° C., preferably 37° C. After the allotted time, the reactions are quenched by the addition of stop buffer (0.5M EDTA at pH 11.3-12). The reaction mixtures are then centrifuged for 30-90 minutes, preferably 60 minutes, at 2000-3000 rpm, preferably 2500 rpm. The amount of product generated (amount of 4-MU present) in the reaction mixtures is then measured using a fluorometer with 355 nm excitation and 460 nm emission wavelengths.

The amount of ABG enzyme activity is determined using the second assay by subtracting the amount of product generated (amount of 4-MU present) in the first reaction mixture (containing the inhibited working substrate solution) from the second reaction mixture (containing the uninhibited working substrate solution) to produce a differential fluorescence signal. As used herein, a "differential fluorescence signal" refers to the difference between the amount of product generated in a reaction mix using the inhibited working substrate solution and the amount of product generated in a reaction mix using the uninhibited working substrate solution, and is attributable to the level of fluorescence in the uninhibited working substrate reaction that is contributed by the ABG enzyme activity. The differential fluorescence signal is then compared to a standard curve to determine the enzyme activity.

The standard curve can be generated along with the ABG assay reactions, or can be determined separately. To prepare the standard curve, a 12.5 µM 4-Methlyumbelliferone (4-MU) solution is prepared. This solution is then serially diluted to the following concentrations of 4-MU: 750 pM, 375 pM, 188 pM, 93.8 pM, 46.9 pM, 23.4 pM, 11.7 pM, and 0 pM. One of skill in the art will appreciate that a different serial dilution may be used, and the remainder of the calculations adjusted accordingly. The individual fluorescence readings from the standard curve samples are then plotted against the corresponding molar quantity per sample. The equation (4-MU, pmol)=α×fluorescence is then fit to the data, wherein α is the slope of the regression line. The differential fluorescence levels measured above are then converted into pmol per sample by linear regression using the standard curve. This result is then converted into pmol/(punch*h) (pmol substrate converted per 3.2 mm punch per hour) by dividing the result (i.e., the total pmol per sample found in each reaction using the standard curve) by the incubation time in hours and multiplying by the fraction of extract used per reaction.

ASM Assay Mix

In one embodiment, the invention provides an assay to determine the activity of ASM, a deficiency of which is the cause of Niemann-Pick A/B disease. The assay is performed by combining either a DBS punch or DBS punch extract with an assay mix comprising substrate, internal standard, detergent and buffer. Preferably the assay is performed using DBS punch extract.

The substrate used to determine ASM enzyme activity is N-Hexanoyl-D-erythro-sphingosylphosphorylcholine (C6-sphingomyelin; $C_{29}H_{59}N_2O_6P$) and is present in the assay mix at a concentration of between 0.15 and 0.45 mM, preferably at a concentration of 0.3 mM, and still more preferably at a concentration of 0.33 mM. The internal standard for the ASM assay is N-butyroyl-D-erythro-sphingosine (C4-ceramide; $C_{22}H_{43}NO_3$), and is present in the mix at a concentration of between 3.0 and 9.0 µM, preferably at a concentration of 6 µM, and still more preferably at a concentration of 6.67 µM. The detergent for the ASM assay is sodium taurocholate, present in the assay mix at a concentration of between 0.5 and 1.5 g/L, preferably at a concentration of 1 g/L. The buffer for the ASM assay is a sodium acetate buffer at a concentration of between about 0.45 and 1.3 M, preferably at a concentration of 0.9 M, and still more preferably at a concentration of 0.92 M. In addition, the ASM assay mix includes the enzyme co-factor zinc chloride at a concentration of between 0.5 and 1.5 mM, preferably at a concentration of 0.6 mM. The ASM assay mix should be at a pH of between 5.5 and 5.9, preferably pH 5.7.

To perform the ASM assay (described in further detail below) 10-20 µl, preferably 13-17 µl, and more preferably 15 µl of the ASM assay mix is combined with 10 µl of the DBS punch extract. Since, as noted above, the DBS punch contains 2-3.5 µl blood and is preferably extracted in 70 µl buffer, each ASM assay reaction will contain between 0.25 and 0.58 µl blood. Preferably, each assay will contain between 0.33 and 0.43 µl blood, and more preferably will contain 0.4 µl blood. The DBS punch or punch extract is reacted with the ASM assay mix according to the steps described herein below. During the reaction, however, the concentration of substrate in the assay is between 0.1 and 0.3 mM, preferably 0.15 and 0.25 mM, and more preferably 0.2 mM.

In addition to the absolute concentrations of assay mix components described above, the invention contemplates that the ratio of assay components to the amount of substrate in the mix is an important factor for optimizing the assay reaction. Accordingly, to assay for ASM activity the ratio of substrate to internal standard is about 50:1, and in a preferred embodiment is 50:1. The ratio of detergent to substrate in the ASM assay mix is about 5.6:1, and in a preferred embodiment, is 5.6:1. The ratio of buffer to substrate is about 2788:1, and in a preferred embodiment, is 2788:1. The ratio of zinc chloride to substrate is about 1.82:1, and in a preferred embodiment, is 1.82:1.

GAA Assay Mix

In one embodiment, the invention provides an assay to determine the activity of GAA, a deficiency of which is the cause of Pompe disease. The assay is performed by combining either a DBS punch or DBS punch extract with an assay mix comprising substrate, internal standard, detergent and buffer. Preferably the assay is performed using DBS punch extract.

The substrate used to determine GAA enzyme activity is (7-benzoylamino-heptyl)-{2-[4-(3,4,5-trihydroxy-6-hydroxymethyl-tetrahydro-pyran-2-yloxy)-phenylcarbamoyl]-ethyl}-carbamic acid tert-butyl ester ($C_{34}H_{49}N_2O_{10}$) and is present in the assay mix at a concentration of between 0.3 and 0.9 mM, preferably at a concentration of 0.6 mM, and still more preferably at a concentration of 0.667 mM. The internal standard for the GAA assay is 7-d5-benzoylamino-heptyl)-[2-(4-hydroxy-phenylcarbamoyl)-ethyl]-carbamic acid tert-butyl ester ($C_{28}H_{34}N_3O_5D_5$), and is present in the mix at a concentration of between 3.3 and 9.9 µM, preferably at a concentration of 6 µM, and still more preferably at a concentration of 6.67 µM. The detergent for the GAA assay is CHAPS, present in the assay mix at a concentration of between 5 and 15 g/L, preferably at a concentration of 10 g/L. The buffer for the GAA assay is a phosphate citrate buffer at a concentration of between about 0.15 and 0.45 M, preferably at a concentration of 0.3 M. In addition, the GAA assay mix includes the non-specific enzyme inhibitor acarbose at a concentration of between about 6.5 and 19.5 µM, preferably at a concentration of 13.3 µM. The GAA assay mix should be at a pH of between 3.8 and 4.2, preferably pH 4.0.

To perform the GAA assay (described in further detail below) 10-20 µl, preferably 13-17 µl, and more preferably 15 µl of the GAA assay mix is combined with 10 µl of the DBS punch extract. Since, as noted above, the DBS punch contains 2-3.5 µl blood and is preferably extracted in 70 µl buffer, each GAA assay reaction will contain between 0.25 and 0.58 µl blood. Preferably, each assay will contain between 0.33 and 0.43 µl blood, and more preferably will contain 0.4 µl blood. The DBS punch or punch extract is reacted with the GAA assay mix according to the steps described herein below. During the reaction, however, the concentration of substrate in the assay is between 0.2 and 0.6 mM, preferably 0.3 and 0.5 mM, and more preferably 0.4 mM.

In addition to the absolute concentrations of assay mix components described above, the invention contemplates that the ratio of assay components to the amount of substrate in the mix is an important factor for optimizing the assay reaction. Accordingly, to assay for GAA activity the ratio of substrate to internal standard is about 100:1, and in a preferred embodiment is 100:1. The ratio of detergent to substrate in the GAA assay mix is about 24.3:1, and in a preferred embodiment, is 24.3:1. The ratio of buffer to substrate is about 450:1, and in a preferred embodiment, is 450:1. The ratio of inhibitor (acarbose) to substrate is about 0.02:1, and in a preferred embodiment, is 0.02:1.

GLA Assay Mix

In one embodiment, the invention provides an assay to determine the activity of GLA, a deficiency of which is the cause of Fabry disease. The assay is performed by combining either a DBS punch or DBS punch extract with an assay mix comprising substrate, internal standard, detergent and buffer. Preferably the assay is performed using DBS punch extract.

The substrate used to determine GLA enzyme activity is (6-Benzoylamino-hexyl)-{2-[4-(3,4,5-trihydroxy-6-hydroxymethyl-tetrahydro-pyran-2-yloxy)-phenylcarbamoyl]-ethyl}-carbamic acid tert-butyl ester ($C_{33}H_{47}N_3O_{10}$) and is present in the assay mix at a concentration of between 1.5 and 4.5 mM, preferably at a concentration of 3.0 mM, and still more preferably at a concentration of 3.33 mM. The internal standard for the GLA assay is 6-d5-Benzoylamino-hexyl)-[2-(4-hydroxy-phenylcarbamoyl)-ethyl]-carbamic acid tert-butyl ester ($C_{27}H_{32}N_3O_5D_5$), and is present in the mix at a concentration of between 3.3 and 9.9 µM, preferably at a concentration of 6 µM, and still more preferably at a concentration of 6.67 µM. The detergent for the GLA assay is sodium taurocholate present in the assay mix at a concentration of between 2 and 4 g/L, preferably at a concentration of 3 g/L. The buffer for the GLA assay is a sodium acetate buffer at a concentration of between about 0.07 and 0.21 M, preferably at a concentration of 0.142 M. In addition, the GLA assay mix includes the non-specific enzyme inhibitor N-acetylgalactosamine at a concentration of between about 80 and 240 µM, preferably at a concentration of 160 mM. The GLA assay mix should be at a pH of between 4.4 and 4.8, preferably pH 4.6.

To perform the GLA assay (described in further detail below) 10-20 µl, preferably 13-17 µl, and more preferably 15 µl of the GLA assay mix is combined with 10 µl of the DBS punch extract. Since, as noted above, the DBS punch contains 2-3.5 µl blood and is preferably extracted in 70 µl buffer, each GLA assay reaction will contain between 0.25 and 0.58 µl blood. Preferably, each assay will contain between 0.33 and 0.43 µl blood, and more preferably will contain 0.4 µl blood. The DBS punch or punch extract is reacted with the GLA assay mix according to the steps described herein below. During the reaction, however, the concentration of substrate in the assay is between 1.0 and 1.5 mM, and preferably at a concentration of 2.0 mM.

In addition to the absolute concentrations of assay mix components described above, the invention contemplates that the ratio of assay components to the amount of substrate in the mix is an important factor for optimizing the assay reaction. Accordingly, to assay for GLA activity the ratio of substrate to internal standard is about 499:1, and in a preferred embodiment is 499:1. The ratio of detergent to substrate in the GLA assay mix is about 1.68:1, and in a preferred embodiment, is 1.68:1. The ratio of buffer to substrate is about 43:1, and in a preferred embodiment, is 43:1. The ratio of inhibitor (N-acetylgalactosamine) to substrate is about 48:1, and in a preferred embodiment, is 48:1.

GALC Assay Mix

In one embodiment, the invention provides an assay to determine the activity of GALC, a deficiency of which is the cause of Krabbe disease. The assay is performed by combining either a DBS punch or DBS punch extract with an assay mix comprising substrate, internal standard, detergent and buffer. Preferably the assay is performed using a DBS punch, that is, there is no blood extraction step, and the 3.2 mm DBS punch is placed in direct contact with the assay mix described below.

The substrate used to determine GALC enzyme activity is D-galactosyl-β1-1'-octanoyl-D-erythro-sphingosine (C8 galactosyl ceramide; $C_{32}H_{61}NO_8$) and is present in the assay mix at a concentration of between 0.5 and 1.5 mM, preferably at a concentration of 1 mM. The internal standard for the GALC assay is N-decanoyl-D-erythro-sphingosine (C10 ceramide; $C_{28}H_{55}NO_3$), and is present in the mix at a concentration of between 3.3 and 9.9 µM, preferably at a concentration of 6 µM, and still more preferably at a concentration of 6.67 µM. The detergent for the GALC assay is sodium taurocholate, present in the assay mix at a concentration of between 4.5 and 18 g/L, preferably at a concentration of 9.6 g/L. The detergent for the GALC assay also includes oleic acid at a concentration of between 0.6 and 1.8 g/L, preferably at a concentration of about 1 g/L, and more preferably at a concentration of 1.2 g/L. The buffer for the GALC assay is a phosphate/citrate buffer at a concentration of between about 0.09 and 0.27 M, preferably at a concentration of 0.18 M. The GALC assay mix should be at a pH of between 4.2 and 4.6, preferably pH 4.4

To perform the GALC assay (described in further detail below) 20-40 µl, preferably 25-µl, and more preferably 30 µl of the GALC assay mix is combined with a single 3.2 mm DBS punch. Thus, each GALC reaction will contain between about 2-3.5 µl blood (i.e., the amount of blood in a single 3.2 mm punch). Preferably, each assay will include about 3 µl mm blood, and more preferably, will contain 2.8 µl blood. The DBS punch is reacted with the GALC assay mix according to the steps described herein below. During the reaction, however, the concentration of substrate in the assay is between 0.5 and 1.5 mM, preferably 0.8 and 1.2 mM, and more preferably 1.0 mM.

In addition to the absolute concentrations of assay mix components described above, the invention contemplates that the ratio of assay components to the amount of substrate in the mix is an important factor for optimizing the assay reaction. Accordingly, to assay for GALC activity the ratio of substrate to internal standard is about 150:1, and in a preferred embodiment is 150:1. The ratio of sodium taurocholate to substrate in the GALC assay mix is about 17.8:1, and in a preferred embodiment, is 17.8:1. The ratio of oleic acid to substrate is about 4.25:1, and in a preferred embodiment, is 4.25:1. The ratio of buffer to substrate is about 180:1, and in a preferred embodiment, is 180:1.

The specific components and amounts used for each of the five assay mixtures are shown in Table 1.

TABLE 1

| ABG (Gaucher) | Assay Mix | ASM (Niemann-Pick) | Assay Mix | GAA (Pompe) | Assay Mix |
|---|---|---|---|---|---|
| Substrate (mmol/L) | 0.67 | Substrate (mmol/L) | 0.33 | Substrate (mmol/L) | 0.667 |
| Internal standard (µmol/L) | 13.33 | Internal standard (µmol/L) | 6.67 | Internal standard (µmol/L) | 6.67 |
| Detergent (g/L Sodium Taurocholate) | 16 | Detergent (g/L Sodium Taurocholate) | 1 | Detergent (g/L CHAPS) | 10 |
| | | Inhibitor (mmol/L Zinc Chloride) | 0.6 | Inhibitor (umol/L Acarbose) | 13.3 |
| Buffer (mol/L Phosphate/Citrate) | 0.62 | Buffer (mol/L Sodium Acetate) | 0.92 | Buffer (mol/L Phosphate/Citrate) | 0.3 |
| pH | 5.1 | pH | 5.7 | pH | 4.0 |
| Incubation solution | 15 µL reagent + 10 µL dbs extract | Incubation solution | 15 µL reagent + 10 µL dbs extract | Incubation solution | 15 µL reagent + 10 µL dbs extract |
| Concentration during incubation | | | | | |
| Substrate (mmol/L) | 0.4 | Substrate (mmol/L) | 0.2 | Substrate (mmol/L) | 0.4 |
| Internal standard (µmol/L) | 8.0 | Internal standard (µmol/L) | 4.0 | Internal standard (µmol/L) | 4.0 |
| Detergent (g/L Sodium Taurocholate) | 9.6 | Detergent (g/L Sodium Taurocholate) | 0.6 | Detergent (g/L Chaps) | 6 (Chaps) |
| Buffer (mol/L Phosphate/Citrate) | 0.4 | Inhibitor (mmol/L Zinc Chloride) | 0.4 | Inhibitor (umol/L Acarbose) | 8 |
| pH | 5.1 | Buffer (mol/L Sodium Acetate) | 0.6 | Buffer (mol/L Phosphate/Citrate) | 0.18 |
| | | pH | 5.7 | pH | 4.0 |
| Incubation volume (ul) | 25 | Incubation volume (ul) | 25 | Incubation volume (ul) | 25 |
| Ratio | | | | | |
| S/IS | 50 | S/IS | 50 | S/IS | 100 |
| Detergent/S (g/mmol) | 45 | Detergent/S (g/mmol) | 5.6 | Detergent/S (g/mmol) | 24.3 |
| Buffer/S | 925 | Inhibitor/S | 1.82 | Inhibitor/S | 0.02 |
| | | Buffer/S | 2788 | Buffer/S | 450 |
| | | GLA (Fabry) | Assay Mix | GALC (Krabbe) | Assay Mix |
| | | Substrate (mmol/L) | 3.33 | Substrate (mmol/L) | 1 |
| | | Internal Standard (µmol/L) | 6.67 | Internal Standard (µmol/L) | 6.67 |
| | | Detergent (g/L Sodium Taurocholate) | 3 | Detergent (g/L Sodium Taurocholate) | 9.6 |
| | | Inhibitor (mmol/L N-Acetyl-galactosamine) | 160 | Detergent (g/L Oleic Acid) | 1.2 |
| | | Buffer (mol/L Sodium Acetate) | 0.142 | Buffer (mol/L Phosphate/Citrate) | 0.18 |
| | | pH | 4.6 | pH | 4.4 |
| | | Incubation solution | 15 µL reagent + 10 µL dbs extract | Incubation solution | 30 µL cktl + 1 dbs (3 mm) |
| | | Concentration during incubation | | | |
| | | Substrate (mmol/L) | 2.0 | Substrate (mmol/L) | 1 |
| | | Internal standard (µmol/L) | 4.0 | Internal standard (µmol/L) | 6.67 |
| | | Detergent (g/L Sodium Taurocholate) | 1.8 | Detergent (g/L Sodium Taurocholate) | 9.6 |
| | | Inhibitor (mmol/L N-Acetylgalactosamine) | 96 | Detergent (mmol/L Oleic Acid) | 1.2 |
| | | Buffer (mol/L Sodium Acetate) | 0.085 | Buffer (mol/L Phosphate/Citrate) | 0.18 |
| | | pH | 4.6 | pH | 4.4 |
| | | Incubation volume | 25 | Incubation volume (ul) | 30 |

TABLE 1-continued

| | Ratio | | |
|---|---|---|---|
| S/IS | 499 | S/IS | 150 |
| Detergent/S (g/mmol) | 1.68 | Sodium Taurocholate/S (g/mmol) | 17.8 |
| Inhibitor/S | 48 | Oleic Acid/S (g/mmol) | 4.25 |
| Buffer/S | 43 | Buffer/S | 180 |

In one embodiment, any or all of the above enzyme assay mixtures can be prepared in a concentrated form that is then diluted prior to use. For example, the assay mixtures can be prepared as 0.5×, 2×, 5×, 10×, or 20× or more. The concentrated assay mix can then be diluted to an appropriate concentration with the DBS extract. For example, a smaller amount (or larger amount in the case of a 0.5× concentration) of the concentrated assay mixture can be used, as would be determined by one of skill in the art, to achieve the concentrations and/or ratios of components described above for each assay mixture. Alternatively, the concentrated assay mix could be diluted with a non-reactive buffer (e.g., water) to the correct concentration prior to use in the enzyme activity assays described herein. In a further embodiment, the assay mix could be lyophilized for long term storage, and then re-hydrated prior to use. Methods for lyophilizing are known in the art. In addition, the assay mixes described herein can be prepared in bulk form. That is, the components can be mixed in to achieve the concentrations and/or ratios described above, but in a volume sufficient for multiple reactions. The assay mixtures can be prepared in volumes appropriate for 2, 10, 50, 100, 600, or 1200 or more individual reactions. In addition, subsets of the components for each assay mix can be premixed prior to use in the assay. For example, the substrate and internal standard may be premixed at an appropriate ratio (see Table 1). The other assay components can then be added to the premixed substrate/internal standard. Any and all sub-combinations of the components of the assay mix can be premixed prior to initiation of the assay and are contemplated by the invention (e.g., substrate/internal standard/buffer or substrate/internal standard/detergent or buffer/detergent/inhibitor).

Methods for Determining Enzyme Activity in DBS

The instant invention provides a method to determine the activity of one or more lysosomal enzymes, specifically, ABG, ASM, GAA, GLA, and GALC. The assay for enzyme activity is performed by contacting a 3.2 mm DBS (that is, dried blood carried on an inert surface such as filter paper) punch or an extract prepared from a 3.2 mm DBS punch with the assay mix described above that is specific for the enzyme sought to be assayed.

The assays are designed to be used in combination with blood samples that are routinely taken from newborn infants after birth. The blood samples are typically prepared as a blood drop or smear on a piece of filter paper or other suitable substrate. These drops are generally referred to as newborn screening cards, but for purposes of the invention are referred to as a dried blood spot (DBS). While the invention is likely to be used to screen for enzyme activity from newborn DBS, it is understood that enzyme activity can be screened in DBS obtained from individuals of any age, such as children, adolescents, and/or adults, including populations of individuals at high risk for lysosomal storage disease.

The invention utilizes 3.2 mm diameter "punches" taken from the DBS; that is, a 3.2 mm circular piece of the paper containing the dried blood is cut out of the DBS using a hole-punch. The 3.2 mm piece could also be hand-cut from the DBS, or separated from the DBS by other means sufficient to produce a 3.2 mm sample from the DBS. While typically circular in shape, the 3.2 mm sample could take any shape, provided that the amount of dried blood in the sample is equivalent to that in a 3.2 mm circular punch. Typically, a 3.2 mm circular punch from a newborn DBS will contain between about 2 and 3.5 µl of blood, preferably between about 2.5 and 3.2 µl of blood, more preferably about 2.8-3 µl of blood, and still more preferably, 2.8 µl of blood.

It is generally possible to take between 3-7 3.2 mm punches from a single DBS. The punches are preferably taken from the perimeter of the DBS, rather than the center, because the amount of blood in the perimeter of the DBS is more consistent than that in the center of the DBS (where the amount of blood is usually higher relative to the perimeter).

The 3.2 mm punch can be used directly in an assay for enzyme activity, or the blood from a 3.2 mm punch can be extracted from the substrate on which it is dried. The DBS punch can be extracted by incubating the 3.2 mm DBS punch with suitable buffer. For example a single 3.2 mm punch can be extracted by incubating it with 60-80 µl of sodium phosphate buffer (pH 7.1) at 20-45° C. for between 10 minutes and 5 hours. Preferably the extraction is performed in 70 µl sodium phosphate buffer (pH 7.1) at 37° C. for 1 hour. The DBS punch extract can then be used in the assays for specific enzyme activity described below. Based on the amount of blood in a single 3.2 mm DBS punch, the amount of blood in the DBS extract will be between 0.25 and 0.33 µl per 10 µl DBS extract at the low end of the range (extraction of a 3.2 mm DBS containing 2 µl blood in a volume of between 60 and 80 µl extraction buffer) and between 0.438 and 0.583 µl per 10 µl DBS extract at the high end of the range (extraction of a 3.2 mm DBS containing 3.5 µl blood in a volume of between 60 and 80 µl extraction buffer). In a preferred embodiment, the amount of blood in a 3.2 mm DBS is about 2.8 µl blood and the amount of blood in 10 µl of DBS extract is about 0.4 µl (based on an extraction buffer volume of 70 µl).

For the second ABG assay described herein, the DBS is preferably extracted in an aqueous buffer solution that includes detergent. The detergent is preferably sodium taurodeoxycholate with a minimum purity of 97% TLC (Sigma T0557). Preferably, the DBS extraction buffer for the second ABG assay includes 0.30 M citrate phosphate with 1% sodium taurodeoxycholate and 1% triton X-100, pH 5.2. To extract the DBS, 200 µl of the extract buffer is added to each 3.2 mm DBS punch, and incubated for 30-90 minutes, preferably 60 minutes, at room temperature. The samples are then centrifuged at 10,000-18,000 rpm, preferably 14,000 rpm for 15-45 minutes, preferably 30 minutes. This centrifugation step is necessary to augment assay precision and accuracy. While it is preferred that the second ABG assay is performed using a DBS extract as described, it is contemplated that the assay could also be performed using a DBS punch, provided that the sodium taurodeoxycholate detergent is added to the reaction mixture.

Reaction of DBS and DBS Extract with Assay Mix

The assay mixtures are added to appropriate containers to be reacted with the DBS punches or DBS punch extract (or both). Any type of container (e.g., a microfuge tube, or multiwell plate) can be used, however, it is preferred that the reactions are carried out in a multiwell plate, such as a 96 well polypropylene plate. Other containers known to those of skill in the art may be used according to the methods of the invention.

The assay mixtures described above are each added to separate wells of a multiwell plate (or separate containers if other types of containers are being used). For ASM, ABG (first assay), GAA, and GLA assays 10-20 $\mu$l of assay mix (specific for each enzyme), preferably 13-17 $\mu$l, and more preferably 15 $\mu$l is added to each well followed by 5-20 $\mu$l of DBS extract, preferably 10 $\mu$l DBS extract. For the GALC assay, one 3.2 mm DBS punch is added to a well, followed by 20-40 $\mu$l, preferably 25-35 $\mu$l, and more preferably 30 $\mu$l GALC assay mix. A sixth container or well may also be used as a blank and contains the same amount of assay mix used to assay for enzyme activity (i.e., 10-20 $\mu$l for ASM, ABG, GAA, GLA; 20-40 $\mu$l for GALC) combined with either DBS extraction buffer or a 3.2 mm punch taken from the same substrate as the DBS, minus the dried blood.

In one embodiment, one or more assay wells or containers contain both a 3.2 mm DBS punch and DBS extract. Likewise, while it is preferred that the ASM, ABG, GAA, and GLA assays are performed using DBS extract, and the GALC assay is performed using a 3.2 mm DBS punch, each assay may be performed using either DBS extract or a 3.2 mm DBS punch.

The present invention can be used to determine the activity of a single enzyme in a single DBS sample or may be used in a multiplex format to assay multiple enzyme activities in a given DBS sample, and/or multiple enzyme activities from multiple individuals. In the multiplex format, DBS samples from one or a plurality of individuals are incubated under appropriate conditions ("reacted") with the assay mix corresponding to the enzyme activities to be assayed. For example, the methods of the invention may be used to assay DBS samples from "n" individuals for each of the five enzyme activities described herein (ASM, ABG, GAA, GLA, and GALC). When expanded to include at least one blank reaction, the multiplex format will require (5×n+the number of blanks) separate reactions, all of which can be performed simultaneously in a multiwell plate (or a plurality of multiwell plates). Once each individual enzyme reaction is performed using extract or a whole DBS punch from a given individual, the quenched reactions can be pooled prior to mass spectrometry. Thus, from a single sample analyzed by mass spectrometry, under the multiplex format, the activities of all five enzymes can be determined.

Once the assay mix is combined with the DBS extract and/or DBS punch for each enzyme activity to be assayed (including at least one control reaction), the combination, referred to as a reaction mix is incubated at between 36 and 38° C. for 1 to 48 hours. Preferably the reaction mix is incubated at 37° C. for 20-30 hours, and more preferably for 20-24 hours.

After incubation, the enzyme activity of each reaction is stopped or "quenched" by the addition of a mixture of 1:1 ethyl acetate:MeOH to each well. For the reaction volumes described herein, a volume of 100-200 $\mu$l is added to each reaction. In a preferred embodiment, where a reaction volume of between 25 and 30 $\mu$l is used, 100 $\mu$l ethyl acetate:MeOH is used to quench each reaction. Provided that the ratio of ethyl acetate to MeOH remains 1:1, the concentration of ethyl acetate and MeOH can vary. For example, 20-100% ethyl acetate can be used and 20-100% MeOH can be used, provided that the ratio of ethyl acetate to MeOH is 1:1. Preferably the concentration of each is 100%.

Once the reactions are quenched, in a multiplexed assay format, each assay reaction (excluding the control) for a given DBS sample can be combined in a single container (i.e., in a single well of a multiwell plate). If a non-multiplex format is being used, then each reaction is processed individually through the following steps. The combined reaction mix is then extracted by adding ethyl acetate followed by an equal amount of water. As used herein, the term "extraction" or "extract" refers to the separation of the assay sample into an organic phase and inorganic phase. Between 1 and 16 volumes of ethyl acetate and water can be used, however it is preferred that in a non-multiplex format, at least 2 volumes of each of ethyl acetate and water are added to each well. In contrast, in a multiplex format, that is, where the enzyme assay reactions have been pooled, at least a ⅗ volume of each of ethyl acetate and water are added to each well. The ethyl acetate and water is then mixed with the combined reaction assays and then centrifuged. This results in a separation of the organic phase from the inorganic phase (i.e., extraction). Substantially all of the top phase (organic) is then removed and placed in a clean container or well. The extracted assay reactions are then dried under a stream of nitrogen. In addition, the container or well comprising the extracted organic phase can be warmed to any temperature between room temperature and about 25° C. to assist in the drying process.

The samples are then reconstituted in a mixture of ethyl acetate and MeOH at a ratio of 19:1 ethyl acetate:MeOH, and then purified to remove buffer components by passing them over silica gel under vacuum. As used herein, the term "purify" or "purifying" refers to a step of removing the buffer components of the assay mixture. The ethyl acetate:MeOH mixture can contain between about 90-99% ethyl acetate and 1-10% MeOH. Prior to adding the samples to the silica gel, the gel is washed with a 19:1 mixture of ethyl acetate:MeOH. Preferably the silica gel used in the purification step has a particle size of between 43 and 60 $\mu$m and a pore size of between 50-70 Å, preferably 60 Å. Although silica gel is the preferred mode of purification, other commercially available methods may be used by one of skill in the art to purify the enzyme assays including, but not limited to, on-line solid phase extraction, bead solid phase extraction, or high turbo flow liquid chromatography (HTLC; available from Cohesive). After the samples are purified through the silica gel, the gel is washed with a 19:1 mixture of ethyl acetate:MeOH. The clean-up steps that include both liquid-liquid or solid phase extraction can be omitted or can be replaced with other methods of separation provided that the other methods can separate lipid-like compounds from detergent, buffer, or other compounds eluted from the blood. A more specific protocol for silica gel purification of the assay samples is described in the Examples.

The resulting purified assay sample is then dried under nitrogen, and can be optionally heated to between room temperature and about 25° C. to speed the drying process. The amount of product (produced by the activity of the enzyme to be assayed) and internal standard present in the assay samples is then determined by mass spectrometry analysis. Prior to analysis, the samples are reconstituted in a mixture of acetonitrile and water with the addition of formic acid. Preferably the reconstitution buffer comprises 80% acetonitrile, 20% water, and 0.2% formic acid. Alternate organic solvent compositions could also be used to reconstitute the samples, such as, but not limited to, 5 mmol/L ammonium formate in acetonitrile-water (4:1 volume). The reconstituted samples are then analyzed by mass spectrometry, preferably tandem mass spectrometry, to determine the amount of each product and internal standard present in the each sample, which is then used to calculate the activity of each enzyme.

The second ABG DBS assay measures the ABG-catalyzed cleavage of the fluorogenic substrate 4-MU-$\beta$-Glu by detecting the product 4-MU in a fluorometer. Enzymes are eluted from dried blood spots with a buffered detergent solution. The eluate is incubated with the substrate at acidic pH. After 20 hours the reaction is stopped by the addition of alkaline EDTA solution. Conduritol B epoxide (CBE), a specific and irreversible inhibitor of ABG, is used to assess the contribution of other $\beta$-glucosidase isoenzymes to the activity. The difference between activities in the absence presence of CBE is used to quantitate ABG activity. A bile salt, sodium taurodeoxycholate, acts as a detergent and as an activator of ABG, however, it is contemplated that other detergents could be used such as n-dodecymaltoside, ASB14, C7B20, zwettergent 3-14, or sodium taurocholoate. The purity of sodium taurodeoxycholate is important to the success of the assay. Impurities in the sodium taurodeoxycholate can precipitate and affect the precision of the assay. To minimize the impact of precipitation, it is preferred that the second ABG assay utilizes sodium taurodeoxycholate of at least 97% purity.

More specifically, to each 3.2 mm DBS is added 100-300 µl, preferably 200 µl Buffered Extractant (defined above), and the DBS is allowed to incubate at room temperature for 30-90 minutes, preferably 60 minutes. The filter paper or other substrate that the DBS was contained on is then removed and the sample is centrifuged at 10,000 to 20,000 rpm for 15-45 minutes, preferably at 14,000 rpm for 30 minutes.

Each test sample is assayed in duplicate, preferably for both uninhibited and inhibited working substrate solutions. For example, 60-100 µl, preferably 80 µl, of uninhibited working substrate solution is added to a well (or other container) per sample, and 60-100 µl, preferably 80 µl, of inhibited working substrate solution is added to a well (or other container) per sample (optionally uninhibited and inhibited working substrate solution are separately added to one additional well per sample). To each test well is then added 20-60 µl, preferably 40 µl of the DBS extract. The reaction is then allowed to incubate at 35-39° C., preferably 37° C. for 15-25 hours, preferably 20 hours. The reactions are then stopped by adding an appropriate amount of stop buffer (80-120 µl, preferably 100 µl). The assay reactions are then centrifuged for 30-90 minutes, preferably 60 minutes, at 2000-3000 rpm, preferably 2500 rpm.

The reactions can then be assessed by fluorometry at 355 nm excitation and 460 nm emission to determine the amount of product (fluorescence) produced by the enzymatically processed substrate. The amount of product (fluorescence) in the reaction mixtures without CBE is determined, and the amount of product (fluorescence) of the reaction mixtures with CBE is determined. The amount of product in the reaction mix with CBE is then subtracted from the amount of product in the reaction mix without CBE. The result is the differential fluorescence and it is then compared to a standard curve. The equation (4-MU, pmol)=$\alpha \times$fluorescence is then fit to the data, wherein $\alpha$ is the slope of the regression line. The differential fluorescence levels measured above are then converted into pmol per sample by linear regression using the standard curve. This result is then converted into pmol/(DBS punch*h) by dividing the result by the incubation time in hours, and multiplying by the fraction of extract used per well.

The standard curve used in the second ABG assay can be generated in parallel with the sample assays, or can be generated separately and kept as a reference for future tests. The standard curve may degrade over time and should be made fresh is there is a noticeable change in the slope. To prepare a standard curve, a 12.5 µM 4-MU standard working solution is first prepared by diluting 5 µl of 25 mM 4-MU stock solution into 10 ml water. Serial dilutions of the 4-MU standard are then prepared. For example, a serial dilution, in one embodiment, has 4-MU concentrations per well of 750, 375, 188, 93.8, 46.9, 23.4, 11.7, and 0 pmol per well. 100 µl of stop buffer is then added to each well, and the standard curve reactions are centrifuged for 30-90 minutes, preferably 60 minutes, at 2000-3000 rpm, preferably 2500 rpm. The fluorescence of the standard curve wells is determined using a fluorometer with 355 nm excitation and 460 nm emission wavelengths.

Mass Spectrometry Analysis

The methods of the invention, in part, use mass spectrometry for determining the amount or presence of the product or products of the enzyme assays (i.e., the products generated by the action of the enzyme in a DBS punch on the substrate), and the internal standard. It should be noted, that for the second ABG assay, enzyme activity is measured using a fluorescence-based assay. A variety of configurations of mass spectrometers can be used in a method of the invention. Several types of mass spectrometers are available or can be produced with various configurations. In general, a mass spectrometer has the following major components: a sample inlet, an ion source, a mass analyzer, a detector, a vacuum system, and instrument-control system, and a data system.

Difference in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nanospray and microspray or matrix-assisted laser desorption. Common mass analyzers include a quadruple mass filter, ion trap mass analyzer and time-of-flight mass analyzer.

The ion formation process is a starting point for mass spectrum analysis. Several ionization methods are available and the choice of ionization method depends on the sample to be analyzed. For example, for the analysis of amino acids a relatively gentle ionization procedure such as electrospray ionization (ESI) can be desirable. For ESI, a solution containing the sample is passed through a fine needle at high potential which creates a strong electrical field resulting in a fine spray of highly charged droplets that is directed into the mass spectrometer. Other ionization procedures include, for example, fast-atom bombardment (FAB) which uses a high-energy beam of neutral atoms to strike a solid sample causing desorption and ionization. Matrix-assisted laser desorption ionization (MALDI) is a method in which a laser pulse is used to strike a sample that has been crystallized in an UV-absorbing compound matrix.

Other ionization procedures known in the art include, for example, plasma and glow discharge, plasma desorption ionization, resonance ionization, and secondary ionization.

Electrospray ionization (ESI) has several properties that are useful for the invention described herein. For example, ESI can be used for biological molecules such as lipid or glycophingolipids that are difficult to ionize or vaporize. In addition, the efficiency of ESI can be very high which provides the basis for highly sensitive measurements. Furthermore, ESI produces charged molecules from solution, which is convenient for analyzing enzymatic products and internal standards that are in solution. In contrast, ionization procedures such as MALDI require crystallization of the sample prior to ionization.

Since ESI can produce charged molecules directly from solution, it is compatible with samples from liquid chromatography systems. For example, a mass spectrometer can have an inlet for a liquid chromatography system, such as an HPLC, so that fractions flow from the chromatography column into the mass spectrometer.

This in-line arrangement of a liquid chromatography system and mass spectrometer is sometimes referred to as LC-MS. A LC-MS system can be used, for example, to separate enzymatic products and internal standards from complex mixtures before mass spectrometry analysis. In addition, chromatography can be used to remove salts or other buffer components from the sample before mass spectrometry analysis (i.e., in addition to, or in place of silica gel purification). For example, desalting of a sample using a reversed-phase HPLC column, in-line or off-line, can be used to increase the efficiency of the ionization process and thus improve sensitivity of detection by mass spectrometry.

A variety of mass analyzers are available that can be paired with different ion sources. Different mass analyzers have different advantages as known to one skilled in the art and as described herein. The mass spectrometer and methods chosen for detection depends on the particular assay, for example, a more sensitive mass analyzer can be used when a small amount of ions are generated for detection.

Several types of mass analyzers and mass spectrometry methods are described below.

Quadruple mass spectrometry utilizes a quadruple mass filter or analyzer. This type of mass analyzer is composed of four rods arranged as two sets of two electrically connected rods. A combination of rf and dc voltages are applied to each pair of rods which produces fields that cause an oscillating movement of the ions as they move from the beginning of the mass filter to the end. The result of these fields is the production of a high-pass mass filter in one pair of rods and a low-pass filter in the other pair of rods. Overlap between the high-pass and low-pass filter leaves a defined m/z that can pass both filters and traverse the length of the quadrupole. This m/z is selected and remains stable in the quadruple mass filter while all other m/z have unstable trajectories and do not remain in the mass filter. A mass spectrum results by ramping the applied fields such that an increasing m/z is selected to pass through the mass filter and reach the detector. In addition, quadruples can also be set up to contain and transmit ions of all m/z by applying a rf-only field. This allows quadrupoles to function as a lens or focusing system in regions of the mass spectrometer where ion transmission is needed without mass filtering. This will be of use in tandem mass spectrometry as described further below.

A quadruple mass analyzer, as well as the other mass analyzers described herein, can be programmed to analyze a defined m/z or mass range. This property of mass spectrometers is useful for the invention described herein. Since the mass range of enzymatic products and/or internal standards will be known prior to an assay, a mass spectrometer can be programmed to transmit ions of the projected correct mass range while excluding ions of a higher or lower mass range.

The ability to select a mass range can decrease the background noise in the assay and thus increase the signal-to-noise ratio as well as increasing the specificity of the assay. Therefore, the mass spectrometer can accomplish an inherent separation step as well as detection and identification of enzymatic products and internal standards.

Ion trap mass spectrometry utilizes an ion trap mass analyzer. In these mass analyzers, fields are applied so that ions of all m/z are initially trapped and oscillate in the mass analyzer. Ions enter the ion trap from the ion source through a focusing device such as an octapole lens system. Ion trapping takes place in the trapping region before excitation and ejection through an electrode to the detector. Mass analysis is accomplished by sequentially applying voltages that increase the amplitude of the oscillations in a way that ejects ions of increasing m/z out of the trap and into the detector. In contrast to quadruple mass spectrometry, all ions are retained in the fields of the mass analyzer except those with the selected m/z. One advantage to ion traps is that they have very high sensitivity, as long as one is careful to limit the number of ions being tapped at one time. Control of the number of ions can be accomplished by varying the time over which ions are injected into the trap. The mass resolution of ion traps is similar to that of quadruple mass filters, although ion traps do have low m/z limitations.

Time-of-flight mass spectrometry utilizes a time-of-flight mass analyzer. For this method of m/z analysis, an ion is first given a fixed amount of kinetic energy by acceleration in an electric field (generated by high voltage). Following acceleration, the ion enters a field-free or "drift" region where it travels at a velocity that is inversely proportional to its m/z. Therefore, ions with low m/z travel more rapidly than ions with high m/z. The time required for ions to travel the length of the field-free region is measured and used to calculate the m/z of the ion.

One consideration in this type of mass analysis is that the set of ions being studied be introduced into the analyzer at the same time. For example, this type of mass analysis is well suited to ionization techniques like MALDI which produces ions in short well-defined pulses. Another consideration is to control velocity spread produced by ions that have variations in their amounts of kinetic energy. The use of longer flight tubes, ion reflectors, or higher accelerating voltages can help minimize the effects of velocity spread. Time-of-flight mass analyzers have a high level of sensitivity and a wider m/z range than quadruple or ion trap mass analyzers. Also data can be acquired quickly with this type of mass analyzer because no scanning of the mass analyzer is necessary.

Tandem mass spectrometry can utilize combinations of the mass analyzers described above. Tandem mass spectrometers can use a first mass analyzer to separate ions according to their m/z in order to isolate an ion of interest for further analysis. The isolated ion of interest is then broken into fragment ions (called collisionally activated dissociation or collisionally induced dissociation) and the fragment ions are analyzed by the second mass analyzer. These types of tandem mass spectrometer systems are called tandem in space systems because the two mass analyzers are separated in space, usually by a collision cell. Tandem mass spectrometer systems also include tandem in time systems where one mass analyzer is used, however the mass analyzer is used sequentially to isolate an ion, induce fragmentation, and then perform mass analysis.

Mass spectrometers in the tandem in space category have more than one mass analyzer. For example, a tandem quadruple mass spectrometer system can have a first quadruple mass filter, followed by a collision cell, followed by a second quadruple mass filter and then the detector. Another arrangement is to use a quadruple mass filter for the first mass analyzer and a time-of-flight mass analyzer for the second mass analyzer with a collision cell separating the two mass analyzers.

Other tandem systems are known in the art including reflectron-time-of-flight, tandem sector and sector-quadrupole mass spectrometry.

Mass spectrometers in the tandem in time category have one mass analyzer that performs different functions at different times. For example, an ion trap mass spectrometer can be used to trap ions of all m/z. A series of rf scan functions are applied which ejects ions of all m/z from the trap except them/z of ions of interest.

After the m/z of interest has been isolated, an rf pulse is applied to produce collisions with gas molecules in the trap to induce fragmentation of the ions. Then the m/z values of the fragmented ions are measured by the mass analyzer. Ion cyclotron resonance instruments, also known as Fourier transform mass spectrometers, are an example of tandem-in-time systems.

Several types of tandem mass spectrometry experiments can be performed by controlling the ions that are selected in each stage of the experiment. The different types of experiments utilize different modes of operation, sometimes called "scans," of the mass analyzers. In a first example, called a mass spectrum scan, the first mass analyzer and the collision cell transmit all ions for mass analysis into the second mass analyzer. In a second example, called a product ion scan, the ions of interest are mass-selected in the first mass analyzer and then fragmented in the collision cell. The ions formed are then mass analyzed by scanning the second mass analyzer. In a third example, called a precursor or parent ion scan, the first mass analyzer allows the transmission of all sample ions, while the second mass analyzer is set to monitor specific fragment ions, which are generated by bombardment of the sample ions with the collision gas in the collision cell.

The second mass analyzer mass-selects the product ion of interest for transmission to the detector. Therefore, the detector signal is the result of all precursor ions that can be fragmented into a common product ion. Other experimental formats include neutral loss scans where a constant mass difference is accounted for in the mass scans. The use of these different tandem mass spectrometry scan procedures can be advantageous when large sets of analytes are measured in a single experiment as with multiplex experiments. An additional scan mode useful in the present invention is the selected or multiple reaction monitoring mode in which both of the analyzers are static, as user-selected specific ions are transmitted through the first analyzer and user-selected specific fragments arising from these ions are measured by the second analyzer. The compound under scrutiny must be known and have been well characterized prior to using this type of scan mode. This type of scan mode can be used to confirm unambiguously the presence of a compound in a matrix (e.g., blood or urine). In a preferred embodiment of the invention, the product and internal standards are assayed using the multiple reaction monitoring mode.

In view of the above, those skilled in the art recognize that different mass spectrometry methods, for example, quadruple mass spectrometry, ion trap mass spectrometry, time-of-flight mass spectrometry and tandem mass spectrometry, can use various combinations of ion sources and mass analyzers which allows for flexibility in designing customized detection protocols. In addition, mass spectrometers can be programmed to transmit all ions from the ion source into the mass spectrometer either sequentially or at the same time. Furthermore, a mass spectrometer can be programmed to select ions of a particular mass for transmission into the mass spectrometer while blocking other ions. The ability to precisely control the movement of ions in a mass spectrometer allows for greater options in detection protocols which can be advantageous when a large number of analytes, for example, from a multiplex experiment, are being analyzed.

Different mass spectrometers have different levels of resolution, that is, the ability to resolve peaks between ions closely related in mass. The resolution is defined as R=m/delta m, where m is the ion mass and delta m is the difference in mass between two peaks in a mass spectrum. For example, a mass spectrometer with a resolution of 1000 can resolve an ion with a m/z of 100.0 from an ion with a m/z of 100.1. Those skilled in the art will therefore select a mass spectrometer having a resolution appropriate for the analyte(s) to be detected.

Mass spectrometers can resolve ions with small mass differences and measure the mass of ions with a high degree of accuracy. Therefore, analytes of similar masses can be used together in the same experiment since the mass spectrometer can differentiate the mass of even closely related molecules. The high degree of resolution and mass accuracy achieved using mass spectrometry methods allows the use of large sets of analytes because they can be distinguished from each other.

Additional mass spectrometry methods are well known in the art (see Burlingame et al. Anal. Chem. 70: 647R-716R (1998); Kinter and Sherman, New York (2000)). Exemplary descriptions of mass spectrometry methods for detecting metabolic analytes include Chace D H, Hillman S L, Van Hove J L K, Naylor E W. Clin Chem 1997; 43: 210613; Rashed M S, Bucknall M P, Little D, et al. Clin Chem 1997; 43: 112941; Matern D, Strauss A W, Hillman S L, Mayatepek E, Millington D S, Trefz F K. Pediatr Res 1999: 46: 459, and Millington D S, Kodo N, Terada N, Roe D, Chace D H. International Journal of Mass Spectrometry and ion Processes 1991; 111: 21128.

From the mass spectrometry analysis, one of skill in the art is able to determine the amount of product and internal standard in each of the enzyme assays. As noted above, each enzyme product and internal standard may be assayed individually or, in a preferred embodiment, following the initial assay reaction, the products and internal standards for the five enzyme reactions are combined and assayed simultaneously by mass spectrometry. This highlights one of the advantages of the present invention. That is, the invention provides a method for the determination of multiple enzyme activities utilizing a single read out assay (i.e., tandem mass spectrometry). Thus, the invention is well adapted to be used to perform high throughput screening of multiple DBS samples for the five enzyme activities described herein, and is therefore useful for performing large scale newborn screening for the lysosomal storage diseases associated with ASM, ABG, GAA, GLA, and GALC enzyme activity.

Figure 2:
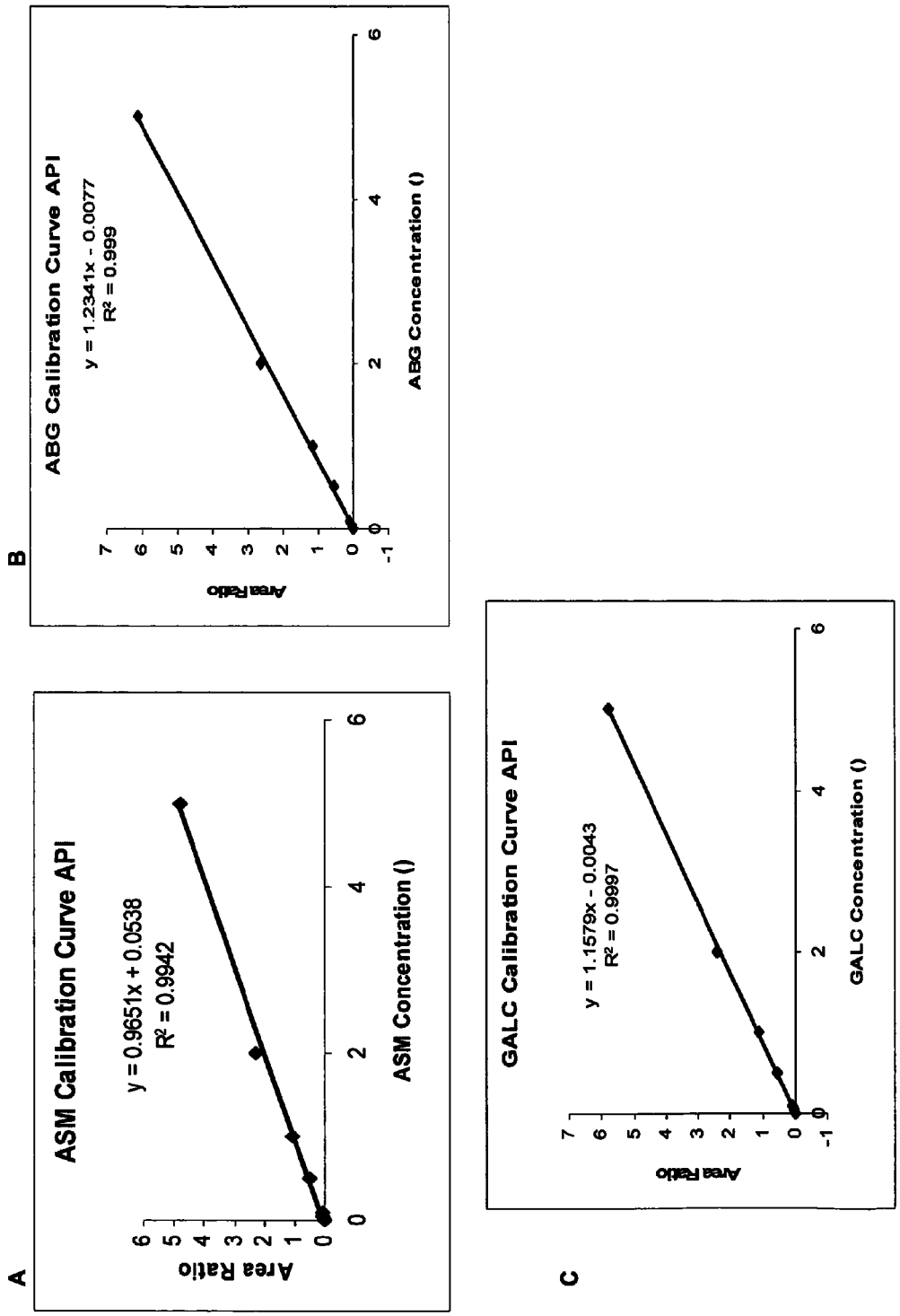
FIG. 2 (A-C) shows the calibration curves used to generate the RF for the ASM, ABG, and GALC enzyme activity calculations.
Figure 3:
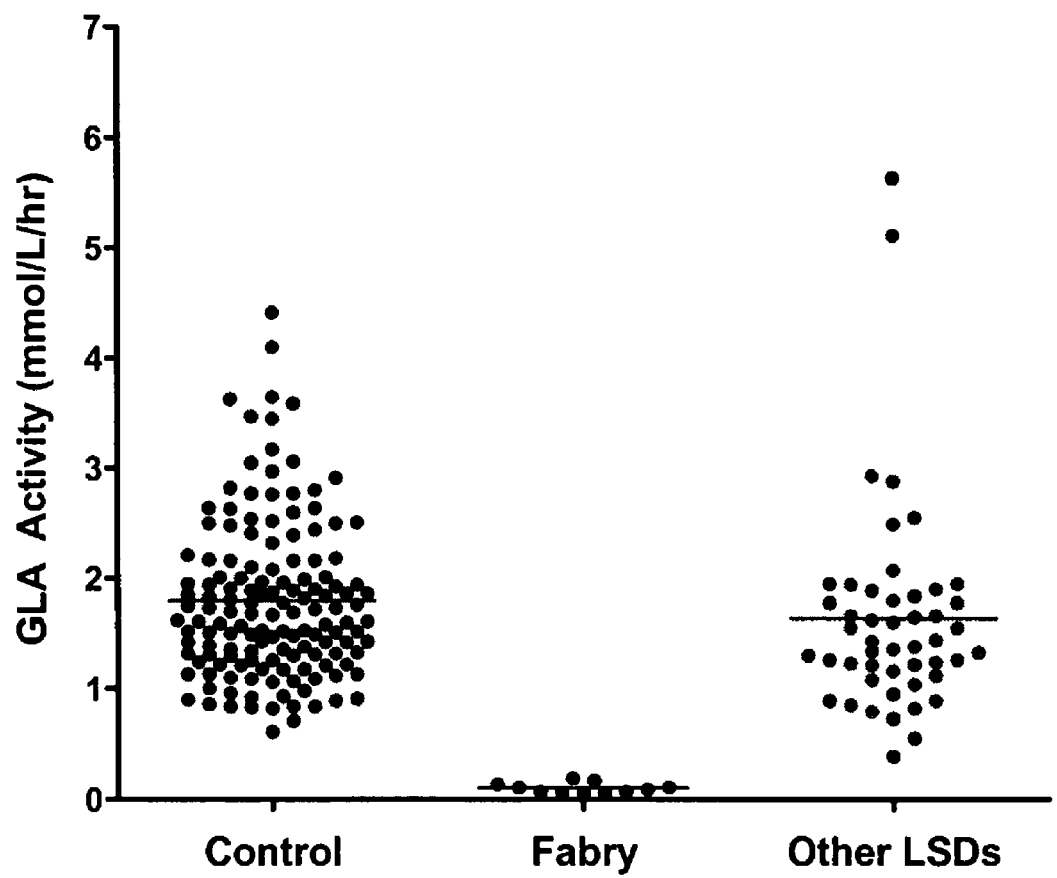
FIG. 3 shows the results of a GLA activity assay.
Figure 4:
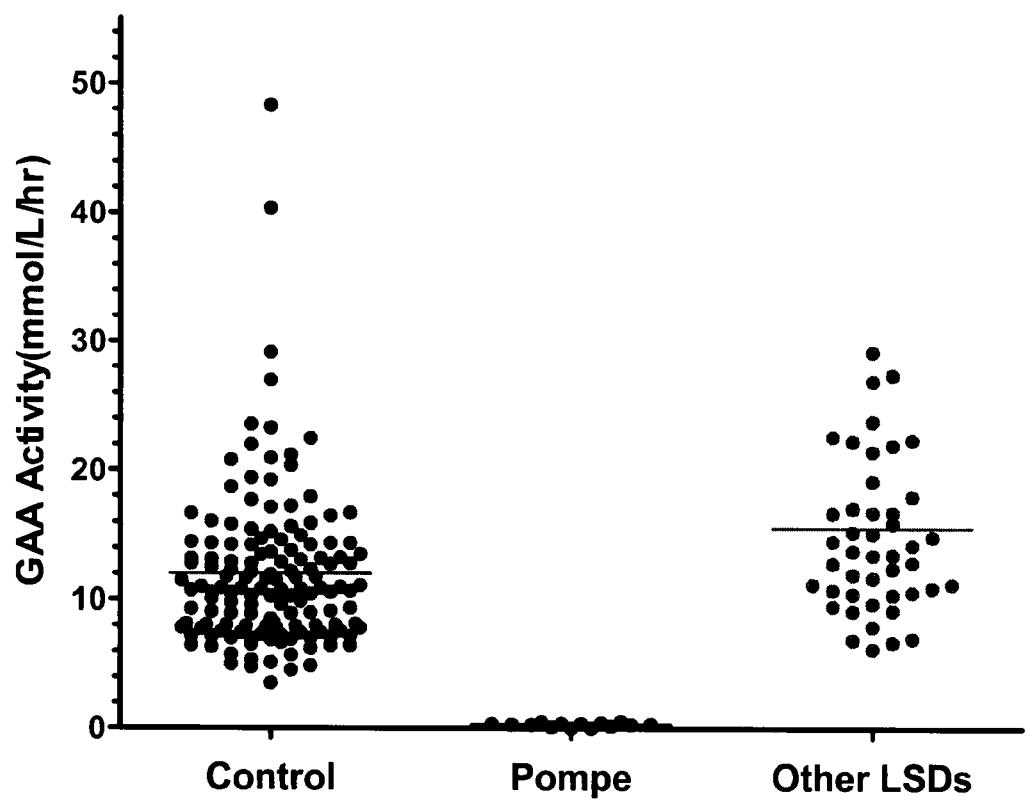
FIG. 4 shows the results of a GAA activity assay.
Figure 5:
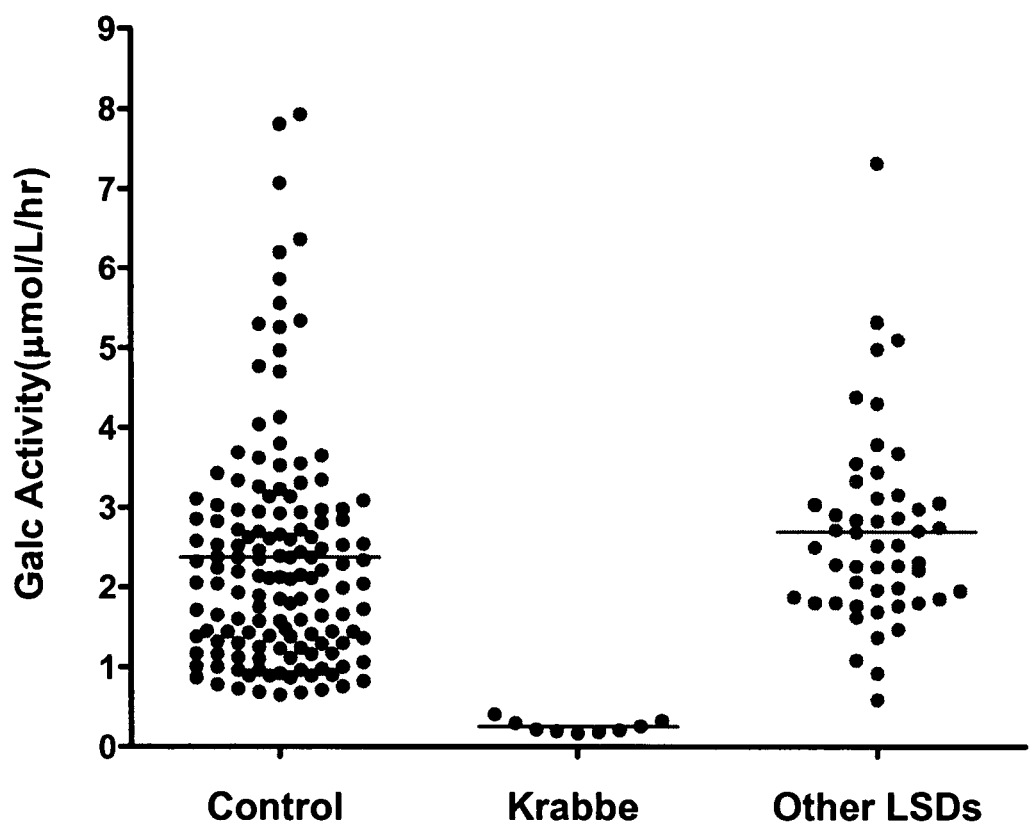
FIG. 5 shows the results of a GALC activity assay.
Figure 6:
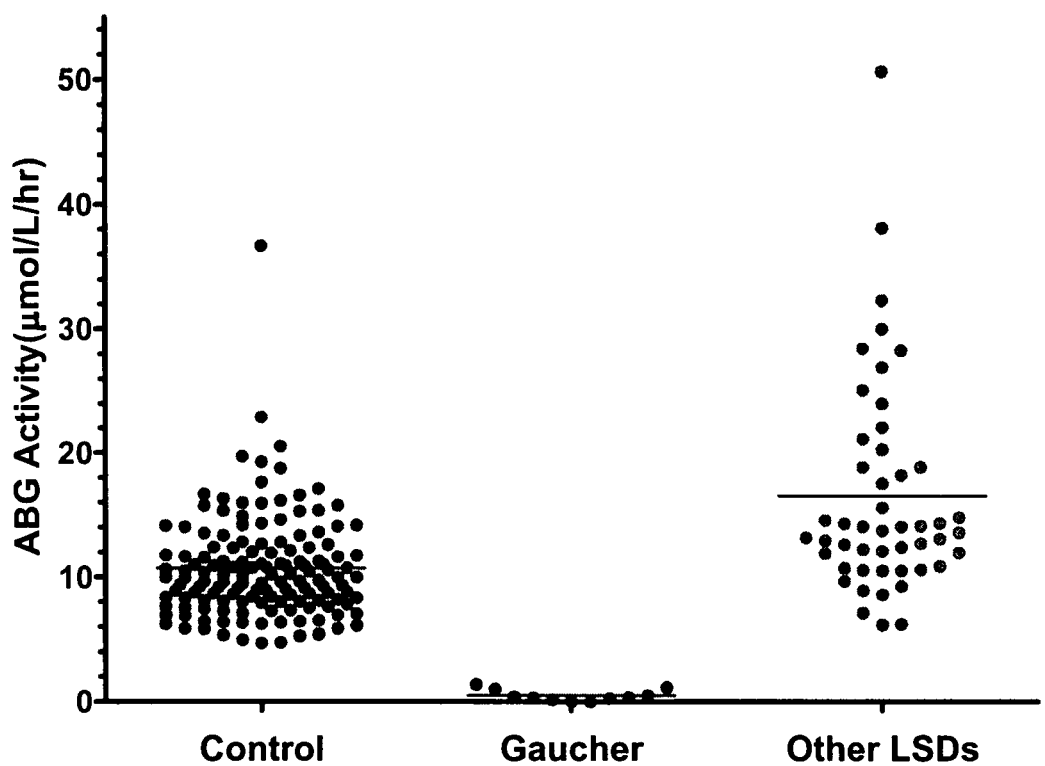
FIG. 6 shows the results of a ABG activity assay.
Figure 7:
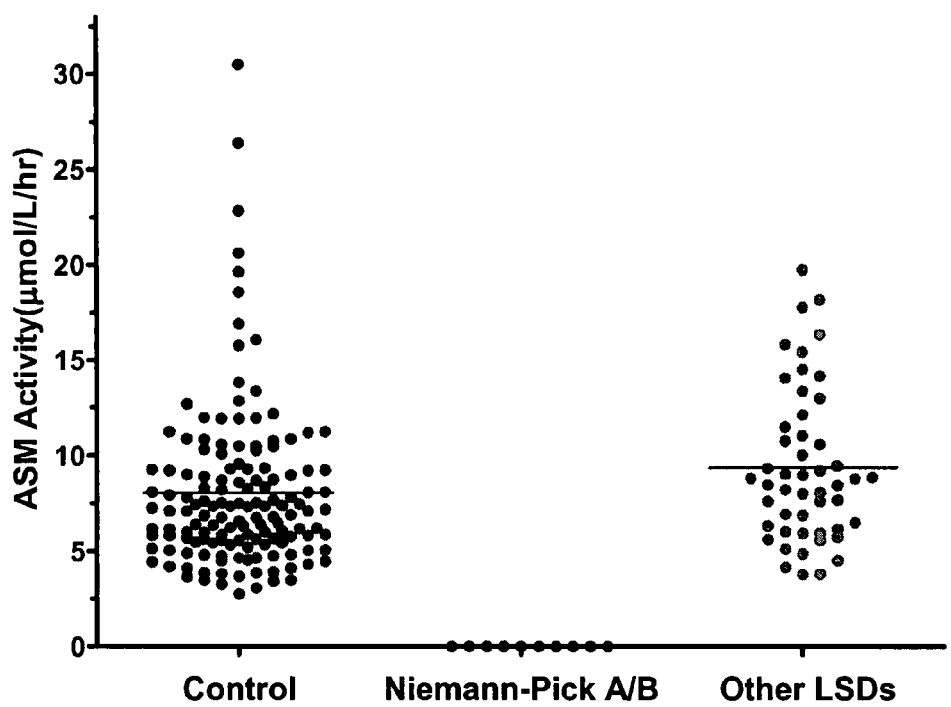
FIG. 7 shows the results of a ASM activity assay.

Once the amount of product and internal standard has been determined by mass spectrometry, these values can be used to calculate enzyme activity. Enzyme activity can be determined by applying the product and internal standard values to the following equation:

$$\text{Enzyme activity}(\mu mol/hr/L) = (P/IS)*IS/RF/T/V$$

Wherein (P/IS) is the ratio of the amount of product to the amount of internal standard as determined by mass spectrometry; RF is the response factor ratio; IS is the amount of internal standard in the enzyme assay mix; T is the incubation time; and V is the volume of blood used in the assay reaction. If the internal standard is a stable isotope analog of the molecule of interest (i.e., analog of the enzyme product), then there is no need to calculate the response factor ratio. Accordingly, it is not necessary to calculate the RF for the GLA and GAA enzyme assays. Thus, for calculating the activities of GLA and GAA, the RF value is equal to 1. For the ASM, GALC, and ABG assays however, the internal standards used are structural analogs, having similar, but not identical structures to the products. As a result they may have a slightly different ionization efficiency relative to the product. The RF is determined by constructing a calibration curve to reflect the linear relationship between spiked-in product concentrations in the solution and the area ratio of product:internal standard measured on the mass spectrometer. The slope of the resulting curve represents the RF of product to internal standard. As shown in FIG. 2A-C the RF for the ASM assay is 0.9651, the RF for the ABG assay is 1.2341, and the RF for the GALC assay is 1.1579.

Screening and Therapeutic Applications

The present invention provides methods for screening for one or more of Gaucher, Niemann-Pick A/B, Pompe, Fabry, and Krabbe diseases by determining the activity of the ABG, ASM, GAA, GLA, and GALC enzymes, respectively. It will be understood by one of skill in the art that the absolute level of activity for any of the above enzymes will vary from individual to individual. Accordingly, to facilitate the screening for decreased enzyme activity in an individual, individual samples must be compared to a population of presumptively normal samples assayed under the same conditions. One aspect of the invention provides a method for performing newborn screening assays. In this context, the activity of one or more of the lysosomal enzymes described herein is compared with the daily mean enzyme activities for that enzyme from all the newborn samples assayed on a given day. For example, in a typical setting (e.g., a newborn screening lab), newborn screening assays are performed on between 200 and 1000 individual samples in a given day. The level of activity of each enzyme assayed is compared to the mean of that enzyme activity from all the other samples (which are presumptively normal). Therefore, if 200 DBS samples from 200 individuals are tested for the five enzyme activities described herein the enzyme activity from one is compared against the mean of the 199 other presumptively normal samples. Decreased enzyme activity is identified if the enzyme activity for a particular enzyme is less than 30% of the daily mean for that enzyme, preferably less than 25%, preferably less than 20%, preferably less than 15%, preferably less than 10%, and more preferably less than 8% of the daily mean. In particular, for Fabry disease, a patient is identified as having decreased GLA enzyme activity (and potentially as having Fabry disease) if the GLA enzyme activity measured in that patient is less than 10-20% of the mean GLA activity in all the other patient samples assayed on the same day. For the four other enzyme activities described herein, decreased enzyme activity is identified if the enzyme activity is at least less than 30% of the mean activity of the same enzyme from all the other samples assayed on the same day. This method can accordingly be used as a first step in the diagnosis of any one or all of the five lysosomal storage diseases described herein. This identification of enzyme deficiency is useful to identify patients that may benefit from enzyme replacement therapies or similar treatments.

The methods of the invention, in addition to being used for newborn screening, can also be used to screen other populations, such as adolescent or adult individuals identified as high risk for developing lysosomal storage disease.

In one embodiment, following the identification of a sample that has an enzyme activity at least less than 30% of the daily mean, as described above, the individual from which the DBS sample was obtained may be screened further to confirm disease diagnosis. For example, The DBS from which the 3.2 mm punch was taken can be re-punched to obtain additional 3.2 mm punches, that are then re-analyzed in the same enzyme activity assays described above. In addition, or alternatively, the a new DBS can be prepared from the individual from which the first DBS was obtained. For example, for a newborn infant that shows low activity of one or more of the enzymes described herein, blood can be re-drawn to prepare a second DBS that is then used according to the methods of the invention to re-assess enzyme activity.

In addition, or alternatively, after a sample is identified as having an enzyme activity at least less than 30% of the daily mean, additional clinical diagnostic methods, such as genotyping, or enzyme assay in another sample type (e.g., GAA assay in lymphocytes for Pompe disease) can be used to confirm a diagnosis of one or more of the lysosomal storage diseases described herein. Confirmatory clinical assays are known in the art and can be found, for example, on the world wide web at genetests.org.

Alternatively, decreased enzyme activity can be determined by making a comparison between the enzyme activity in a test patient and the enzyme activity in a patient known to be free of the disease. In this example, decreased enzyme activity is identified if the enzyme activity in the test patient is less than the control enzyme activity by a statistically significant amount as determined by statistical analysis known to those of skill in the art (e.g., student's t-test where $P<0.05$ is significant).

A further aspect of the invention provides a method for selecting a treatment regimen and monitoring treatment of one or more of the lysosomal storage diseases described herein. In one aspect, the invention provides a method for selecting a treatment regimen for a patient based on the activity of the ABG, ASM, GAA, GALC, or GLA enzymes. For example, by determining the activity of one or more of these enzymes in an individual, a physician or other health care professional can use that information to make decisions as to the proper treatment (e.g., enzyme replacement therapy or bone marrow transplantation) for the individual in accordance with the current standard of care for the particular disease. Methods for treatment of several of the lysosomal storage diseases are known in the art (see, e.g., Grabowski and Hopkin 2003, Annu. Rev. Genomics, 4:403-36; Kaye 2001 Curr. Treat. Options Neurol., 3: 249-56; and Schiffmann and Brady 2002 Drugs, 62: 733-42).

The methods of the instant invention can also be used to monitor treatment in a patient. For example, after starting a patient on a treatment program for deficiency in one or more of the ABG, ASM, GAA, GALC, or GLA enzymes, enzyme activity can be assayed at relevant time points, as determined by the patient's physician, to determine whether enzyme activity levels are higher than prior to the commencement of treatment, and thus, monitor the efficacy of a particular treatment. Based on the level of enzyme activity measured during the treatment regimen, the patient's physician can make adjustment to the treatment (e.g., by varying the dosage of medications, or modifying therapy).

All journal articles, references and patent citations provided above and parentheses or otherwise, whether previously stated or not are incorporated herein by reference.

It is understood that modifications that do not substantially affect the function of the various embodiments of this invention are also included within the definition of the invention provided herein. Accordingly the following examples are intended to illustrate but not limit the present invention.

EXAMPLES

Example 1

Synthesis of GLA and GAA Substrate and Internal Standards

The methods used to synthesize the internal standards and substrates for the GLA and GAA assays are essentially the same as those described by Li et al. (2004, Clinical Chemistry 50:1785-96). The methodology is briefly summarized as follows:

General Methods. Thin layer chromatography (TLC) is carried out on silica plates (Merck, 60F$_{254}$), and flash column chromatography is carried out with silica gel (Merck, 230-400 Mesh). Preparative HPLC is carried out can be monitored with a UV detector (אּ=254 nm). Dry CH$_2$Cl$_2$ can be obtained by distillation from CaH$_2$ under Ar, and other dry solvents are obtained from Aldrich (Sure-Seal). As noted below, reactions are carried out in a round bottom flask (RBF) or in a vial with a Teflon septum-lined screw cap. $_1$H-NMR spectra are obtained on a Bruker DPX200 spectrometer (200 MHz) unless otherwise noted.

Acetic acid 4-nitro-phenyl ester (1): Acetic anhydride (50 ml) is added to a solution of 4-nitrophenol (5.56 g, 40 mmol) in dry pyridine (50 ml). The solution is stirred at ambient temperature for 2 hr and then at 70° C. overnight with a reflux condenser under Ar. The mixture is poured onto ice, and a white precipitate is formed after standing for several hours. Water (400 ml) is added, and the white solid is collected by vacuum filtration and dried in vacuo to yield a white solid (5.1 g, 70%). ESI-MS (M+H)$_+$: 182.2. $_1$H-NMR (CDCl$_3$) δ 8.30 (2H, d, J=9.0 Hz, NO$_2$CCH), 7.31 (2H, d, J=9.0 Hz, OCCH), 2.25 (3H, s, CH$_3$).

Acetic acid 4-acryloylamino-phenyl ester (2): H$_2$ is bubbled through a solution of 1 (280 mg, 1.54 mmol) and 10 mg of 10% Pd on carbon in 20 ml of MeOH for 1 hr. The catalyst is removed by filtration. Triethylamine (410 μl, 3.08 mmol) is added to the filtrate which was chilled on ice, then acryloyl chloride (250 μl, 3.08 mmol, Aldrich) in 10 ml of dry CH$_2$Cl$_2$ is added dropwise with stirring over 0.5 hr under Ar. The reaction is then allowed to return to ambient temperature, followed by 2 hr of stirring. Anion exchange resin (Bio-Rad, AG-MP1, OH_) (4 equivalents based on acryloyl chloride) is added, the mixture is filtered, and the filtrate is treated with sufficient cation exchange resin (Dowex, 50W×8, H$_+$) to bring the mixture to neutrality (moist pH paper). The resin is removed by filtration, and the solvent is removed by rotary evaporation to yield an off-white solid (268 mg, 85%). ESI-MS (M+H)$_+$: 206.1. $_1$H-NMR (acetone-d$_6$) δ 9.15 (1H, br, NH), 7.78 (2H, d, J=9.0 Hz, NHCCH), 7.08 (2H, d, J=9.0 Hz, NHCCHCH), 6.55~6.37 (2H, m, COCHCHH (anti to each other)), 5.75 (1H, dd, J=9.8 and 2.2 Hz, COCHCHH (syn to COCH)), 2.25 (3H, s, CH$_3$).

N-(4-Hydroxy-phenyl)-acrylamide (3). To 2 (200 mg, 0.98 mmol) in 1.5 ml of MeOH in a 5 ml screw-capped vial is added 1.0 ml of 0.5 M of sodium methoxide in MeOH. The mixture is stirred at ambient temperature, and the reaction is complete in 10 min. The mixture is neutralized by addition of cation exchange resin (Dowex, 50W×8, H$_+$) (moist pH paper). The resin is removed by filtration and washed with MeOH. The combined filtrate and wash is concentrated by rotary evaporation to yield an off-white solid (152 mg, 95%), ESI-MS (M+H)$_+$: 164.2. $_1$H-NMR (acetone-d$_6$), δ 9.15 (1H, br, NH), 7.59 (2H, d, J=9.0 Hz, NHCCH), 6.82 (2H, d, J=9.0 Hz, NHCCHCH), 6.52~6.35 (2H, m, COCHCHH (anti to each other)), 5.70 (1H, dd, J=9.8 and 2.2 Hz, COCHCHH (syn to COCH)).

4-Acrylaminophenyl α-D-galactopyranoside (4): The compound is prepared as described for 2 using 1 g of 4-nitrophenyl α-D-galactopyranoside (Sigma) to obtain 0.94 g (87%) of 4; ESI-MS (M+H)$_+$: 326.3. $_1$H-NMR (D$_2$O) δ 7.43 (2H, d, J=9.0 Hz, NHCCH), 7.16 (2H, d, J=9.0 Hz, NHCCHCH), 6.47~6.24 (2H, m, COCHCHH (anti to each other)), 5.81 (1H, dd, J=9.8 and 2.2 Hz, COCHCHH (syn to COCH)), 5.52 (1H, d, J=3.4 Hz, H-1), 4.01~3.86 (4H, m, H-2,3,4,5), 3.63~3.60 (2H, d, J=6.2 Hz, H-6, 6').

4-Acrylaminophenyl α-D-glucopyranoside (5): The compound is prepared as described for 4, using 1 g of 4-nitrophenyl α-D-glucopyranoside (Sigma) to obtain 0.97 g (90%) of 5; ESI-MS (M+H)$_+$: 326.3. $_1$H-NMR (D$_2$O) δ 7.43 (2H, d, J=9.0 Hz, NHCCH), 7.16 (2H, d, J=9.0 Hz, NHCCHCH), 6.47~6.24 (2H, m, COCHCHH (anti to each other)), 5.81 (1H, dd, J=9.8 and 2.2 Hz, COCHCHH (syn to COCH)), 5.60 (1H, d, J=3.6 Hz, 1-H), 3.94~3.66 (5H, m, H-2,3,5,6,6'), 3.48 (1H, t, J=9.2 Hz, H-4). N-(6-Amino-hexyl)-benzamide (6): To a stirred solution of 1,6-diaminohexane (10.0 g, 86.3 mmol, Aldrich) in 30 ml dry CH$_2$Cl$_2$ is added benzoyl chloride (1 ml, 8.6 mmol) in 300 ml dry CH$_2$Cl$_2$ dropwise at ambient temperature under Ar. A white precipitate formed as the reaction proceeded, and the mixture is stirred at ambient temperature for 5 hr after the addition is completed. Aqueous NaOH (3 ml of 4 N) is added to dissolve the precipitate. The reaction mixture is washed with water (3×60 ml), dried over Na$_2$SO$_4$ and solvent is removed by rotary evaporation. The oil was purified by flash chromatograph on silica eluting (Merck 230-400 Mesh) with 30:1 acetone/concentrated ammonium hydroxide to yield product as a yellowish oil (0.75 g, 32%). R$_f$=0.43 (TLC, same solvent). ESI-MS (M+H)$_+$: 221.3. $_1$H-NMR (acetone-d$_6$) δ 7.82~7.75 (2H, m, COCCH), 7.55~7.35 (3H, m, COCHCHCH), 6.35 (1H, br, NH), 3.42 (2H, dt, J=5.8 and 6.8 Hz, CONHCH$_2$), 3.20 (1H, t, J=6.8 Hz, NH$_2$CH$_2$), 1.90-1.32 (8H, m, NHCH$_2$(CH$_2$)$_4$).

N-(6-Amino-hexyl)-d$_5$-benzamide (7): The compound is prepared as for 6 using d$_5$-benzoyl chloride (Cambridge Isotope Inc.). ESI-MS (M+H)$_+$: 226.3. $_1$H-NMR (acetone-d$_6$) δ 6.35 (1H, br, NH), 3.42 (2H, dt, J=5.8 and 6.8 Hz, CONHCH$_2$), 3.20 (1H, t, J=6.8 Hz, NH$_2$CH$_2$), 1.90-1.32 (8H, m, NHCH$_2$(CH$_2$)$_4$).

N-(7-Amino-heptyl)-benzamide (8): The compound is prepared as for 6 using 1,7-diaminoheptane (Aldrich). ESI-MS (M+H)$_+$: 235.3. $_1$H-NMR (acetone-d$_6$) δ 7.82~7.75 (2H, m, COCCH), 7.55~7.35 (3H, m, COCHCHCH), 6.35 (1H, br, NH), 3.42 (2H, dt, J=5.8 and 6.8 Hz, CONHCH$_2$), 3.20 (1H, t, J=6.8 Hz, NH$_2$CH$_2$), 1.90-1.32 (10H, m, NHCH$_2$(CH$_2$)$_5$).

N-(7-Amino-heptyl)-d$_5$-benzamide (9): The compound is prepared as for 6 using d$_5$-benzoyl chloride. ESI-MS (M+H)$_+$: 240.3. $_1$H-NMR (acetone-d$_6$) δ6.35 (1H, br, NH), 3.42 (2H, dt, J=5.8 and 6.8 Hz, CONHCH$_2$), 3.20 (1H, t, J=6.8 Hz, NH$_2$CH$_2$), 1.90-1.32 (10H, m, NHCH$_2$(CH$_2$)$_5$).

(6-Benzoylamino-hexyl)-{2-[4-(3,4,5-trihydroxy-6-hydroxymethyl-tetrahydro-pyran-2-yloxy)-phenylcarbamoyl]-ethyl}-carbamic acid tert-butyl ester (GLA-S): Compound 4 (0.88 g, 2.7 mmol) and 6 (0.71 g, 3.2 mmol) in a solution of isopropanol (30 ml) and H$_2$O (4 ml) is stirred at 65° C. (oil bath) in a capped 100 ml RBF for 48 hrs. TLC on silica shows that at least 85% of 4 is converted to the Michael addition product (R$_f$=0, 30:1 acetone-concentrated ammonium hydroxide). The reaction is allowed to cool to ambient temperature, followed by the addition of powdered K$_2$CO$_3$ (0.44 g, 3.2 mmol) and di-tert-butylcarbonate (0.84 mg, 3.8 mmol, Aldrich). The mixture is stirred at ambient temperature for 3 hr. TLC should show at least 80% of Michael addition product was converted to the desired product ($R_f$=0.17, 10:1 acetone-concentrated ammonium hydroxide). The solid is collected by vacuum filtration and is washed with 30 ml of MeOH. The filtrates are combined, and solvent is removed by rotary evaporation to give an oily residue. MeOH (6.5 ml) is added to dissolve the residue, and the pH is adjusted to ~3-4 (moist pH paper) by addition of trifluoroacetic acid with chilling on ice. The desired product is purified by 10 runs of preparative HPLC: 50% MeOH in $H_2O$, at a flow rate of 6 ml/min; $t_R$=27 min. Product fractions are pooled, and most of the solvent is removed by rotary evaporation at ambient temperature. The remaining solvent is removed by lyophilization, and the resulting residue is dissolved in 20 ml of MeOH. Solvent is removed by rotary evaporation, and the oily residue is dried in vacuum to give a white solid (1.1 g, 63%). ESI-MS $(M+H)_+$: 646.6; $_1$H-NMR (1:2.5 $D_2O$/acetone-$d_6$) δ 7.80~7.75 (2H, m, COCCH), 7.55~7.35 (5H, m, COCHCHCH and NHCCH), 7.05 (2H, d, J=9.0 Hz, NHCCHCH), 5.39 (1H, d, J=3.4 Hz, H-1), 4.00~3.57 (6H, m, H-2,3,4,5,6,6'), 3.51 (2H, t, J=6.8 Hz, $COCH_2CH_2$), 3.30 (2H, t, J=7.0 Hz, $CONHCH_2$), 3.16 (2H, t, J=7.0 Hz, $CONH(CH_2)_5CH_2$), 2.55 (2H, t, J=6.4 Hz, $COCH_2$), 1.70-1.20 (17H, m, O-tert-$C_4H_9$ and $NHCH_2(CH_2)_4$).

(7-Benzoylamino-heptyl)-{2-[4-(3,4,5-trihydroxy-6-hydroxymethyl-tetrahydro-pyran-2-yloxy)-phenylcarbamoyl]-ethyl}-carbamic acid tert-butyl ester (GAA-S): The compound is prepared as for GLA-S starting from 0.63 g of 5 and 0.55 g of 8. HPLC $t_R$=40 min. Yield 60%. ESI-MS $(M+H)_+$: 660.6. $_1$H-NMR (1:2.5 $D_2O$/acetone-$d_6$) δ 7.80~7.75 (2H, m, COCCH), 7.55~7.35 (5H, m, COCHCHCH and NHCCH), 7.05 (2H, d, J=9.0 Hz, NHCCHCH), 5.39 (1H, d, J=3.6 Hz, H-1), 3.90~3.57 (5H, m, H-2,3,5,6,6'), 3.51 (2H, t, J=6.8 Hz, $COCH_2CH_2$), 3.45 (1H, t, j=9.6 Hz, H-4), 3.30 (2H, t, J=7.0 Hz, $CONHCH_2$), 3.20 (2H, t, J=7.0 Hz, $CONH(CH_2)_5CH_2$), 2.65 (2H, t, J=6.4 Hz, $COCH_2$), 1.70-1.20 (19H, m, O-tert-$C_4H_9$ and $NHCH_2(CH_2)_5$).

(6-$d_5$-Benzoylamino-hexyl)-[2-(4-hydroxy-phenylcarbamoyl)-ethyl]-carbamic acid tertbutyl ester (GLA-IS): Compound 3, 10 mg, 0.06 mmol) and 7 (21 mg, 0.09 mmol) are dissolved in 1.5 ml of isopropanol in a screw capped vial. The mixture is stirred at 65° C. overnight. TLC should show that more than 85% of 3 has been converted into the Michael addition product ($R_f$=0.22, 30:1 acetone/concentrated ammonium hydroxide solution). After the reaction is cooled to ambient temperature, $K_2CO_3$ (10 mg, 0.07 mmol) and di-tert-butylcarbonate (16 mg, 0.07 mmol) are added, and the mixture is stirred for 2 hr at the same temperature. TLC should show that all the Michael addition product has been converted into the desired product ($R_f$=0.93, 30:1 acetone/concentrated ammonium hydroxide solution). The final product is purified by HPLC (solvent A, $H_2O$; solvent B, MeOH; Gradient 0-30 min, 30-60% B; 30-70 min, 60-85%; flow rate 6 ml/min; $t_R$=45.4 min) to yield 22 mg of desired product (yield 75%). ESI-MS $(M+H)_+$: 489.5. $_1$H-NMR ($CDCl_3$) δ 8.78 and 8.48 (2H, br, NH), 7.35 (2H, d, J=9.0 Hz, NHCCH), 6.91 (1H, br, OH), 6.77 (2H, d, J=9.0 Hz, HOCCH), 3.47 (2H, t, J=6.2 Hz, $COCH_2CH_2$), 3.34 (2H, dt, J=5.8, 6.8 Hz, $CONHCH_2$), 3.09 (2H, t, J=6.8 Hz, $CONH(CH_2)_5CH_2$), 2.55 (2H, t, J=6.2 Hz, $COCH_2$), 1.70-1.10 (17H, m, O-tert-$C_4H_9$ and $NHCH_2(CH_2)_4$).

(6-Benzoylamino-hexyl)-[2-(4-hydroxy-phenylcarbamoyl)-ethyl]-carbamic acid tertbutyl ester (GLA-P): The compound is prepared as for GLA-IS using 10.4 mg of 6. HPLC $t_R$=45.3 min. Yield 72.1%. ESI-MS $(M+H)_+$: 484.5. $_1$H-NMR ($CDCl_3$) δ 8.78 and 8.48 (2H, br, NH), 7.84~7.79 (2H, m, COCCH), 7.55~7.35 (5H, m, NHCCH, COCHCHCH), 6.91 (1H, br, OH), 6.82 (2H, d, J=9.0 Hz, HOCCH), 3.57 (2H, t, J=6.2 Hz, $COCH_2CH_2$), 3.42 (2H, dt, J=5.8, 6.8 Hz, $CONHCH_2$), 3.20 (2H, t, J=6.8 Hz, $CONH(CH_2)_5CH_2$), 2.64 (2H, t, J=6.2 Hz, $COCH_2$), 1.70-1.10 (17H, m, O-tert-$C_4H_9$ and $NHCH_2(CH_2)_4$).

(7-$d_5$-Benzoylamino-heptyl)-[2-(4-hydroxy-phenylcarbamoyl)-ethyl]-carbamic acid tertbutyl ester (GAA-IS): The compound is prepared as for GLA-IS using 22 mg of 9. HPLC $t_R$=47.0 min. Yield 70.5%. ESI-MS $(M+H)_+$: 503.5. $_1$H-NMR ($CDCl_3$) δ 8.78 and 8.48 (2H, br, NH), 7.35 (2H, d, J=9.0 Hz, NHCCH), 6.91 (1H, br, OH), 6.77 (2H, d, J=9.0 Hz, HOCCH), 3.47 (2H, t, J=6.2 Hz, $COCH_2CH_2$), 3.34 (2H, dt, J=5.8, 6.8 Hz, $CONHCH_2$), 3.09 (2H, t, J=6.8 Hz, $CONH(CH_2)_6CH_2$), 2.55 (2H, t, J=6.2 Hz, $COCH_2$), 1.70-1.20 (19H, m, O-tert-$C_4H_9$ and $NHCH_2(CH_2)_5$).

(7-Benzoylamino-heptyl)-[2-(4-hydroxy-phenylcarbamoyl)-ethyl]-carbamic acid tertbutyl ester (GAA-P): The compound is prepared as for GAA-IS using 11 mg of 8. HPLC $t_R$=46.8 min. Yield 75.5%. ESI-MS $(M+H)_+$: 498.5. $_1$H-NMR ($CDCl_3$) δ 8.78 and 8.48 (2H, br, NH), 7.84~7.79 (2H, m, COCCH), 7.55~7.35 (5H, m, NHCCH, COCHCHCH), 6.91 (1H, br, OH), 6.82 (2H, d, J=9.0 Hz, HOCCH), 3.57 (2H, t, J=6.2 Hz, $COCH_2CH_2$), 3.42 (2H, dt, J=5.8, 6.8 Hz, $CONHCH_2$), 3.20 (2H, t, J=6.8 Hz, $CONH(CH_2)_5CH_2$), 2.64 (2H, t, J=6.2 Hz, $COCH_2$), 1.70-1.10 (19H, m, O-tert-$C_4H_9$ and $NHCH_2(CH_2)_5$).

Example 2

Enzyme Screening Assays

The following example describes the specific protocol used to perform the enzyme assays (ASM, first ABG, GAA, GLA, and GALC assay) of the present invention.

Prior to beginning the DBS extraction, the assay mixtures should be warmed to room temperature and vortexed briefly. If needed, the ABG and GALC assay mixtures can be warmed in hot (40-45° C.) water for 5 minutes if solutions are not clear (the GALC cocktail may remain slightly cloudy).

DBS Extraction Method

DBS were obtained from adult, adolescent, and newborn patients that had been previously diagnosed as having one of the lysosomal storage diseases described herein based on other diagnostic tests (referred to generally as "test samples"). Test samples were obtained from patients confirmed as having one of ASM, ABG, GAA, GLA, GALC, or MPS1 deficiencies. A 3 mm hole punch was used to punch smaller samples from the DBS. It is possible to punch 6 or 7 times from one DBS, however, punches should be taken preferably from the perimeter of the DBS, not the center. The hole punch was rinsed with 70% isopropanol (or 70% ethanol) and dried prior to use to prevent contamination. Each sample to be tested used two 3 mm punches (one punch in one well of a 96 well plate for the 1 hour incubation with the sodium phosphate buffer (i.e., the punch to be extracted) and one punch for the overnight incubation with the Krabbe (GALC) cocktail). In between samples, the punch was used to punch blank paper 3 to 4 times to reduce sample carryover. Control, or "normal" DBS were prepared from blood samples obtained from a commercial source (e.g., ProMedDX, Norton, Mass.).

One 3 mm punch of dried blood (for each sample to be assayed) was added to a well of a 96 well polypropylene plate. 70 μL of 20 mM Sodium phosphate buffer, pH 7.1 as then added to each well containing the DBS punch. The plate was then covered and sealed with aluminum plate sealing film, and the plate was examined to ensure that all of the DBS punches were in contact with the extraction buffer (If necessary, the plates were centrifuged for 1 minute at 4000 rpm; all centrifugation steps of this method are performed at 25° C.). The plates were incubated for 1 hour at 37° C. with orbital shaking.

Assay Preparation

Following incubation the plates were removed from the shaker. The assay mixes were added to the appropriate wells of a fresh 96 well plate, followed by the DBS extract in the following patterns.

To a 96 well polypropylene plate was added:
1) 15 μL ASM assay mix+10 μL DBS extract
2) 15 μL ABG assay mix+10 μL DBS extract
3) 15 μL GAA assay mix+10 μL DBS extract
4) 15 μL GLA assay mix+10 μL DBS extract
5) one punch of 3 mm dried blood spot per well (for each sample to be assayed)+30 μL GALC assay mix.

The plates were sealed with aluminum plate sealing film and incubated at 37° C. with orbital shaking (approximately 225 rpm) for 20-24 hours.

Following incubation, the plates were centrifuged at 4000 rpm for 1 minute. Each assay reaction was quenched by adding a 100 μL mixture of 1:1 Ethyl Acetate (EA):MeOH to each well. The assay mix was then aspirated and dispensed several times to ensure even mixture. The 5 extract/assay mix mixtures associated with one sample were then combined into a single well of a fresh deep well plate. Into each well of the deep well plate containing extracts, 400 μL EA and 400 μL $H_2O$ were added, in that order. The samples were aspirated and dispensed vigorously several times in order to mix. The deep well plate was then sealed with aluminum plate sealing tape and centrifuged for 5 minutes at 4000 rpm at 25° C. to create a phase separation.

Approximately 300 μL (the majority of the top phase) was then removed from the top layer (the organic phase) and transferred to a new deepwell microtiter plate and dried under a stream of nitrogen (25 PSI) in a 96 well drying apparatus. Where needed, the plate was heated to 25° C. to speed drying.

A silica filter plate was prepared by adding 100 mg of silica per well to a 96 well filter plate (Innovative Microplate Catalog #F2005). The vacuum source was protected with the presence of a vacuum line filter. The vacuum was set for a maximum of 5 inch Hg. The dispense speed of a pipetor was set to gentle and the silica was carefully washed by adding a 250 μL mixture of EA and MeOH, mixed at a ratio of 19:1. Vacuum pressure was applied and the wash was collected as waste. (Pipetting too vigorously or having the vacuum rate set too high can cause channeling in the silica, which should be avoided.) The collection plate was then replaced with clean deep well plate.

The assay samples were reconstituted by adding a 100 μL mixture of EA and MeOH, mixed at a ratio of 19:1, to each well. The plates were covered with aluminum plate sealing film and shaken on a microtiter plate shaker (speed 7=~200 rpm) for 5 minutes to resuspend. With the pipette set to lowest dispense speed, the samples were added to the corresponding wells of the filter plate in the vacuum manifold (with the clean, empty deep well plate underneath). Vacuum was applied and the plates were visually inspected to insure that all liquid has passed through. The vacuum was turned off and a 400 μL mixture of EA and MeOH, mixed at a ratio of 19:1, was added, and vacuum was applied to collect the eluant. An additional 400 μL of a 19:1 EA:MeOH was added, vacuum was applied, and the eluted sample was collected in the same well. The EA:MeOH wash was repeated 2 more times for a total wash volume of 1600 μL.

The resulting eluted samples were dried under a stream of $N_2$ (drying manifold set to 25° C.). In the event that the samples could not be analyzed immediately by mass spectrometry, the plates were sealed with aluminum plate sealing film and stored at −20° C.

Prior to analysis by mass spectrometry, the plates were warmed to room temperature and each well was reconstituted with 200 μL of reconstitution buffer (a mixture of acetonitrile and water with addition of formic acid: 80% Acetonitrile with 20% water and 0.2% Formic Acid). The plate was sealed with aluminum plate sealing film and shaken on a microtiter plate shaker (speed 7=~200 rpm) for 5 minutes to resuspend. After resuspension, the plate sealing film was removed and replaced with aluminum foil.

The samples were then analyzed by tandem mass spectrometry using methods known in to those of skill in the art, and summarized in brief below.

Mass Spectrometry Analysis

Data were obtained on an API 4000 triple quadrupole mass spectrometer interfaced with PAL autosampler and Agilent 1100 HPLC system. The electrospray source was operated in positive mode, and the ions were detected in multi-reaction monitoring (MRM) mode. In the MRM mode, a selected product ion was passed through the last (Q3) mass analyzer, whereas the first mass analyzer (Q1) was fixed to transmit the parent ion given rise to the selected product ion. Data were acquired and analyzed by Analyst 3.5. The instrument was adjusted to give an optimized response for all analytes (detailed settings for a hypothetical experiment are given in Appendix 1). Samples were introduced by autosampler and pumped by an Agilent 1100 HPLC system. The mobile phase was composed of 80/20 acetonitrile/Water with 0.1% formic acid. The flow rate was set at 200 μl/min. The injector port was flushed once with 100 μl methanol/0.1% formic acid and once with 100 μl 50/50 methanol/isopropanol before each injection. The amount of product was calculated from the ion abundance ratio of the product to the internal standard for a sample minus that of a blank, multiplied by the amount of added internal standard and divided by the response factor ratio of product to internal standard. The enzyme activity in units of μmol/h/mL blood was calculated assuming that 10 μL of DBS extraction solution contained one seventh of the total blood contained in a 3.2 mm DBS (2.8 μL of blood), i.e., 10 μL DBS extract contained 0.4 μL of blood.

Results

The results of the foregoing experiments are shown in FIGS. 3-7. As can be seen from the figures, the methods of the invention are able to discriminate between normal enzyme activity vs. abnormal enzyme activity in patients having one of the five lysosomal storage diseases described herein. FIGS. 3-7 also demonstrate that the enzyme assays are specific for the target enzyme. The "Other LSD" data column represents the level of enzyme activity for a given assay as measured in all the other test samples, presumed to be normal for that particular enzyme activity. The target enzyme activity was shown to be substantially lower in patients with the target disease than control samples and samples from patients diagnosed as having an LSD other than the target disease. Both control samples and "other LSD" patient samples revealed enzyme activity levels that are in the normal range.

Example 3

Second ABG Assay

The second ABG DBS assay measures the ABG-catalyzed cleavage of the fluorogenic substrate 4-MU-β-Glu by detecting the product 4-MU in a fluorometer.

Reagent Preparation

The following preparations are adequate for 20 plates. If possible, reagents should be made in batches large enough to cover an entire study. This is particularly important for the Buffered Extractant.

Substrate Stock Solution, 1 M 2.29 mL DMSO was added to 774.26 mg of 4-MU-β-Glu in a 15 mL screw cap tube. The mixture was thawed at RT until dissolved completely. The tube may be thawed briefly in a 37° C. if necessary. The solution was well vortexed and then 110 µL aliquots were placed in 1.5 mL microtubes. Aliquots of this solution can be thawed and refrozen several times, but should not be left thawed for more than two hours, and should be protected from light and moisture.

Buffered Extractant: 0.30M citrate phosphate with 1% sodium taurodeoxycholate and 1% triton X-100, pH 5.2

A solution of 0.15 M citric acid was prepared by dissolving 3.78 g of citric acid monohydrate in 120 mL of pure water.

A solution of 0.30 M sodium phosphate was prepared by dissolving 5.12 g of anhydrous dibasic sodium phosphate in 120 mL of water.

A 0.30 M citrate phosphate buffer was prepared by combining 93 mL of 0.15 M citric acid and 107 mL of 0.3 M sodium phosphate.

A 10% triton X-100 solution was prepared by measuring 10 mL of Triton X-100 and adding 0.30 M citrate phosphate buffer to a final volume of 100 mL.

The buffered extractant was prepared by adding 10 mL of 10% Triton X-100 to 1.00 g sodium taurodeoxycholate. 0.30 M citrate phosphate buffer was then added to a total volume of 100 mL. The pH was adjusted to pH 5.2 with sodium hydroxide or hydrochloric acid as necessary, and the solution was filter sterilized using a 0.22 µm filter unit.

CBE Stock Solution

To prepare the 0.26 M CBE stock solution, 8.30 mg conduritol B epoxide was added to 200 µL of DMSO.

4-MU Stock Solution, 25 mM Used for Standard Curve (Adequate for Over 200 plates)

To prepare the 4-MU stock solution, 5 mg of 4-MU was added into a microcentrifuge or 15 mL conical tube, and dissolved in 1.14 mL DMSO. Aliquots of this solution can be thawed and refrozen several times, but should not be left thawed for more than two hours, and should be protected from light and moisture.

Stop Buffer: 0.5 M EDTA, pH 11.3 to 12.0

To prepare the stop buffer, 5.20 g EDTA was dissolved in approximately 20 mL of water. The pH was adjusted to be in the range of 11.3 and 12.0. The final volume was adjusted to 25 mL with water.

Assay Procedure

Preparation of Test Samples:

DBS were prepared from 153 control subjects and 43 Gaucher disease patients using standard procedures (see, Appendix II). DBS were stored at −20° C. or below in tightly sealed plastic bags, and protected from moisture and condensation at all times.

To obtain DBS punches, a paper punch was first cleaned with water and then with 100% ethanol. The punch was wiped with a tissue and used to punch a clean blank Guthrie card several times to ensure that all residual ethanol is removed from the tool. One 3.2 mm disk was punched from a DBS onto a nonabsorbent surface, and then placed in a sample tube (one DBS punch per sample tube). Sufficient clearance from the edge of the spot and previous punch holes was left to ensure that a complete 3.2 mm circle saturated with blood is obtained. A clean, blank Guthrie card was punched several times between each additional test sample.

200 µl of Buffered Extractant was added to each sample tube. The DBS were mixed gently for 1 hour at RT on a rocking platform, and checked to make sure that paper discs were in constant contact with the moving liquid. After incubation, the filter paper punches were removed from the sample tubes, and the tubes were centrifuged at 14000 RPM for 30 minutes.

An Uninhibited Working Substrate Solution (4-MU-β-Glu) was prepared by combining 100 µl substrate stock solution with 7.9 ml water. An Inhibited Working Substrate Solution was prepared by combining 4 ml of the Uninhibited Working Substrate Solution with 7.5 µl CBE Stock Solution. Each of the Uninhibited and Inhibited Working Substrate Solutions were used within four hours.

Starting the Reaction:

Each test sample was assayed in duplicate for both Uninhibited and Inhibited Working Substrate solutions and, thus, requires four wells per sample. 80 µL of Uninhibited Working Substrate Solution was added to two wells per sample, and 80 µL of Inhibited Working Substrate Solution was added to two wells per sample. 16 wells were reserved for a standard curve. The enzyme reactions were initiated by adding 40 µL each of a test sample (extracted DBS) to all assay wells, being careful not disturb the pellet in the DBS sample tubes when removing 40 µL. The contents were mixed in well by pipetting up and down. The plate was sealed with an adhesive sealer or capmat, making sure that all wells were individually sealed. The plate was incubated in a 37° C. water bath for 20 hours.

Terminating the Reaction:

Each plate was centrifuged at approximately 2500 RPM for 5-10 minutes to remove condensate from sealing film, which was then carefully removed. 100 µL of Stop Buffer was added to all assay wells, but was not yet added to the wells for the standard curve. The assay wells were then covered with a plate sealer to protect them from contamination while making the standard curve.

Fluorescence Measurement:

A 12.5 µM 4-MU standard was prepared by diluting 5 µL of 25 mM 4-MU Stock Solution into 10 mL water. 120 µL of water was added to all standard curve wells, following by the addition of 120 µL of 12.5 µM 4-MU standard to the first two standard curve wells, which were mixed by pipetting up and down.

The standard was diluted serially by transferring 120 µL from the first duplicate standard curve wells to the consecutive pairs of wells. The dilution was ended after 6 transfer steps by discarding 120 µL from the 7th pair of wells, leaving the last two wells with water only. This serial dilution yielded the following quantities of standard in pmol per well: 750, 375, 188, 93.8, 46.9, 23.4, 11.7 and 0.

100 µL Stop Buffer was then added to all standard curve wells. The plate was sealed and centrifuged for one hour at 2500 RPM. The sealant was removed and the plate was immediately read in a fluorometer with 355 nm excitation and 460 nm emission wavelengths.

Data Processing

The individual fluorescence readings from the standard curve wells were plotted against the corresponding molar quantities per well. The equation (4-MU, pmol) =$\alpha$*fluorescence was fit to the data with $\alpha$ being the slope of the regression line (Note: If the correlation coefficient r of the standard curve is less than 0.98 the standard curve is invalid and should be repeated).

The average fluorescences of the duplicate pairs containing reaction mixture without CBE was then calculated. The average fluorescences of the duplicate pairs containing reaction mixture with CBE were also calculated, and subtracted from the average fluorescence of the reactions without CBE. The fluorescences of the standard wells was used to calculate a linear standard curve. The fluorescence differentials were converted into pmol per well by linear regression using the standard curve, and were then converted into pmol/(punch*h) by dividing the result by the incubation time in hours (normally 20 hours), and then multiplying by the fraction of each extract used per well (in this assay, the factor is 200:40=5).

A test for bad duplicates was also performed in which the difference of fluorescence within each pair of duplicate wells was calculated, wherein f the absolute difference was greater then 25% of the average fluorescence of the corresponding pair the result was invalid and the assay was repeated for the corresponding sample.

Figure 8:
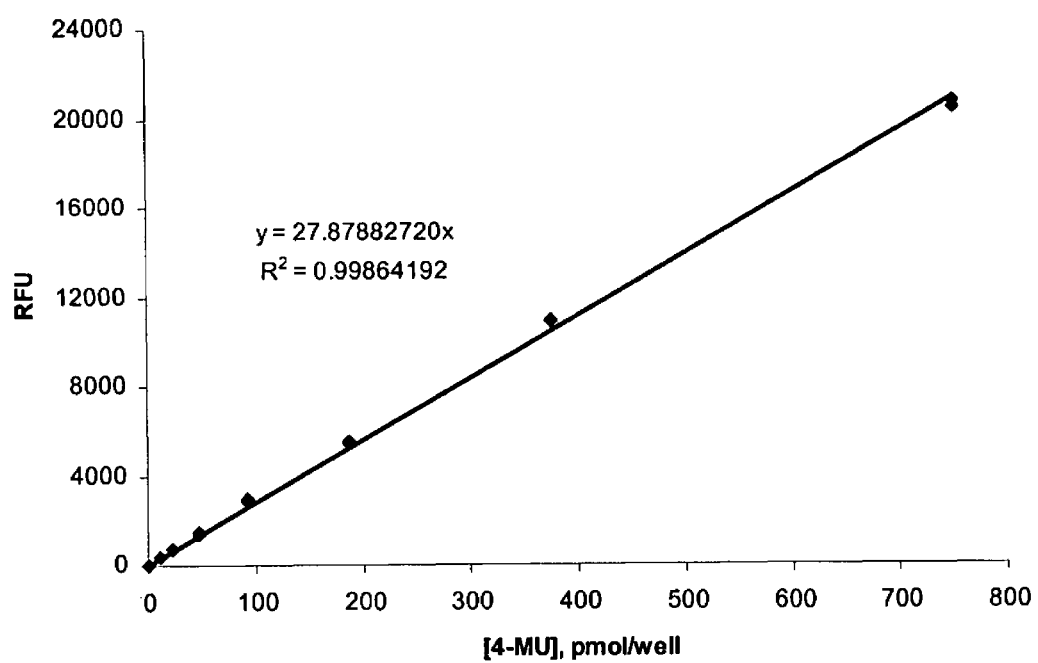
FIG. 8 shows a 4-MU standard curve.
Figure 9:
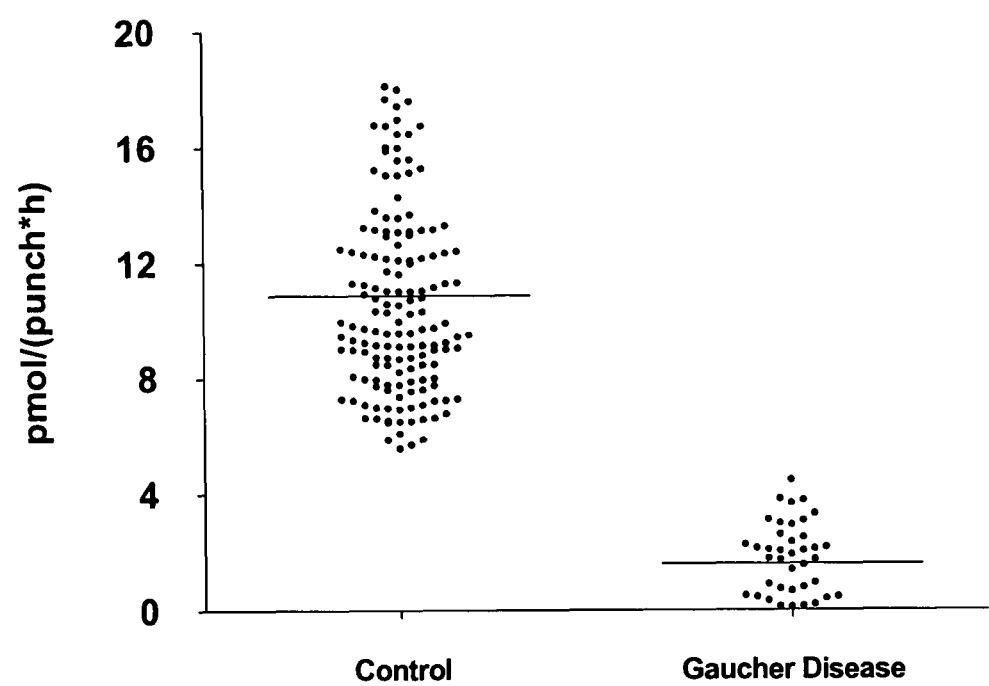
FIG. 9 shows an example of assay results obtained using the second ABG assay.

FIG. 8 shows the standard curve that was generated according to the foregoing description. FIG. 9 shows a comparison of the 153 control and 43 Gaucher disease patient samples. The solid lines indicate the mean for control and Gaucher disease samples at 10.87 and 1.58 μmol/(punch*h), respectively. These results demonstrate the ability of the second ABG assay to determine levels of ABG enzyme activity. and to discriminate between diseased and non-diseased patient samples.

APPENDIX I

Log Information from Devices at
Start of acquisition:

| | | |
|---|---|---|
| Pump | Agilent 1100 G1312A | 0 |
| Firmware Version | A.05.06 | |
| Serial Number | DE33213625 | |
| AutoSampler | CTC PAL | 0 |
| Loop Volume 1 (user entered) | | 20 μL |
| Actual Injection Volume | 30.000 μL | |
| Mass Spectrometer | API 4000 | 0 |
| Vacuum Gauge (10e−5 Torr) | 2.9 | |
| Source Temperature (at setpoint) | | 150.0 C. |
| Mass Spectrometer | API 4000 | 0 |
| End of Run - Detailed Status | | At Pressure |
| Vacuum Gauge (10e−5 Torr) | 2.9 | |
| Source Temperature (at setpoint) | | 150.0 C. |
| Acquisition Info | | |

| | |
|---|---|
| Sample Acq Duration: | 2 min 1 sec |
| Software Version: | Analyst 1.4.1 |
| Rack Code: | Stk1-01 |
| Rack Position: | 1 |
| Plate Code: | VT54 |
| Plate Position | 1 |

Agilent 1100 LC Pump Method Properties

| | |
|---|---|
| Pump Model: | Agilent 1100 LC Binary Pump |
| Minimum Pressure (psi): | 0.0 |
| Maximum Pressure (psi): | 5801.0 |
| Dead Volume (μl): | 40.0 |
| Maximum Flow Ramp (ml/min$^2$): | 100.0 |
| Maximum Pressure Ramp (psi/sec): | 290.0 |

Step Table:

| Step | Total Time(min) | Flow Rate(μl/min) | A (%) | B (%) |
|---|---|---|---|---|
| 0 | 0.00 | 200 | 0.0 | 100.0 |
| 1 | 2.00 | 200 | 0.0 | 100.0 |

CTC PAL Autosampler Method Properties

| | |
|---|---|
| Loop Volume1 (μl): | 20 |
| Loop Volume2 (μl): | 20 |
| Injection Volume (μl): | 30.000 |

APPENDIX I-continued

Period 1 Experiment 1:

| | |
|---|---|
| Scan Type: | MRM (MRM) |
| Polarity: | Positive |
| Scan Mode: | N/A |
| Ion Source: | Turbo Spray |
| Resolution Q1: | Unit |
| Resolution Q3: | Unit |
| Intensity Thres.: | 0.00 cps |
| Settling Time: | 0.0000 msec |
| MR Pause: | 5.0000 msec |
| MCA: | No |
| Step Size: | 0.00 amu |

| | Q1 Mass (amu) | Q3 Mass (amu) | Dwell (msec) | EntrancePotential (V) | Collision Energy (V) |
|---|---|---|---|---|---|
| ASM-IS | 370.32 | 264.27 | 100 | 2 | 25 |
| GALC-IS | 454.42 | 264.27 | 100 | 2 | 27 |
| ABG-IS | 510.48 | 264.27 | 100 | 2 | 30 |
| GLA-IS | 489.3 | 389.3 | 100 | 7 | 20 |
| GAA-IS | 503.32 | 403.32 | 100 | 7 | 20 |
| ASM-P | 398.36 | 264.27 | 100 | 2 | 27 |
| ABG-P | 482.45 | 264.27 | 100 | 2 | 29 |
| GALC-P | 426.39 | 264.27 | 100 | 2 | 27 |
| GAA-P | 498.29 | 398.29 | 100 | 7 | 20 |
| GLA-P | 484.27 | 384.27 | 100 | 7 | 20 |

Parameter Table
(Period 1 Experiment 1)

| | |
|---|---|
| Curtain gas (PSI): | 12.00 |
| GS1 (gas 1): | 12.00 |
| GS2 (gas 2): | 42.00 |
| IS (ionization source, V): | 4500.00 |
| TEM (Temperature ° C.): | 150.00 |
| CAD (CAD gas): | 4.00 |
| DP (Declustering Potential, V) | 20.00 |
| CXP (Collision Cell Exit Potential, V) | 20.00 |

APPENDIX II

DBS Preparation

The DBS samples can be prepared from blood collected by finger stick or from venous blood drawn in a vacuum collection tube containing EDTA anticoagulant. For neonates the sample can be collected by a heel stick.

For optimal sample collection:
a. The site of a finger or heel stick should be cleaned with an alcohol swab and air dried to avoid contamination.
b. Iodine-containing or non-volatile disinfectants should never be used.
c. The first drop of blood should never be used.
d. The stick site may be massaged gently to aid bleeding, but no significant pressure should be exerted to avoid dilution with interstitial fluid.
e. Fill one circle on a Guthrie Card by lightly touching the blood drop on the center of the circle and allowing the blood to soak through.
f. Blood drops should be large enough to fill a circle with a single application. Never apply a second drop to the same circle, even if it is only partially filled.
g. Blood should only be applied to one side of the filter paper, but must be completely visible on the reverse side for the specimen to be valid.
h. Fill as many circles on the Guthrie Card as possible to allow for repeat, follow-up and additional tests.

Venous blood samples collected in EDTA tubes can be applied to the filter paper by delivering 60 μL to 75 μL per dispense with a pipette.
a. Invert the collection tube three to six times immediately before spotting the filter paper to ensure the suspension of blood cells.
b. After blood is aspirated into the pipette, the pipette tip should be held very close to the surface of the center of a circle on the filter paper without touching it. With the paper in a horizontal position, gradually discharge the blood allowing it to soak into the paper.

APPENDIX II-continued

DBS Preparation

After drying, the card may be stored at −20° C. or below, or shipped. If it is necessary to ship or mail the card, consult local postal and transport regulations.

a. If several cards are placed in one envelope, ensure that the blood from each card does not contact the blood from adjacent cards. A physical barrier, such as paper sheets or fold-over sleeves can be placed between cards to avoid cross contamination.
b. Plastic bags should be avoided in the transport process because they act as vapor barriers. Residual moisture in the sample can negatively affect analysis.
c. Label each card before or immediately after blood is applied with date, time, sample identifier and any other required information.
d. Keep the filter paper in a horizontal position until the blood is dried, which should occur between 15° C. and 22° C. for a minimum of four hours. CAUTION: Contact with absorbent materials like paper or gauze needs to be avoided during this period.

The invention claimed is:

1. An assay mix for determining the activity of lysosomal acid α-glucosidase comprising (7-benzoylamino-heptyl)-{2-[4-(3,4,5-trihydroxy-6-hydroxymethyl-tetrahydro-pyran-2-yloxy)-phenylcarbamoyl]-ethyl}-carbamic acid tert-butyl ester, (7-d5-benzoylamino-heptyl)-[2-(4-hydroxy-phenylcarbamoyl)-ethyl]-carbamic acid tert-butyl ester, 3-[(3-cholamidopropyl)dimethylammonio]-1-propanesulfonate ("CHAPS"), acarbose and a buffer adjusted to a pH of 4.0, wherein the ratio of (7-benzoylamino-heptyl)-{2-[4-(3,4,5-trihydroxy-6-hydroxymethyl-tetrahydro-pyran-2-yloxy)-phenylcarbamoyl]ethyl}-carbamic acid tert-butyl ester to (7-d5-benzoylamino-heptyl)-[2-(4-hydroxy-phenylcarbamoyl)-ethyl]-carbamic acid tert-butyl ester is 100:1, the ratio of CHAPS to (7-benzoylamino-heptyl)-{2-[4-(3,4,5-trihydroxy-6-hydroxymethyl-tetrahydro-pyran-2-yloxy)-phenylcarbamoyl]-ethyl}-carbamic acid tert-butyl ester is 24.3:1, the ratio of acarbose to (7-benzoylamino-heptyl)-{2-[4-(3,4,5-trihydroxy-6-hydroxymethyl-tetrahydro-pyran-2-yloxy)-phenylcarbamoyl]-ethyl}-carbamic acid tert-butyl ester is 0.02:1, and the ratio of buffer to (7-benzoylamino-heptyl)-{2-[4-(3,4,5-trihydroxy-6-hydroxymethyl-tetrahydro-pyran-2-yloxy)-phenylcarbamoyl]ethyl}-carbamic acid tert-butyl ester is 450:1.

2. The assay mix of claim 1, comprising about 0.667 mM (7-benzoylamino-heptyl)-{2-[4-(3,4,5-trihydroxy-6-hydroxymethyl-tetrahydro-pyran-2-yloxy)-phenylcarbamoyl]-ethyl}-carbamic acid tert-butyl ester, about 6.67 μM 7-d5-benzoylaminoheptyl)-[2-(4-hydroxy-phenylcarbamoyl)-ethyl]-carbamic acid tert-butyl ester, about 10 g/L CHAPS, and about 13.3 μM acarbose.

3. The assay mix of claim 1, wherein the buffer is 0.3 M phosphate/citrate.

* * * * *

UNITED STATES PATENT AND TRADEMARK OFFICE
CERTIFICATE OF CORRECTION

PATENT NO. : 8,431,335 B2
APPLICATION NO. : 11/900528
DATED : April 30, 2013
INVENTOR(S) : Xiaokui K. Zhang et al.

Page 1 of 2

Figure 1D:
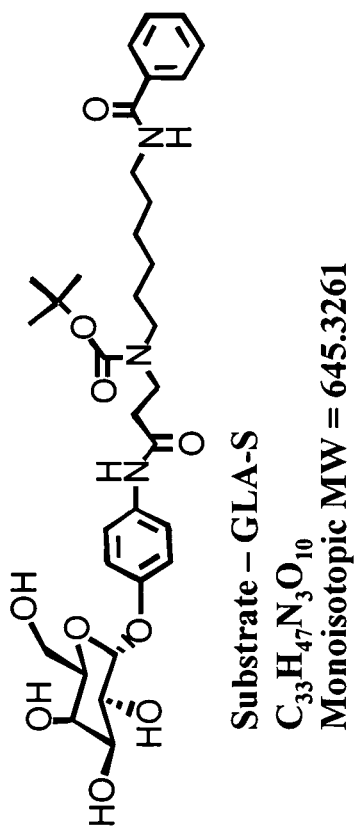
Figure 1E:
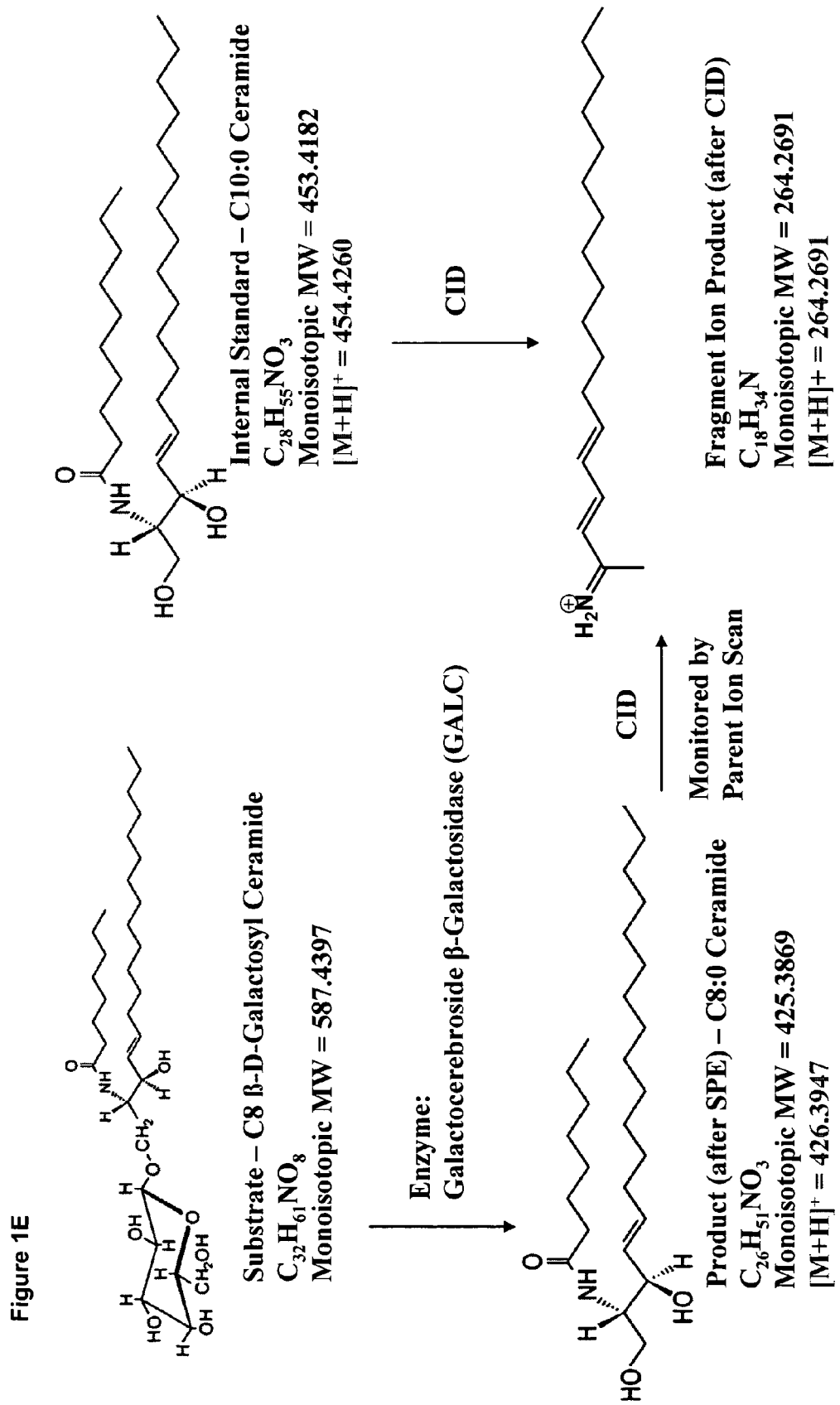

It is certified that error appears in the above-identified patent and that said Letters Patent is hereby corrected as shown below:

In the Drawings:

On sheet 4 of 13, in Figure 1D, line 1-5, delete "

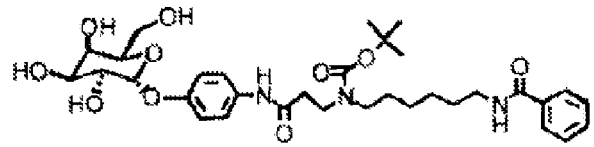

" 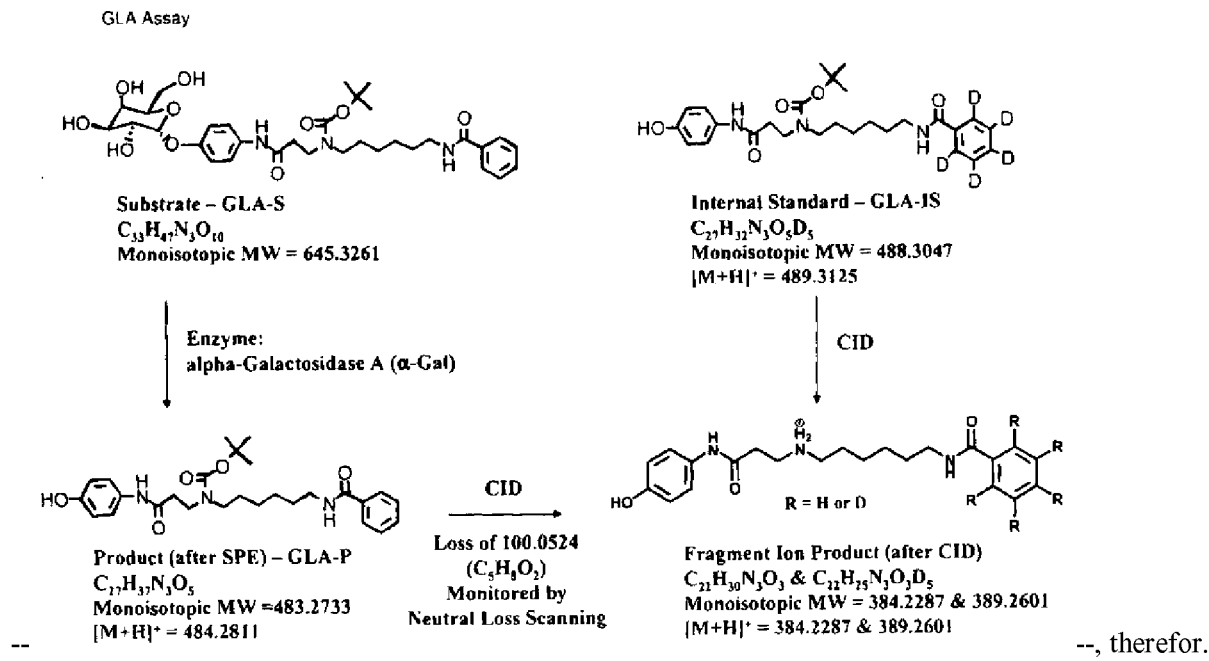

--, therefor.

Signed and Sealed this
Nineteenth Day of November, 2013

Teresa Stanek Rea
*Deputy Director of the United States Patent and Trademark Office*

CERTIFICATE OF CORRECTION (continued)
U.S. Pat. No. 8,431,335 B2

In the Specification:

In column 2, line 52, delete "CO" and insert -- C10 --, therefor.

In the Claims:

In column 60, line 15, in claim 1, delete "]ethyl" and insert -- ]-ethyl --, therefor.

In column 60, line 20, in claim 2, delete "7-d5" and insert -- (7-d5 --, therefor.